US 12,226,613 B2

United States Patent
Grygus et al.

(10) Patent No.: US 12,226,613 B2
(45) Date of Patent: *Feb. 18, 2025

(54) AUTO-INJECTOR AND RELATED METHODS OF USE

(71) Applicant: Regeneron Pharmaceuticals, Inc., Tarrytown, NY (US)

(72) Inventors: Bryan C. Grygus, Clifton Park, NY (US); Alfred Marino, Housatonic, MA (US); Rachel P. Arnott, San Francisco, CA (US); Scott Barton, Clifton Park, NY (US); Bart E. Burgess, Bernville, PA (US); Richard Gildersleeve, Rensselaer, NY (US); Alexei Goraltchouk, Cambridge, MA (US); Daniel Halbig, Ballston Lake, NY (US); Christopher Kanel, Hudson, NY (US); Trevor Langley, Rensselaer, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/063,212

(22) Filed: Dec. 8, 2022

(65) Prior Publication Data

US 2023/0105585 A1     Apr. 6, 2023

Related U.S. Application Data

(63) Continuation of application No. 16/495,868, filed as application No. PCT/US2018/031077 on May 4, 2018, now Pat. No. 11,547,801.

(Continued)

(51) Int. Cl.
*A61M 5/20* (2006.01)
*A61M 5/32* (2006.01)

(52) U.S. Cl.
CPC ........ *A61M 5/2033* (2013.01); *A61M 5/3202* (2013.01); *A61M 2005/2013* (2013.01); *A61M 2205/103* (2013.01); *A61M 2209/088* (2013.01)

(58) Field of Classification Search
CPC ........ A61M 5/2033; A61M 2005/2013; A61M 2205/103; A61M 2209/088
(Continued)

(56) References Cited

U.S. PATENT DOCUMENTS

| 2,459,304 A | 1/1949 | Frederick et al. |
| 3,340,671 A | 9/1967 | Loo |

(Continued)

FOREIGN PATENT DOCUMENTS

| AU | 1999018289 A1 | 9/1999 |
| AU | 2002301321 B2 | 6/2005 |

(Continued)

OTHER PUBLICATIONS

Invitation to Pay Additional Fees mailed Mar. 24, 2023 in International Application No. PCT/US2022/079921 (15 pages).

(Continued)

*Primary Examiner* — Michael J Tsai
*Assistant Examiner* — Nidah Hussain
(74) *Attorney, Agent, or Firm* — Bookoff McAndrews, PLLC

(57) ABSTRACT

An injection device includes a carrier, a needle, a driver coupled to the needle, the driver being slidable relative to the carrier between a retracted configuration and a deployed configuration, a shuttle configured to move the driver between the retracted configuration and the deployed configuration, and a stop configured to move from a first configuration to a second configuration, wherein the stop is configured to maintain the driver in the deployed configu- (Continued)

ration, and movement of the stop from the first configuration to the second configuration allows the shuttle to move the driver from the deployed configuration to the retracted configuration.

20 Claims, 23 Drawing Sheets

Related U.S. Application Data

(60) Provisional application No. 62/502,278, filed on May 5, 2017.

(58) Field of Classification Search
USPC .......................................................... 604/67
See application file for complete search history.

(56) References Cited

U.S. PATENT DOCUMENTS

| | | | |
|---|---|---|---|
| 3,342,180 A | 9/1967 | Roland et al. |
| 3,507,386 A | 4/1970 | Ishii et al. |
| 3,605,744 A | 9/1971 | Dwyer et al. |
| 3,872,992 A | 3/1975 | Larson |
| 3,916,894 A | 11/1975 | Cloyd |
| 4,187,861 A | 2/1980 | Heffernan |
| 4,244,287 A | 1/1981 | Maffet |
| 4,396,385 A | 8/1983 | Kelly et al. |
| 4,397,903 A | 8/1983 | Allen et al. |
| 4,410,323 A | 10/1983 | Hodosh et al. |
| 4,548,601 A | 10/1985 | Lary |
| 4,624,660 A | 11/1986 | Mijers et al. |
| 4,703,781 A | 11/1987 | Meyer et al. |
| 4,973,504 A | 11/1990 | Romberg et al. |
| 4,997,423 A | 3/1991 | Okuda et al. |
| 5,009,646 A | 4/1991 | Sudo et al. |
| 5,073,169 A | 12/1991 | Raiken |
| 5,088,996 A | 2/1992 | Kopfer et al. |
| 5,180,371 A | 1/1993 | Spinello |
| 5,220,948 A | 6/1993 | Haber et al. |
| 5,279,606 A | 1/1994 | Haber et al. |
| 5,288,560 A | 2/1994 | Sudo et al. |
| 5,322,515 A | 6/1994 | Karas et al. |
| 5,334,179 A | 8/1994 | Poli et al. |
| 5,354,287 A | 10/1994 | Wacks |
| 5,372,787 A | 12/1994 | Ritter |
| 5,382,235 A | 1/1995 | Sak |
| 5,466,220 A | 11/1995 | Brenneman |
| 5,487,732 A | 1/1996 | Jeffrey |
| 5,514,116 A | 5/1996 | Vaillancourt et al. |
| 5,690,618 A | 11/1997 | Smith et al. |
| 5,814,020 A | 9/1998 | Gross |
| 5,858,001 A | 1/1999 | Tsals et al. |
| 5,873,860 A | 2/1999 | Kahlert |
| 5,902,276 A | 5/1999 | Namey, Jr. |
| 5,951,527 A | 9/1999 | Sudo |
| 6,003,566 A | 12/1999 | Thibault et al. |
| 6,003,736 A | 12/1999 | Ljunggren |
| 6,004,300 A | 12/1999 | Butcher et al. |
| 6,022,339 A | 2/2000 | Fowles et al. |
| 6,074,369 A | 6/2000 | Sage et al. |
| 6,090,070 A | 7/2000 | Hager et al. |
| 6,090,081 A | 7/2000 | Sudo et al. |
| 6,123,991 A | 9/2000 | Spallek et al. |
| 6,129,712 A | 10/2000 | Sudo et al. |
| 6,142,977 A | 11/2000 | Kolberg et al. |
| 6,149,614 A | 11/2000 | Dunshee et al. |
| 6,162,200 A | 12/2000 | Sawa et al. |
| 6,165,155 A | 12/2000 | Jacobsen et al. |
| 6,171,276 B1 | 1/2001 | Lippe et al. |
| 6,189,580 B1 | 2/2001 | Thibault et al. |
| 6,238,367 B1 | 5/2001 | Christiansen et al. |
| 6,277,095 B1 | 8/2001 | Kriesel et al. |
| 6,346,095 B1 | 2/2002 | Gross et al. |
| 6,364,865 B1 | 4/2002 | Lavi et al. |
| 6,378,576 B2 | 4/2002 | Thibault et al. |
| 6,478,771 B1 | 11/2002 | Lavi et al. |
| 6,500,150 B1 | 12/2002 | Gross et al. |
| 6,511,459 B1 | 1/2003 | Fago |
| 6,547,755 B1 | 4/2003 | Lippe et al. |
| 6,585,693 B1 | 7/2003 | Dischler |
| 6,595,956 B1 | 7/2003 | Gross et al. |
| 6,641,565 B1 | 11/2003 | Lavi et al. |
| 6,645,181 B1 | 11/2003 | Lavi et al. |
| 6,681,946 B1 | 1/2004 | Jansen et al. |
| 6,689,108 B2 | 2/2004 | Lavi et al. |
| 6,723,068 B2 | 4/2004 | Lavi et al. |
| 6,799,612 B2 | 10/2004 | Stewart et al. |
| 6,817,990 B2 | 11/2004 | Yap et al. |
| 6,824,529 B2 | 11/2004 | Gross et al. |
| 6,837,876 B2 | 1/2005 | Bally et al. |
| 6,843,782 B2 | 1/2005 | Gross et al. |
| 6,913,591 B2 | 7/2005 | Itoh et al. |
| 6,939,324 B2 | 9/2005 | Gonnelli et al. |
| 6,945,417 B2 | 9/2005 | Jansen et al. |
| 7,001,360 B2 | 2/2006 | Veasey et al. |
| 7,004,928 B2 | 2/2006 | Aceti et al. |
| 7,195,609 B2 | 3/2007 | Huegli |
| 7,250,037 B2 | 7/2007 | Shermer et al. |
| 7,294,752 B1 | 11/2007 | Propp |
| 7,384,413 B2 | 6/2008 | Gross et al. |
| 7,416,540 B2 | 8/2008 | Edwards et al. |
| 7,455,663 B2 | 11/2008 | Bikovsky |
| 7,481,792 B2 | 1/2009 | Gonnelli et al. |
| 7,547,297 B2 | 6/2009 | Brinkhues |
| 7,563,253 B2 | 7/2009 | Tanner et al. |
| D602,155 S | 10/2009 | Foley et al. |
| D602,586 S | 10/2009 | Foley et al. |
| 7,628,770 B2 | 12/2009 | Ethelfeld |
| 7,648,482 B2 | 1/2010 | Edwards et al. |
| 7,648,483 B2 | 1/2010 | Edwards et al. |
| 7,674,246 B2 | 3/2010 | Gillespie et al. |
| 7,678,072 B2 | 3/2010 | Weber |
| 7,678,079 B2 | 3/2010 | Shermer et al. |
| 7,691,308 B2 | 4/2010 | Brinkhues |
| 7,727,202 B2 | 6/2010 | Kirchhofer et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,749,202 B2 | 7/2010 | Miller et al. |
| 7,766,873 B2 | 8/2010 | Moberg et al. |
| 7,766,882 B2 | 8/2010 | Sudo et al. |
| 7,780,636 B2 | 8/2010 | Radmer et al. |
| 7,883,660 B2 | 2/2011 | Matsuda et al. |
| 7,892,199 B2 | 2/2011 | Mhatre et al. |
| 7,892,206 B2 | 2/2011 | Moberg et al. |
| 7,909,796 B2 | 3/2011 | Weber |
| 7,918,823 B2 | 4/2011 | Edwards et al. |
| 7,922,699 B2 | 4/2011 | Baba et al. |
| 7,927,315 B2 | 4/2011 | Sudo et al. |
| 7,947,017 B2 | 5/2011 | Edwards et al. |
| 7,981,085 B2 | 7/2011 | Ethelfeld |
| 7,988,675 B2 | 8/2011 | Gillespie, III et al. |
| 7,993,301 B2 | 8/2011 | Boyd et al. |
| 7,998,117 B2 | 8/2011 | Gross et al. |
| 8,016,788 B2 | 9/2011 | Edwards et al. |
| 8,021,344 B2 | 9/2011 | Edwards et al. |
| 8,052,648 B2 | 11/2011 | Dikeman et al. |
| 8,057,434 B2 | 11/2011 | Burroughs et al. |
| 8,062,257 B2 | 11/2011 | Moberg et al. |
| 8,065,096 B2 | 11/2011 | Moberg et al. |
| 8,088,096 B2 | 1/2012 | Lauchard et al. |
| 8,105,281 B2 | 1/2012 | Edwards et al. |
| 8,123,719 B2 | 2/2012 | Edwards et al. |
| 8,123,724 B2 | 2/2012 | Gillespie, III |
| 8,147,460 B2 | 4/2012 | Etter et al. |
| 8,162,898 B1 | 4/2012 | Wright |
| 8,172,082 B2 | 5/2012 | Edwards et al. |
| 8,172,804 B2 | 5/2012 | Bikovsky |
| 8,182,447 B2 | 5/2012 | Moberg et al. |
| 8,202,249 B2 | 6/2012 | Iio et al. |
| 8,206,351 B2 | 6/2012 | Sugimoto et al. |
| 8,206,360 B2 | 6/2012 | Edwards et al. |
| 8,226,610 B2 | 7/2012 | Edwards et al. |

(56) References Cited

U.S. PATENT DOCUMENTS

| | | |
|---|---|---|
| 8,226,615 B2 | 7/2012 | Bikovsky |
| 8,231,573 B2 | 7/2012 | Edwards et al. |
| 8,267,893 B2 | 9/2012 | Moberg et al. |
| 8,287,500 B2 | 10/2012 | Baba et al. |
| 8,298,171 B2 | 10/2012 | Ishikawa et al. |
| 8,303,535 B2 | 11/2012 | Both et al. |
| 8,303,549 B2 | 11/2012 | Mejlhede et al. |
| 8,313,466 B2 | 11/2012 | Edwards et al. |
| 8,348,898 B2 | 1/2013 | Cabiri |
| 8,361,026 B2 | 1/2013 | Edwards et al. |
| 8,361,027 B2 | 1/2013 | Gross et al. |
| 8,361,028 B2 | 1/2013 | Gross et al. |
| 8,361,029 B2 | 1/2013 | Edwards et al. |
| D676,549 S | 2/2013 | Lovell et al. |
| 8,376,985 B2 | 2/2013 | Pongpairochana et al. |
| 8,409,141 B2 | 4/2013 | Johansen et al. |
| 8,425,462 B2 | 4/2013 | Edwards et al. |
| 8,433,383 B2 | 4/2013 | O'Neil et al. |
| 8,444,604 B2 | 5/2013 | Cindrich et al. |
| 8,453,838 B2 | 6/2013 | Hill |
| 8,460,244 B2 | 6/2013 | Srisathapat et al. |
| 8,475,414 B2 | 7/2013 | Boyd et al. |
| 8,512,287 B2 | 8/2013 | Cindrich et al. |
| 8,512,288 B2 | 8/2013 | Moberg et al. |
| 8,540,681 B2 | 9/2013 | Hetherington |
| 8,544,645 B2 | 10/2013 | Edwards et al. |
| 8,562,567 B2 | 10/2013 | Gundberg |
| 8,603,027 B2 | 12/2013 | Favreau |
| 8,603,045 B2 | 12/2013 | Weber |
| 8,608,698 B2 | 12/2013 | Edwards et al. |
| 8,617,110 B2 | 12/2013 | Moberg et al. |
| 8,618,948 B2 | 12/2013 | Oberli et al. |
| 8,627,816 B2 | 1/2014 | Edwards et al. |
| 8,641,669 B2 | 2/2014 | Renz et al. |
| 8,647,074 B2 | 2/2014 | Moberg et al. |
| 8,647,296 B2 | 2/2014 | Moberg et al. |
| 8,652,387 B2 | 2/2014 | Etter et al. |
| 8,668,672 B2 | 3/2014 | Moberg et al. |
| 8,668,675 B2 | 3/2014 | Chase et al. |
| 8,668,972 B2 | 3/2014 | Lewis et al. |
| 8,679,055 B2 | 3/2014 | Ishikawa et al. |
| 8,679,395 B2 | 3/2014 | Nagel et al. |
| 8,690,827 B2 | 4/2014 | Edwards et al. |
| 8,690,836 B2 | 4/2014 | Mathews et al. |
| 8,708,971 B2 | 4/2014 | Segal |
| 8,715,237 B2 | 5/2014 | Moberg et al. |
| 8,722,178 B2 | 5/2014 | Ashmead et al. |
| 8,740,847 B2 | 6/2014 | Levesque et al. |
| 8,742,032 B2 | 6/2014 | Abe et al. |
| 8,748,544 B2 | 6/2014 | Abe et al. |
| 8,771,239 B2 | 7/2014 | Boyd et al. |
| 8,795,669 B2 | 8/2014 | Walsh et al. |
| 8,808,244 B2 | 8/2014 | Adlon et al. |
| 8,834,419 B2 | 9/2014 | Jennings |
| 8,852,141 B2 | 10/2014 | Mhatre et al. |
| 8,858,511 B2 | 10/2014 | Gonnelli et al. |
| 8,864,739 B2 | 10/2014 | Moberg et al. |
| 8,876,779 B2 | 11/2014 | Johansen et al. |
| 8,900,201 B2 | 12/2014 | Edhouse et al. |
| 8,900,205 B2 | 12/2014 | Ishii |
| 8,915,882 B2 | 12/2014 | Cabiri |
| 8,920,367 B2 | 12/2014 | Edwards et al. |
| 8,920,374 B2 | 12/2014 | Bokelman et al. |
| 8,920,377 B2 | 12/2014 | Edwards et al. |
| 8,926,569 B2 | 1/2015 | Bisegna et al. |
| 8,926,594 B2 | 1/2015 | Edwards et al. |
| 8,939,935 B2 | 1/2015 | O'Connor et al. |
| 8,939,943 B2 | 1/2015 | Edwards et al. |
| D723,157 S | 2/2015 | Clemente et al. |
| 8,945,056 B2 | 2/2015 | Iio et al. |
| 8,956,331 B2 | 2/2015 | Johansen et al. |
| 8,960,685 B2 | 2/2015 | Maeda et al. |
| 8,961,469 B2 | 2/2015 | Sonderegger et al. |
| 8,968,260 B2 | 3/2015 | Horiuchi et al. |
| 8,974,413 B2 | 3/2015 | Baba et al. |
| 8,992,478 B2 | 3/2015 | Levesque |
| 8,998,842 B2 | 4/2015 | Lauchard et al. |
| 9,011,371 B2 | 4/2015 | Moberg et al. |
| 9,022,022 B2 | 5/2015 | Edwards et al. |
| 9,024,768 B2 | 5/2015 | Mandro et al. |
| 9,033,925 B2 | 5/2015 | Moberg et al. |
| 9,039,664 B2 | 5/2015 | Ogawa et al. |
| 9,056,170 B2 | 6/2015 | Edwards et al. |
| 9,072,839 B2 | 7/2015 | Kouyoumjian et al. |
| 9,078,976 B2 | 7/2015 | Boyd et al. |
| 9,084,849 B2 | 7/2015 | Edwards et al. |
| 9,101,706 B2 | 8/2015 | Gonnelli et al. |
| 9,107,996 B2 | 8/2015 | Brüggemann et al. |
| 9,107,999 B2 | 8/2015 | Moberg et al. |
| 9,108,012 B2 | 8/2015 | Pryce et al. |
| 9,114,213 B2 | 8/2015 | Murakami et al. |
| 9,132,231 B2 | 9/2015 | Gross et al. |
| D741,995 S | 10/2015 | Prasser et al. |
| 9,149,575 B2 | 10/2015 | Cabiri |
| 9,149,578 B2 | 10/2015 | Byerly et al. |
| 9,149,579 B2 | 10/2015 | Edwards et al. |
| 9,149,582 B2 | 10/2015 | Sugimoto et al. |
| 9,155,844 B2 | 10/2015 | Brereton et al. |
| 9,162,427 B2 | 10/2015 | Nakano et al. |
| 9,173,880 B2 | 11/2015 | Dix et al. |
| 9,173,999 B2 | 11/2015 | Edwards et al. |
| 9,180,244 B2 | 11/2015 | Anderson et al. |
| D745,142 S | 12/2015 | O'Connor et al. |
| 9,238,108 B2 | 1/2016 | Edwards et al. |
| 9,242,047 B2 | 1/2016 | Brereton et al. |
| 9,254,373 B2 | 2/2016 | Hørdum |
| 9,259,531 B2 | 2/2016 | Kamen et al. |
| 9,259,539 B2 | 2/2016 | Edwards et al. |
| 9,265,892 B2 | 2/2016 | Segal |
| 9,278,177 B2 | 3/2016 | Edwards et al. |
| 9,278,182 B2 | 3/2016 | Edwards et al. |
| 9,297,370 B2 | 3/2016 | Bruggemann et al. |
| 9,308,329 B2 | 4/2016 | Boyd et al. |
| 9,327,073 B2 | 5/2016 | Moberg et al. |
| 9,327,077 B2 | 5/2016 | Edwards et al. |
| 9,339,605 B2 | 5/2016 | Wimpenny et al. |
| 9,344,024 B2 | 5/2016 | Favreau |
| 9,345,837 B2 | 5/2016 | Horiuchi et al. |
| 9,352,090 B2 | 5/2016 | Brereton et al. |
| 9,352,091 B2 | 5/2016 | Edwards et al. |
| 9,364,606 B2 | 6/2016 | Cindrich et al. |
| 9,364,608 B2 | 6/2016 | Moberg et al. |
| 9,364,612 B2 | 6/2016 | Hanson et al. |
| 9,375,529 B2 | 6/2016 | Searle et al. |
| 9,375,532 B2 | 6/2016 | Brereton et al. |
| 9,408,984 B2 | 8/2016 | Durack et al. |
| 9,408,985 B2 | 8/2016 | Cronenberg et al. |
| 9,415,169 B2 | 8/2016 | Tachikawa et al. |
| D767,120 S | 9/2016 | Tyce et al. |
| 9,433,732 B2 | 9/2016 | Moberg et al. |
| 9,452,264 B2 | 9/2016 | Maeda et al. |
| D768,288 S | 10/2016 | O'Connor et al. |
| 9,463,280 B2 | 10/2016 | Cabiri |
| 9,468,586 B2 | 10/2016 | Kvale |
| 9,474,869 B2 | 10/2016 | Edwards et al. |
| 9,480,793 B2 | 11/2016 | Mhatre et al. |
| 9,492,610 B2 | 11/2016 | Cabiri |
| 9,492,618 B2 | 11/2016 | Day |
| 9,504,793 B2 | 11/2016 | Eggert et al. |
| D774,640 S | 12/2016 | Tyce et al. |
| 9,511,189 B2 | 12/2016 | O'Connor et al. |
| 9,522,231 B2 | 12/2016 | Schneider et al. |
| 9,522,234 B2 | 12/2016 | Cabiri |
| 9,526,837 B2 | 12/2016 | Carrel et al. |
| D776,262 S | 1/2017 | Tyce et al. |
| D776,263 S | 1/2017 | Tyce et al. |
| D776,264 S | 1/2017 | Tyce et al. |
| D776,265 S | 1/2017 | Tyce et al. |
| 9,533,092 B2 | 1/2017 | Gyrn |
| 9,539,392 B2 | 1/2017 | Jennings et al. |
| 9,542,826 B2 | 1/2017 | Edwards et al. |
| 9,555,187 B2 | 1/2017 | Sonderegger et al. |
| 9,555,191 B2 | 1/2017 | Edwards et al. |
| 9,572,927 B2 | 2/2017 | Brüggemann et al. |

(56) References Cited

U.S. PATENT DOCUMENTS

| | | |
|---|---|---|
| 9,572,932 B2 | 2/2017 | Eggert et al. |
| 9,579,459 B2 | 2/2017 | Jennings et al. |
| 9,579,461 B2 | 2/2017 | Sonderegger et al. |
| 9,586,737 B2 | 3/2017 | Klumpen |
| 9,597,450 B2 | 3/2017 | Cindrich et al. |
| 9,597,458 B2 | 3/2017 | Ashmead et al. |
| 9,598,195 B2 | 3/2017 | Deutschle et al. |
| 9,604,003 B2 | 3/2017 | Brereton et al. |
| 9,610,407 B2 | 4/2017 | Bruggemann et al. |
| 9,623,181 B2 | 4/2017 | Brereton et al. |
| 9,623,186 B2 | 4/2017 | Matsutani et al. |
| 9,636,451 B2 | 5/2017 | Gonnelli et al. |
| 9,636,459 B2 | 5/2017 | Brereton et al. |
| 9,642,969 B2 | 5/2017 | Ivosevic et al. |
| 9,656,021 B2 | 5/2017 | Brereton et al. |
| 9,669,163 B2 | 6/2017 | McNall, III et al. |
| 9,675,752 B2 | 6/2017 | Christensen |
| 9,687,607 B2 | 6/2017 | Brereton et al. |
| D791,306 S | 7/2017 | Clemente et al. |
| 9,707,335 B2 | 7/2017 | Agard et al. |
| 9,707,337 B2 | 7/2017 | O'Connor et al. |
| 9,707,352 B2 | 7/2017 | Helmer et al. |
| D794,770 S | 8/2017 | Wu et al. |
| D794,771 S | 8/2017 | Wu et al. |
| D794,776 S | 8/2017 | Tyce et al. |
| 9,717,850 B2 | 8/2017 | Sonderegger |
| 9,717,858 B2 | 8/2017 | Hara et al. |
| 9,718,881 B2 | 8/2017 | Gromada et al. |
| 9,724,471 B2 | 8/2017 | Edwards et al. |
| 9,731,074 B2 | 8/2017 | Ishikawa et al. |
| 9,737,655 B2 | 8/2017 | Clemente et al. |
| 9,737,669 B2 | 8/2017 | Edwards et al. |
| 9,744,297 B2 | 8/2017 | Cabiri et al. |
| 9,752,003 B2 | 9/2017 | Minagawa |
| 9,764,092 B2 | 9/2017 | Cabiri |
| 9,775,957 B2 | 10/2017 | Despa et al. |
| 9,789,255 B2 | 10/2017 | Brereton et al. |
| 9,795,735 B2 | 10/2017 | Levesque et al. |
| 9,802,030 B2 | 10/2017 | Clemente et al. |
| D804,019 S | 11/2017 | Costello et al. |
| 9,814,832 B2 | 11/2017 | Agard et al. |
| 9,814,838 B2 | 11/2017 | Edwards et al. |
| 9,821,117 B2 | 11/2017 | Anderson et al. |
| 9,821,120 B2 | 11/2017 | Nakano |
| 9,827,377 B2 | 11/2017 | Takai et al. |
| D804,650 S | 12/2017 | Costello et al. |
| D805,186 S | 12/2017 | Costello et al. |
| D805,187 S | 12/2017 | Costello et al. |
| D805,188 S | 12/2017 | Costello et al. |
| D805,189 S | 12/2017 | Costello et al. |
| D805,190 S | 12/2017 | Costello et al. |
| D805,632 S | 12/2017 | Costello et al. |
| D805,633 S | 12/2017 | Costello et al. |
| D806,234 S | 12/2017 | Costello et al. |
| D806,235 S | 12/2017 | Costello et al. |
| 9,833,561 B2 | 12/2017 | Chambers et al. |
| 9,833,562 B2 | 12/2017 | Sonderegger et al. |
| 9,833,573 B2 | 12/2017 | Edwards et al. |
| 9,836,948 B2 | 12/2017 | Edwards et al. |
| 9,850,445 B2 | 12/2017 | Minagawa |
| D806,863 S | 1/2018 | Costello et al. |
| D807,499 S | 1/2018 | Costello et al. |
| D808,011 S | 1/2018 | Costello et al. |
| 9,855,390 B2 | 1/2018 | Bisegna et al. |
| 9,867,938 B2 | 1/2018 | Edwards et al. |
| 9,867,946 B2 | 1/2018 | Iwano et al. |
| 9,872,633 B2 | 1/2018 | Limaye et al. |
| 9,878,091 B2 | 1/2018 | Cabiri |
| D810,278 S | 2/2018 | Cabiri et al. |
| D810,279 S | 2/2018 | Cabiri et al. |
| D811,583 S | 2/2018 | Cabiri et al. |
| D811,584 S | 2/2018 | Cabiri et al. |
| 9,889,254 B2 | 2/2018 | Haenggi |
| D812,738 S | 3/2018 | Wolford |
| D812,739 S | 3/2018 | Wolford |
| D813,380 S | 3/2018 | Stonecipher et al. |
| 9,911,308 B2 | 3/2018 | Edwards et al. |
| 9,913,942 B2 | 3/2018 | Brereton et al. |
| 9,919,097 B2 | 3/2018 | Sonderegger et al. |
| 9,925,342 B2 | 3/2018 | Carrel et al. |
| 9,925,344 B2 | 3/2018 | Brereton et al. |
| 9,943,653 B2 | 4/2018 | Kamen et al. |
| 9,950,123 B2 | 4/2018 | Brereton et al. |
| D817,481 S | 5/2018 | Cabiri et al. |
| 9,956,345 B2 | 5/2018 | Anderson et al. |
| 9,968,731 B2 | 5/2018 | Gonnelli et al. |
| 9,981,083 B2 | 5/2018 | Gonnelli et al. |
| 9,981,088 B2 | 5/2018 | Byerly |
| 9,981,089 B2 | 5/2018 | Ishida et al. |
| 9,987,419 B2 | 6/2018 | Hanson et al. |
| 9,987,428 B2 | 6/2018 | Tan-Malecki et al. |
| 9,999,724 B2 | 6/2018 | Cindrich et al. |
| 9,999,727 B2 | 6/2018 | O'Connor et al. |
| 10,004,832 B2 | 6/2018 | Yotsutsuji |
| 10,023,644 B2 | 7/2018 | Gromada et al. |
| 10,046,115 B2 | 8/2018 | Bokelman et al. |
| 10,058,658 B1 | 8/2018 | Voytilla |
| 10,071,196 B2 | 9/2018 | Cabiri |
| 10,071,198 B2 | 9/2018 | Cabiri et al. |
| 10,071,203 B2 | 9/2018 | Edwards et al. |
| 10,076,605 B2 | 9/2018 | Marbet et al. |
| 10,076,611 B2 | 9/2018 | Edwards et al. |
| 10,080,837 B2 | 9/2018 | Meehan et al. |
| 10,080,846 B2 | 9/2018 | Sonderegger et al. |
| 10,092,693 B2 | 10/2018 | Hanson et al. |
| 10,099,005 B2 | 10/2018 | Gao et al. |
| 10,099,023 B2 | 10/2018 | Edwards et al. |
| 10,105,489 B2 | 10/2018 | Edwards et al. |
| 10,124,112 B2 | 11/2018 | Diianni et al. |
| 10,124,113 B2 | 11/2018 | Tieck et al. |
| 10,130,758 B2 | 11/2018 | Diianni et al. |
| 10,130,763 B2 | 11/2018 | Lauchard et al. |
| 10,137,254 B2 | 11/2018 | Larsen et al. |
| 10,143,792 B2 | 12/2018 | Edwards et al. |
| 10,143,801 B2 | 12/2018 | Schabbach et al. |
| 10,149,947 B2 | 12/2018 | Bayer et al. |
| 10,155,086 B2 | 12/2018 | Sugimoto et al. |
| 10,159,785 B2 | 12/2018 | Cabiri |
| 10,159,799 B2 | 12/2018 | Kondoh et al. |
| D838,840 S | 1/2019 | Cabiri et al. |
| D839,413 S | 1/2019 | Wohlfahrt et al. |
| D839,416 S | 1/2019 | Wohlfahrt et al. |
| 10,166,336 B2 | 1/2019 | Lumme et al. |
| 10,173,001 B2 | 1/2019 | Schabbach et al. |
| 10,173,013 B2 | 1/2019 | Kaneko et al. |
| 10,179,204 B2 | 1/2019 | Cabiri |
| 10,182,969 B2 | 1/2019 | Arnott et al. |
| 10,183,116 B2 | 1/2019 | Edwards et al. |
| 10,183,117 B2 | 1/2019 | Fraunhofer et al. |
| 10,293,965 B2 | 5/2019 | Lu et al. |
| 10,314,968 B2 | 6/2019 | Bruggemann et al. |
| 10,358,495 B2 | 7/2019 | Ullman et al. |
| 10,391,245 B2 | 8/2019 | Cronenberg et al. |
| 10,413,667 B2 | 9/2019 | Henderson et al. |
| 10,426,892 B2 | 10/2019 | Stefanov |
| 10,518,041 B2 | 12/2019 | Brereton et al. |
| 10,525,193 B2 | 1/2020 | Schauderna |
| 10,532,155 B2 | 1/2020 | Schiendzielorz |
| D876,618 S | 2/2020 | Nazzaro et al. |
| 10,549,029 B2 | 2/2020 | Agard et al. |
| 10,549,044 B2 | 2/2020 | Quinn et al. |
| 10,556,064 B2 | 2/2020 | Brereton et al. |
| D877,893 S | 3/2020 | Stonecipher et al. |
| D878,555 S | 3/2020 | Farris et al. |
| D878,556 S | 3/2020 | Farris et al. |
| D878,557 S | 3/2020 | Farris et al. |
| D878,559 S | 3/2020 | Stonecipher et al. |
| D887,893 S | 3/2020 | Stonecipher et al. |
| 10,583,241 B2 | 3/2020 | Wu et al. |
| 10,583,245 B2 | 3/2020 | Mccullough et al. |
| 10,603,445 B2 | 3/2020 | Quinn et al. |
| D882,760 S | 4/2020 | Katz et al. |
| D882,761 S | 4/2020 | Cabiri et al. |
| D882,765 S | 4/2020 | Farris et al. |

(56) References Cited

U.S. PATENT DOCUMENTS

| | | |
|---|---|---|
| 10,610,640 B2 | 4/2020 | Gonnelli et al. |
| 10,617,819 B2 | 4/2020 | Cabiri et al. |
| 10,632,249 B2 | 4/2020 | Marbet et al. |
| 10,632,253 B2 | 4/2020 | Uchiyama et al. |
| 10,646,643 B2 | 5/2020 | Cabiri et al. |
| 10,661,015 B2 | 5/2020 | Rioux et al. |
| 10,668,227 B2 | 6/2020 | Caspers |
| 10,682,458 B2 | 6/2020 | Wu et al. |
| 10,695,485 B2 | 6/2020 | Nazzaro |
| 10,695,487 B2 | 6/2020 | Hanson et al. |
| 10,722,646 B2 | 7/2020 | Cole et al. |
| 10,726,701 B2 | 7/2020 | Edwards et al. |
| D894,373 S | 8/2020 | Haug et al. |
| 10,737,019 B2 | 8/2020 | Henderson et al. |
| 10,751,476 B2 | 8/2020 | Gazeley et al. |
| 10,758,683 B2 | 9/2020 | Gibson et al. |
| 10,765,801 B2 | 9/2020 | McCullough |
| 10,765,807 B2 | 9/2020 | Allis et al. |
| 10,773,024 B2 | 9/2020 | Cronenberg et al. |
| 10,780,227 B2 | 9/2020 | Young |
| 10,792,424 B2 | 10/2020 | Sasaki |
| 10,792,425 B2 | 10/2020 | Joseph et al. |
| 10,792,432 B2 | 10/2020 | Gazeley et al. |
| 10,793,624 B2 | 10/2020 | Orengo et al. |
| 10,799,630 B2 | 10/2020 | Mccullough |
| 10,799,631 B2 | 10/2020 | Barmaimon et al. |
| 10,799,644 B2 | 10/2020 | Hansen et al. |
| 10,806,854 B2 | 10/2020 | O'Connor et al. |
| 10,806,855 B2 | 10/2020 | Destefano et al. |
| 10,828,430 B2 | 11/2020 | Kondo |
| 10,842,947 B2 | 11/2020 | Helmer |
| 10,850,028 B2 | 12/2020 | Caspers |
| 10,874,792 B2 | 12/2020 | Meehan et al. |
| 10,894,128 B2 | 1/2021 | Bokelman et al. |
| 10,898,656 B2 | 1/2021 | McCaffrey et al. |
| 10,912,887 B2 | 2/2021 | Ishikawa et al. |
| 10,918,788 B2 | 2/2021 | O'Connor et al. |
| 10,918,791 B2 | 2/2021 | Edwards et al. |
| 10,926,023 B2 | 2/2021 | Falkovich |
| D914,200 S | 3/2021 | Gregory et al. |
| 10,933,188 B2 | 3/2021 | Gonnelli et al. |
| 10,933,189 B2 | 3/2021 | Bente, IV et al. |
| 10,933,192 B2 | 3/2021 | Hanson et al. |
| 10,946,136 B2 | 3/2021 | Prudden et al. |
| 10,953,157 B2 | 3/2021 | Klemm et al. |
| 10,960,134 B2 | 3/2021 | Salter et al. |
| 10,967,118 B2 | 4/2021 | Barmaimon et al. |
| 10,967,127 B2 | 4/2021 | Murakami et al. |
| 10,980,938 B2 | 4/2021 | Barmaimon et al. |
| 10,980,939 B2 | 4/2021 | Kondo et al. |
| 10,987,466 B2 | 4/2021 | Johnson et al. |
| 10,987,467 B2 | 4/2021 | Cole et al. |
| 11,000,651 B2 | 5/2021 | Anderson et al. |
| 11,033,676 B2 | 6/2021 | Dechelette et al. |
| 11,033,679 B2 | 6/2021 | Hanson et al. |
| 11,033,688 B2 | 6/2021 | Helmer et al. |
| 11,040,135 B2 | 6/2021 | Clemente et al. |
| 11,040,137 B2 | 6/2021 | Wei |
| 11,045,603 B2 | 6/2021 | McCaffrey et al. |
| 11,058,605 B2 | 7/2021 | Barmaimon et al. |
| 11,058,817 B2 | 7/2021 | Sugimoto et al. |
| 11,077,246 B2 | 8/2021 | Nekouzadeh et al. |
| 11,103,636 B2 | 8/2021 | Olivas et al. |
| 11,103,680 B2 | 8/2021 | Cole |
| 11,110,225 B2 | 9/2021 | Tan-Malecki et al. |
| 11,129,936 B2 | 9/2021 | Gibson et al. |
| 11,129,941 B2 | 9/2021 | Tan-Malecki et al. |
| 11,129,943 B2 | 9/2021 | Nazzaro et al. |
| 11,154,654 B2 | 10/2021 | Hirschel et al. |
| 11,160,931 B2 | 11/2021 | Tan-Malecki et al. |
| 11,167,082 B2 | 11/2021 | Laurence et al. |
| 11,173,244 B2 | 11/2021 | Agard et al. |
| 11,185,629 B2 | 11/2021 | Weibel et al. |
| D938,578 S | 12/2021 | Kolenda et al. |
| 11,197,954 B2 | 12/2021 | Staub et al. |
| 11,202,858 B2 | 12/2021 | Yigal et al. |
| 11,213,624 B2 | 1/2022 | McCullough et al. |
| 11,213,626 B2 | 1/2022 | Paramanandam et al. |
| 11,229,738 B2 | 1/2022 | Møller |
| 11,229,741 B2 | 1/2022 | Diianni et al. |
| 11,241,527 B2 | 2/2022 | Rabolli |
| 11,241,529 B2 | 2/2022 | Pizzochero et al. |
| 11,241,531 B2 | 2/2022 | Sasaki |
| 11,253,652 B2 | 2/2022 | Egloff et al. |
| 11,260,170 B2 | 3/2022 | Schabbach et al. |
| 11,260,171 B2 | 3/2022 | Smith |
| 11,260,172 B2 | 3/2022 | Barmaimon et al. |
| 11,263,921 B2 | 3/2022 | Edwards et al. |
| 11,266,777 B2 | 3/2022 | Gibson et al. |
| 11,266,787 B2 | 3/2022 | Dahmani et al. |
| 11,273,260 B2 | 3/2022 | Tan-Malecki et al. |
| 11,278,666 B2 | 3/2022 | Wei |
| 11,285,260 B2 | 3/2022 | Cole |
| 11,285,266 B2 | 3/2022 | Fitzgibbon et al. |
| 11,291,774 B2 | 4/2022 | Bayer et al. |
| 11,298,463 B2 | 4/2022 | Tan-Malecki et al. |
| 11,311,666 B1 | 4/2022 | West et al. |
| 11,311,670 B2 | 4/2022 | Barmaimon et al. |
| D950,713 S | 5/2022 | Bin et al. |
| D950,714 S | 5/2022 | Jeon et al. |
| D951,434 S | 5/2022 | Boyaval et al. |
| D955,564 S | 6/2022 | Boyaval et al. |
| D956,217 S | 6/2022 | Jeon et al. |
| 11,357,916 B2 | 6/2022 | McCullough et al. |
| 11,357,918 B2 | 6/2022 | Avery et al. |
| 11,364,337 B2 | 6/2022 | Cabiri et al. |
| 11,364,341 B2 | 6/2022 | Rioux et al. |
| 11,364,344 B2 | 6/2022 | Rabolli |
| 11,369,736 B2 | 6/2022 | Coiner et al. |
| 11,383,026 B2 | 7/2022 | Russo |
| 11,383,038 B2 | 7/2022 | Nazzaro et al. |
| 11,383,047 B2 | 7/2022 | Gibson et al. |
| 11,389,598 B2 | 7/2022 | Yigal et al. |
| 11,400,215 B2 | 8/2022 | Cowe et al. |
| 11,400,226 B2 | 8/2022 | Yigal et al. |
| 11,406,565 B2 | 8/2022 | Arnott et al. |
| 11,413,393 B2 | 8/2022 | Bourelle et al. |
| 11,426,520 B2 | 8/2022 | Edwards et al. |
| 11,439,748 B2 | 9/2022 | Giambattista et al. |
| 11,439,759 B2 | 9/2022 | Verlaak et al. |
| 11,439,767 B2 | 9/2022 | Booth et al. |
| 11,452,473 B2 | 9/2022 | Zhang et al. |
| D967,397 S | 10/2022 | Chen |
| 11,458,281 B2 | 10/2022 | Horvath et al. |
| 11,471,593 B2 | 10/2022 | Barmaimon et al. |
| 11,484,644 B2 | 11/2022 | O'Connor et al. |
| 11,484,656 B2 | 11/2022 | Hagino |
| 11,490,831 B2 | 11/2022 | Limaye et al. |
| 11,517,663 B2 | 12/2022 | McCullough et al. |
| 11,517,664 B2 | 12/2022 | Barmaimon et al. |
| 11,517,674 B2 | 12/2022 | Edwards et al. |
| 11,524,112 B2 | 12/2022 | Day et al. |
| 11,541,167 B2 | 1/2023 | Richards et al. |
| 11,541,183 B2 | 1/2023 | Hering et al. |
| 11,547,801 B2 * | 1/2023 | Grygus ............... A61M 5/3202 |
| 11,554,213 B2 | 1/2023 | Stefanov et al. |
| 11,590,277 B2 | 2/2023 | Stonecipher et al. |
| 11,590,279 B2 | 2/2023 | Barmaimon et al. |
| 11,590,286 B2 | 2/2023 | Edwards et al. |
| 11,590,292 B2 | 2/2023 | Mayle, Jr. et al. |
| 11,596,733 B2 | 3/2023 | Yodfat et al. |
| 11,607,505 B1 | 3/2023 | West |
| D982,742 S | 4/2023 | Cerqueira et al. |
| 11,617,833 B2 | 4/2023 | Rioux et al. |
| 11,617,837 B2 | 4/2023 | Olivas et al. |
| D986,288 S | 5/2023 | Zhang |
| 11,642,470 B2 | 5/2023 | Bar-El et al. |
| 11,648,345 B2 | 5/2023 | Nemoto et al. |
| 11,684,712 B2 | 6/2023 | Smith et al. |
| 11,766,519 B2 | 9/2023 | Dutta Ray et al. |
| 11,813,428 B2 | 11/2023 | Barraud et al. |
| 11,819,663 B2 | 11/2023 | Marcoz et al. |
| 11,857,757 B2 | 1/2024 | Fridez et al. |
| 11,883,633 B2 | 1/2024 | Slate et al. |

(56) References Cited

U.S. PATENT DOCUMENTS

| | | |
|---|---|---|
| 11,992,662 B2 | 5/2024 | Dahmani et al. |
| 2001/0025168 A1 | 9/2001 | Gross et al. |
| 2002/0043951 A1 | 4/2002 | Moberg |
| 2002/0123719 A1 | 9/2002 | Lavi et al. |
| 2002/0161332 A1 | 10/2002 | Ramey |
| 2003/0009133 A1 | 1/2003 | Ramey |
| 2003/0055395 A1 | 3/2003 | Manera |
| 2003/0083686 A1 | 5/2003 | Freeman et al. |
| 2003/0097092 A1 | 5/2003 | Flaherty |
| 2003/0105430 A1 | 6/2003 | Lavi et al. |
| 2003/0138347 A1 | 7/2003 | Lin |
| 2004/0015134 A1 | 1/2004 | Lavi et al. |
| 2004/0020558 A1 | 2/2004 | Stewart et al. |
| 2004/0030285 A1 | 2/2004 | Lavi et al. |
| 2004/0068176 A1 | 4/2004 | Kuth |
| 2004/0069044 A1 | 4/2004 | Lavi et al. |
| 2004/0092873 A1 | 5/2004 | Moberg |
| 2005/0065472 A1 | 3/2005 | Cindrich et al. |
| 2005/0165363 A1 | 7/2005 | Judson et al. |
| 2005/0197650 A1 | 9/2005 | Sugimoto et al. |
| 2005/0212222 A1 | 9/2005 | Tachikawa et al. |
| 2006/0102178 A1 | 5/2006 | Feiner et al. |
| 2006/0200073 A1 | 9/2006 | Radmer et al. |
| 2006/0282040 A1 | 12/2006 | Toman et al. |
| 2007/0021715 A1 | 1/2007 | Kohlbrenner et al. |
| 2007/0021733 A1 | 1/2007 | Hansen et al. |
| 2007/0088291 A1 | 4/2007 | Weilbacher |
| 2007/0112326 A1 | 5/2007 | Bosshard et al. |
| 2007/0135767 A1 | 6/2007 | Gillespie, III et al. |
| 2007/0178776 A1 | 8/2007 | Etter et al. |
| 2007/0233001 A1* | 10/2007 | Burroughs ............ A61M 5/008 604/131 |
| 2007/0299402 A1 | 12/2007 | Ishii et al. |
| 2008/0051711 A1 | 2/2008 | Mounce et al. |
| 2008/0132843 A1 | 6/2008 | Sharifi |
| 2008/0172988 A1 | 7/2008 | Hwang |
| 2008/0221523 A1 | 9/2008 | Moberg et al. |
| 2008/0234628 A1 | 9/2008 | Dent et al. |
| 2008/0269687 A1 | 10/2008 | Chong et al. |
| 2008/0281297 A1 | 11/2008 | Pesach et al. |
| 2009/0048563 A1 | 2/2009 | Ethelfeld et al. |
| 2009/0076383 A1 | 3/2009 | Toews et al. |
| 2009/0093793 A1 | 4/2009 | Gross et al. |
| 2009/0143741 A1 | 6/2009 | Burn |
| 2009/0163860 A1 | 6/2009 | Patrick et al. |
| 2009/0163874 A1 | 6/2009 | Krag et al. |
| 2009/0236253 A1 | 9/2009 | Merckle et al. |
| 2009/0247982 A1 | 10/2009 | Krulevitch et al. |
| 2009/0254046 A1 | 10/2009 | Hetherington |
| 2009/0288977 A1 | 11/2009 | Vanderbush et al. |
| 2010/0036319 A1 | 2/2010 | Drake et al. |
| 2010/0049125 A1 | 2/2010 | James et al. |
| 2010/0049128 A1 | 2/2010 | McKenzie et al. |
| 2010/0152674 A1 | 6/2010 | Kavazov et al. |
| 2010/0198187 A1 | 8/2010 | Yodfat et al. |
| 2010/0274200 A1 | 10/2010 | Nielsen |
| 2011/0009814 A1 | 1/2011 | Tsoukalis |
| 2011/0021993 A1 | 1/2011 | Bar-Haim et al. |
| 2011/0054285 A1 | 3/2011 | Searle et al. |
| 2011/0105872 A1 | 5/2011 | Chickering, III et al. |
| 2011/0137255 A1 | 6/2011 | Nielsen et al. |
| 2011/0137257 A1 | 6/2011 | Gyrn et al. |
| 2011/0152779 A1 | 6/2011 | Panotopoulos |
| 2011/0224616 A1 | 9/2011 | Slate et al. |
| 2011/0270220 A1 | 11/2011 | Genosar |
| 2012/0022499 A1 | 1/2012 | Anderson et al. |
| 2012/0035546 A1 | 2/2012 | Cabiri |
| 2012/0051967 A1 | 3/2012 | Murphy et al. |
| 2012/0071829 A1 | 3/2012 | Edwards et al. |
| 2012/0071837 A1 | 3/2012 | O'Connor et al. |
| 2012/0095409 A1* | 4/2012 | Lanin ................. A61M 5/3234 604/201 |
| 2012/0116212 A1 | 5/2012 | Bral |
| 2012/0123387 A1 | 5/2012 | Gonzalez et al. |
| 2012/0130318 A1 | 5/2012 | Young |
| 2012/0211946 A1 | 8/2012 | Halili et al. |
| 2012/0238962 A1 | 9/2012 | Chin et al. |
| 2012/0252709 A1 | 10/2012 | Felts et al. |
| 2012/0253314 A1 | 10/2012 | Harish et al. |
| 2012/0265127 A1 | 10/2012 | Buri et al. |
| 2012/0310173 A1 | 12/2012 | Sonderegger |
| 2012/0310175 A1 | 12/2012 | Vedrine et al. |
| 2012/0323183 A1 | 12/2012 | Peterson et al. |
| 2012/0330235 A1 | 12/2012 | Moga et al. |
| 2013/0006195 A1 | 1/2013 | Sonderegger et al. |
| 2013/0008137 A1 | 1/2013 | Py |
| 2013/0012872 A1 | 1/2013 | Gross et al. |
| 2013/0012874 A1 | 1/2013 | Gross et al. |
| 2013/0012875 A1 | 1/2013 | Gross et al. |
| 2013/0053786 A1 | 2/2013 | Maeda et al. |
| 2013/0066274 A1 | 3/2013 | O'Connor et al. |
| 2013/0079747 A1 | 3/2013 | Gross et al. |
| 2013/0090605 A1 | 4/2013 | O'Connor et al. |
| 2013/0172819 A1 | 7/2013 | Iio et al. |
| 2013/0178826 A1 | 7/2013 | Li |
| 2013/0180618 A1 | 7/2013 | Py |
| 2013/0204224 A1 | 8/2013 | Mueller-Pathle et al. |
| 2013/0211344 A1 | 8/2013 | Rodriguez et al. |
| 2013/0211374 A1 | 8/2013 | Hetherington |
| 2013/0218089 A1 | 8/2013 | Davies et al. |
| 2013/0218092 A1 | 8/2013 | Davies et al. |
| 2013/0237916 A1 | 9/2013 | Hanson et al. |
| 2013/0245604 A1 | 9/2013 | Kouyoumjian et al. |
| 2013/0281932 A1 | 10/2013 | Harish et al. |
| 2013/0310757 A1 | 11/2013 | Brereton et al. |
| 2013/0316110 A1 | 11/2013 | Sudo |
| 2013/0317427 A1 | 11/2013 | Brereton et al. |
| 2013/0317430 A1 | 11/2013 | Brereton et al. |
| 2013/0338584 A1 | 12/2013 | Mounce et al. |
| 2013/0345626 A1 | 12/2013 | Tennican |
| 2014/0005596 A1 | 1/2014 | Schuster |
| 2014/0008366 A1 | 1/2014 | Genosar |
| 2014/0214000 A1 | 1/2014 | Moia et al. |
| 2014/0039405 A1 | 2/2014 | Konandreas et al. |
| 2014/0052055 A1 | 2/2014 | Yodfat et al. |
| 2014/0058349 A1 | 2/2014 | Bazargan et al. |
| 2014/0074062 A1 | 3/2014 | Caffey et al. |
| 2014/0083517 A1 | 3/2014 | Moia et al. |
| 2014/0088508 A1 | 3/2014 | Ryan et al. |
| 2014/0088553 A1 | 3/2014 | Hetherington |
| 2014/0128815 A1 | 5/2014 | Cabiri et al. |
| 2014/0128840 A1 | 5/2014 | Rao et al. |
| 2014/0142507 A1 | 5/2014 | Armes |
| 2014/0148760 A1 | 5/2014 | Ishikawa et al. |
| 2014/0148784 A1 | 5/2014 | Anderson et al. |
| 2014/0171871 A1 | 6/2014 | Mathews et al. |
| 2014/0171872 A1 | 6/2014 | Mathews et al. |
| 2014/0200510 A1 | 7/2014 | Agard et al. |
| 2014/0207075 A1 | 7/2014 | Yotsutsuji |
| 2014/0213975 A1 | 7/2014 | Clemente et al. |
| 2014/0221930 A1 | 8/2014 | Kuster et al. |
| 2014/0236086 A1 | 8/2014 | Levesque et al. |
| 2014/0236096 A1 | 8/2014 | Helmer et al. |
| 2014/0238542 A1 | 8/2014 | Kvale |
| 2014/0243749 A1 | 8/2014 | Edwards et al. |
| 2014/0288511 A1 | 9/2014 | Tan-Malecki et al. |
| 2014/0296787 A1 | 10/2014 | Agard et al. |
| 2014/0296824 A1 | 10/2014 | Edwards et al. |
| 2014/0316376 A1 | 10/2014 | Wall |
| 2014/0319778 A1 | 10/2014 | Kawasaki et al. |
| 2014/0336578 A1 | 11/2014 | Brereton et al. |
| 2014/0339777 A1 | 11/2014 | Nakano et al. |
| 2015/0011973 A1 | 1/2015 | Edwards et al. |
| 2015/0057613 A1 | 2/2015 | Clemente et al. |
| 2015/0080800 A1 | 3/2015 | Cronenberg |
| 2015/0088077 A1 | 3/2015 | Kemp et al. |
| 2015/0088092 A1 | 3/2015 | Holm et al. |
| 2015/0119674 A1 | 4/2015 | Fischell et al. |
| 2015/0126926 A1 | 5/2015 | Giambattista et al. |
| 2015/0144793 A1 | 5/2015 | Whalley et al. |
| 2015/0148751 A1 | 5/2015 | Yotsutsuji |
| 2015/0157786 A1 | 6/2015 | Sonderegger et al. |
| 2015/0157804 A1 | 6/2015 | Baba et al. |
| 2015/0174323 A1 | 6/2015 | Edwards et al. |

(56) References Cited

U.S. PATENT DOCUMENTS

| | | |
|---|---|---|
| 2015/0174326 A1 | 6/2015 | Bokelman et al. |
| 2015/0190588 A1 | 7/2015 | Hanson et al. |
| 2015/0202367 A1 | 7/2015 | Plaschkes et al. |
| 2015/0203612 A1 | 7/2015 | Minagawa |
| 2015/0209505 A1 | 7/2015 | Hanson et al. |
| 2015/0209519 A1 | 7/2015 | Mernøe |
| 2015/0217045 A1 | 8/2015 | Bente, IV et al. |
| 2015/0231336 A1 | 8/2015 | Edwards et al. |
| 2015/0265767 A1 | 9/2015 | Vazquez et al. |
| 2015/0265768 A1 | 9/2015 | Vazquez et al. |
| 2015/0273151 A1 | 10/2015 | McLoughlin et al. |
| 2015/0273155 A1 | 10/2015 | Kaneko et al. |
| 2015/0290392 A1 | 10/2015 | Henderson et al. |
| 2015/0290394 A1 | 10/2015 | Murakami et al. |
| 2015/0297827 A1 | 10/2015 | Hanson et al. |
| 2015/0306306 A1 | 10/2015 | Gonnelli et al. |
| 2015/0306307 A1 | 10/2015 | Cole et al. |
| 2015/0359965 A1 | 12/2015 | O'Connor et al. |
| 2015/0374912 A1 | 12/2015 | Sugimoto et al. |
| 2016/0008542 A1 | 1/2016 | Hirschel et al. |
| 2016/0015907 A1 | 1/2016 | Edwards et al. |
| 2016/0022909 A1 | 1/2016 | Edwards et al. |
| 2016/0022918 A1 | 1/2016 | Gunzel |
| 2016/0030665 A1 | 2/2016 | Cabiri |
| 2016/0045670 A1 | 2/2016 | Edwards et al. |
| 2016/0045673 A1 | 2/2016 | Bayer et al. |
| 2016/0058941 A1 | 3/2016 | Wu et al. |
| 2016/0058945 A1 | 3/2016 | Piscitelli |
| 2016/0058949 A1 | 3/2016 | Bayer et al. |
| 2016/0067417 A1 | 3/2016 | Bayer et al. |
| 2016/0082182 A1 | 3/2016 | Gregory et al. |
| 2016/0082189 A1 | 3/2016 | Anderson et al. |
| 2016/0082193 A1 | 3/2016 | Laubach et al. |
| 2016/0089056 A1 | 3/2016 | Limaye et al. |
| 2016/0101239 A1 | 4/2016 | Ishida et al. |
| 2016/0106912 A1 | 4/2016 | Gross et al. |
| 2016/0106923 A1 | 4/2016 | Brereton et al. |
| 2016/0121056 A1 | 5/2016 | Edwards et al. |
| 2016/0129194 A1 | 5/2016 | Brereton et al. |
| 2016/0129202 A1 | 5/2016 | Carrel et al. |
| 2016/0158435 A1 | 6/2016 | Wu et al. |
| 2016/0158463 A1 | 6/2016 | Kamen et al. |
| 2016/0175515 A1 | 6/2016 | McCullough |
| 2016/0175527 A1 | 6/2016 | McCullough |
| 2016/0184514 A1 | 6/2016 | Kamen et al. |
| 2016/0184521 A1 | 6/2016 | Edwards et al. |
| 2016/0184535 A1 | 6/2016 | Edwards et al. |
| 2016/0193405 A1 | 7/2016 | Schabbach et al. |
| 2016/0213837 A1 | 7/2016 | Schabbach et al. |
| 2016/0213838 A1 | 7/2016 | Schabbach et al. |
| 2016/0213840 A1 | 7/2016 | Schabbach et al. |
| 2016/0228644 A1 | 8/2016 | Cabiri |
| 2016/0235916 A1 | 8/2016 | Edwards et al. |
| 2016/0243308 A1 | 8/2016 | Giraud et al. |
| 2016/0243311 A1 | 8/2016 | Fournier et al. |
| 2016/0243318 A1 | 8/2016 | Despa et al. |
| 2016/0250414 A1 | 9/2016 | Edwards et al. |
| 2016/0262984 A1 | 9/2016 | Arnott et al. |
| 2016/0263324 A1 | 9/2016 | Shaanan et al. |
| 2016/0271323 A1 | 9/2016 | Brüggemann et al. |
| 2016/0279330 A1* | 9/2016 | Schabbach ............. A61M 5/20 |
| 2016/0287800 A1 | 10/2016 | Nakano et al. |
| 2016/0317736 A1 | 11/2016 | Schabbach et al. |
| 2016/0317737 A1 | 11/2016 | Schabbach et al. |
| 2016/0325044 A1 | 11/2016 | Tschirren et al. |
| 2016/0354553 A1 | 12/2016 | Anderson et al. |
| 2016/0367752 A1 | 12/2016 | Cindrich et al. |
| 2017/0014576 A1 | 1/2017 | Abe et al. |
| 2017/0020557 A1 | 1/2017 | Onuma |
| 2017/0021096 A1 | 1/2017 | Cole et al. |
| 2017/0021103 A1 | 1/2017 | Mosebach et al. |
| 2017/0021107 A1 | 1/2017 | Kaneko et al. |
| 2017/0021108 A1 | 1/2017 | Swal et al. |
| 2017/0021137 A1 | 1/2017 | Cole |
| 2017/0028132 A1 | 2/2017 | Cronenberg et al. |
| 2017/0035957 A1 | 2/2017 | Edwards et al. |
| 2017/0035961 A1 | 2/2017 | Cabiri |
| 2017/0037212 A1 | 2/2017 | Minagawa |
| 2017/0043101 A1 | 2/2017 | Cole et al. |
| 2017/0049954 A1 | 2/2017 | Edwards et al. |
| 2017/0049958 A1 | 2/2017 | Cronenberg et al. |
| 2017/0049965 A1 | 2/2017 | Baker et al. |
| 2017/0056582 A1 | 3/2017 | Niklaus |
| 2017/0080149 A1 | 3/2017 | O'Connor et al. |
| 2017/0092101 A1 | 3/2017 | Edwards et al. |
| 2017/0095614 A1 | 4/2017 | Sonderegger et al. |
| 2017/0098058 A1 | 4/2017 | McCullough et al. |
| 2017/0103186 A1 | 4/2017 | McCullough et al. |
| 2017/0119959 A1 | 5/2017 | Cole et al. |
| 2017/0119969 A1 | 5/2017 | McCullough et al. |
| 2017/0124284 A1 | 5/2017 | McCullough et al. |
| 2017/0124285 A1 | 5/2017 | McCullough et al. |
| 2017/0128665 A1 | 5/2017 | Mathews et al. |
| 2017/0143908 A1 | 5/2017 | Eggert et al. |
| 2017/0165418 A1 | 6/2017 | Bainton et al. |
| 2017/0173266 A1 | 6/2017 | Ashmead et al. |
| 2017/0173267 A1 | 6/2017 | Ashmead et al. |
| 2017/0182242 A1 | 6/2017 | Galitz et al. |
| 2017/0182243 A1 | 6/2017 | Cole et al. |
| 2017/0189609 A1 | 7/2017 | Wei |
| 2017/0189610 A1 | 7/2017 | Gonnelli et al. |
| 2017/0197029 A1 | 7/2017 | Cindrich et al. |
| 2017/0197036 A1 | 7/2017 | Brereton et al. |
| 2017/0203033 A1 | 7/2017 | Horvath et al. |
| 2017/0203043 A1 | 7/2017 | Rusch et al. |
| 2017/0203046 A1 | 7/2017 | Larose |
| 2017/0209648 A1 | 7/2017 | Butts et al. |
| 2017/0216526 A1 | 8/2017 | Brereton et al. |
| 2017/0224915 A1 | 8/2017 | Destefano et al. |
| 2017/0232202 A1 | 8/2017 | Yotsutsuji |
| 2017/0239414 A1 | 8/2017 | Barmaimon et al. |
| 2017/0246384 A1 | 8/2017 | Pizzochero et al. |
| 2017/0246397 A1 | 8/2017 | Brereton et al. |
| 2017/0246398 A1 | 8/2017 | Brereton et al. |
| 2017/0252508 A1 | 9/2017 | Schiendzielorz |
| 2017/0252509 A1 | 9/2017 | Caspers |
| 2017/0252510 A1 | 9/2017 | Sonderegger et al. |
| 2017/0258987 A1 | 9/2017 | Caspers |
| 2017/0258994 A1 | 9/2017 | Schiendzielorz |
| 2017/0259014 A1 | 9/2017 | Nessel |
| 2017/0259015 A1 | 9/2017 | Caspers |
| 2017/0266386 A1 | 9/2017 | Kaneko |
| 2017/0266390 A1 | 9/2017 | Baba et al. |
| 2017/0281854 A1 | 10/2017 | Mathews et al. |
| 2017/0281859 A1 | 10/2017 | Agard et al. |
| 2017/0290975 A1 | 10/2017 | Barmaimon et al. |
| 2017/0290977 A1 | 10/2017 | Schauderna |
| 2017/0290981 A1 | 10/2017 | Hoeholt et al. |
| 2017/0290982 A1 | 10/2017 | Edwards et al. |
| 2017/0296741 A1 | 10/2017 | Gregory |
| 2017/0296752 A1 | 10/2017 | Masuyama et al. |
| 2017/0296756 A1 | 10/2017 | Giraud et al. |
| 2017/0304539 A1 | 10/2017 | Ishikawa et al. |
| 2017/0312433 A1 | 11/2017 | Edwards et al. |
| 2017/0319790 A1* | 11/2017 | Andersen ............. A61M 5/31561 |
| 2017/0340827 A1 | 11/2017 | Nazzaro et al. |
| 2017/0340837 A1 | 11/2017 | Nazzaro et al. |
| 2017/0348479 A1 | 12/2017 | Choate et al. |
| 2017/0354781 A1 | 12/2017 | Cronenberg et al. |
| 2017/0354782 A1 | 12/2017 | Quinn et al. |
| 2017/0354783 A1 | 12/2017 | Gazeley et al. |
| 2017/0354785 A1 | 12/2017 | Gazeley et al. |
| 2017/0354788 A1 | 12/2017 | Quinn et al. |
| 2017/0361015 A1 | 12/2017 | McCullough |
| 2017/0361016 A1 | 12/2017 | Levesque et al. |
| 2017/0368260 A1 | 12/2017 | Mccullough et al. |
| 2017/0368264 A1 | 12/2017 | Fournier et al. |
| 2017/0368269 A1 | 12/2017 | Kondo |
| 2018/0008769 A1 | 1/2018 | O'Connor et al. |
| 2018/0008774 A1 | 1/2018 | Edwards et al. |
| 2018/0015222 A1 | 1/2018 | Sasaki |
| 2018/0021508 A1 | 1/2018 | Destefano et al. |
| 2018/0028747 A1 | 2/2018 | Hanson et al. |
| 2018/0033286 A1 | 2/2018 | Edwards et al. |

(56) References Cited

U.S. PATENT DOCUMENTS

| | | |
|---|---|---|
| 2018/0036489 A1 | 2/2018 | Nakano et al. |
| 2018/0036490 A1 | 2/2018 | Minagawa |
| 2018/0043091 A1 | 2/2018 | Agard et al. |
| 2018/0043102 A1 | 2/2018 | Cojocariu et al. |
| 2018/0055995 A1 | 3/2018 | Hanson et al. |
| 2018/0056009 A1 | 3/2018 | Filman et al. |
| 2018/0079119 A1 | 3/2018 | Morris et al. |
| 2018/0085517 A1 | 3/2018 | Laurence et al. |
| 2018/0085521 A1 | 3/2018 | Allis et al. |
| 2018/0102066 A1 | 4/2018 | Edwards et al. |
| 2018/0103870 A1 | 4/2018 | Limaye et al. |
| 2018/0117251 A1 | 5/2018 | Rioux et al. |
| 2018/0126082 A1 | 5/2018 | Edwards et al. |
| 2018/0154079 A1 | 6/2018 | Anderson et al. |
| 2018/0177951 A1 | 6/2018 | Sakashita |
| 2018/0185571 A1 | 7/2018 | Clemente et al. |
| 2018/0185579 A1 | 7/2018 | Joseph et al. |
| 2018/0193557 A1 | 7/2018 | Johnson et al. |
| 2018/0200425 A1 | 7/2018 | Kondo et al. |
| 2018/0200445 A1 | 7/2018 | Brereton et al. |
| 2018/0207308 A1 | 7/2018 | Okihara |
| 2018/0207358 A1 | 7/2018 | Uchiyama et al. |
| 2018/0214631 A1 | 8/2018 | Amirouche |
| 2018/0221569 A1 | 8/2018 | Gonnelli et al. |
| 2018/0221573 A1 | 8/2018 | Hanson et al. |
| 2018/0228966 A1 | 8/2018 | Barmaimon et al. |
| 2018/0236173 A1 | 8/2018 | McCaffrey et al. |
| 2018/0243503 A1 | 8/2018 | Gonnelli et al. |
| 2018/0250472 A1 | 9/2018 | Anderson et al. |
| 2018/0256815 A1 | 9/2018 | Nazzaro |
| 2018/0256823 A1 | 9/2018 | Nazzaro et al. |
| 2018/0264193 A1 | 9/2018 | O'Connor et al. |
| 2018/0266565 A1 | 9/2018 | Minagawa |
| 2018/0272058 A1 | 9/2018 | Pizzochero et al. |
| 2018/0272059 A1 | 9/2018 | Marbet et al. |
| 2018/0272072 A1 | 9/2018 | Radmer et al. |
| 2018/0280607 A1 | 10/2018 | Richards et al. |
| 2018/0289897 A1 | 10/2018 | Kaneko et al. |
| 2018/0333532 A1 | 11/2018 | Wei |
| 2018/0344939 A1 | 12/2018 | Sakashita |
| 2018/0344940 A1 | 12/2018 | Voytilla |
| 2018/0353682 A1 | 12/2018 | Laurence et al. |
| 2018/0353686 A1 | 12/2018 | Ishikawa et al. |
| 2018/0353687 A1 | 12/2018 | Ishikawa et al. |
| 2018/0353688 A1 | 12/2018 | Ishikawa et al. |
| 2018/0353689 A1 | 12/2018 | Ishikawa et al. |
| 2018/0353690 A1 | 12/2018 | Ishikawa et al. |
| 2018/0353691 A1 | 12/2018 | Ishikawa et al. |
| 2018/0353696 A1 | 12/2018 | Helmer et al. |
| 2018/0369489 A1 | 12/2018 | Nakano et al. |
| 2018/0369506 A1 | 12/2018 | Edwards et al. |
| 2019/0009019 A1 | 1/2019 | Shor et al. |
| 2019/0009027 A1 | 1/2019 | Edwards et al. |
| 2019/0015583 A1 | 1/2019 | Prudden et al. |
| 2019/0015584 A1 | 1/2019 | Meehan et al. |
| 2019/0022305 A1 | 1/2019 | Møller |
| 2019/0022306 A1 | 1/2019 | Gibson et al. |
| 2019/0022312 A1 | 1/2019 | Barmaimon et al. |
| 2019/0022313 A1 | 1/2019 | Barmaimon et al. |
| 2019/0022317 A1 | 1/2019 | Uddin et al. |
| 2019/0035500 A1 | 1/2019 | Saint et al. |
| 2019/0046727 A1 | 2/2019 | Aneas |
| 2019/0083702 A1 | 3/2019 | Nekouzadeh et al. |
| 2019/0143044 A1 | 5/2019 | Paramanandam et al. |
| 2019/0175840 A1 | 6/2019 | Schabbach et al. |
| 2019/0240417 A1* | 8/2019 | Hostettler ............ A61M 5/3232 |
| 2019/0358399 A1 | 11/2019 | Edwards et al. |
| 2019/0374707 A1 | 12/2019 | Damestani et al. |
| 2019/0381238 A1 | 12/2019 | Stonecipher et al. |
| 2020/0009316 A1 | 1/2020 | Cabiri et al. |
| 2020/0061286 A1 | 2/2020 | Giambattista et al. |
| 2020/0078513 A1 | 3/2020 | Wei |
| 2020/0086051 A1 | 3/2020 | Grygus et al. |
| 2020/0114080 A1 | 4/2020 | Barmaimon et al. |
| 2020/0147309 A1 | 5/2020 | Quinn et al. |
| 2020/0155759 A1 | 5/2020 | Hanson et al. |
| 2020/0164155 A1 | 5/2020 | Mojarrad et al. |
| 2020/0171236 A1 | 6/2020 | McCullough et al. |
| 2020/0188580 A1 | 6/2020 | Gregory et al. |
| 2020/0188581 A1 | 6/2020 | Diianni et al. |
| 2020/0197621 A1 | 6/2020 | Quinn et al. |
| 2020/0206429 A1 | 7/2020 | Hering et al. |
| 2020/0215273 A1 | 7/2020 | Gibson et al. |
| 2020/0230323 A1 | 7/2020 | Tan-Malecki et al. |
| 2020/0238006 A1 | 7/2020 | Groszmann et al. |
| 2020/0253525 A1 | 8/2020 | Zhang et al. |
| 2020/0254172 A1 | 8/2020 | Forster et al. |
| 2020/0254181 A1 | 8/2020 | Mosebach et al. |
| 2020/0261643 A1 | 8/2020 | Boyaval et al. |
| 2020/0261648 A1 | 8/2020 | Groszmann et al. |
| 2020/0261652 A1 | 8/2020 | Cowe et al. |
| 2020/0268969 A1 | 8/2020 | McCullough et al. |
| 2020/0297927 A1 | 9/2020 | Conrath et al. |
| 2020/0316290 A1 | 10/2020 | Bourelle et al. |
| 2020/0316291 A1 | 10/2020 | Gibson et al. |
| 2020/0330701 A1 | 10/2020 | Cole et al. |
| 2020/0345943 A1 | 11/2020 | Gazeley et al. |
| 2020/0353160 A1 | 11/2020 | McCullough |
| 2020/0353169 A1 | 11/2020 | McCullough et al. |
| 2020/0353180 A1 | 11/2020 | Edwards et al. |
| 2020/0360612 A1 | 11/2020 | Gazeley et al. |
| 2020/0368447 A1 | 11/2020 | Yigal et al. |
| 2020/0369760 A1 | 11/2020 | Liu et al. |
| 2020/0384207 A1 | 12/2020 | Egesborg et al. |
| 2020/0397995 A1 | 12/2020 | Cronenberg et al. |
| 2020/0397997 A1 | 12/2020 | Hansen et al. |
| 2020/0405948 A1 | 12/2020 | Barmaimon et al. |
| 2020/0405949 A1 | 12/2020 | Yigal et al. |
| 2020/0405950 A1 | 12/2020 | Burren et al. |
| 2020/0405951 A1 | 12/2020 | Burren et al. |
| 2020/0405952 A1 | 12/2020 | Rytz et al. |
| 2021/0003582 A1 | 1/2021 | Kang et al. |
| 2021/0015996 A1 | 1/2021 | Winheim et al. |
| 2021/0016007 A1 | 1/2021 | Baker et al. |
| 2021/0030963 A1 | 2/2021 | Dasbach et al. |
| 2021/0046182 A1 | 2/2021 | Kleppe et al. |
| 2021/0046244 A1 | 2/2021 | O'Connor et al. |
| 2021/0060255 A1 | 3/2021 | Mathews et al. |
| 2021/0069410 A1 | 3/2021 | Destefano et al. |
| 2021/0077725 A1 | 3/2021 | Tschirren et al. |
| 2021/0100955 A1 | 4/2021 | Stettler et al. |
| 2021/0100959 A1 | 4/2021 | McCaffrey et al. |
| 2021/0100961 A1 | 4/2021 | Brereton et al. |
| 2021/0138147 A1 | 5/2021 | Falkovich |
| 2021/0138157 A1 | 5/2021 | Bar-El et al. |
| 2021/0154407 A1 | 5/2021 | Hirschel et al. |
| 2021/0162126 A1 | 6/2021 | Barkhuff et al. |
| 2021/0178057 A1 | 6/2021 | Cronenberg et al. |
| 2021/0178060 A1 | 6/2021 | Salter et al. |
| 2021/0178073 A1 | 6/2021 | Goldin et al. |
| 2021/0178074 A1 | 6/2021 | Anderson et al. |
| 2021/0196892 A1 | 7/2021 | Dasbach et al. |
| 2021/0213194 A1 | 7/2021 | Cole et al. |
| 2021/0213206 A1 | 7/2021 | Brereton et al. |
| 2021/0220552 A1 | 7/2021 | Barmaimon et al. |
| 2021/0244894 A1 | 8/2021 | Edwards et al. |
| 2021/0252146 A1 | 8/2021 | Cao et al. |
| 2021/0338938 A1 | 11/2021 | Harrison et al. |
| 2021/0353861 A1 | 11/2021 | Rose et al. |
| 2021/0353911 A1 | 11/2021 | Cole |
| 2021/0369952 A1 | 12/2021 | Sasaki |
| 2021/0369957 A1 | 12/2021 | Wieser et al. |
| 2021/0393871 A1 | 12/2021 | Streit et al. |
| 2021/0393873 A1 | 12/2021 | Streit et al. |
| 2021/0402083 A1 | 12/2021 | Gibson et al. |
| 2022/0008652 A1 | 1/2022 | Nekouzadeh et al. |
| 2022/0016347 A1 | 1/2022 | Le Masne et al. |
| 2022/0023544 A1 | 1/2022 | Anderson et al. |
| 2022/0031940 A1 | 2/2022 | Hulliger et al. |
| 2022/0054741 A1 | 2/2022 | Laurence et al. |
| 2022/0080108 A1 | 3/2022 | Pizzochero et al. |
| 2022/0080125 A1 | 3/2022 | Bar-El et al. |
| 2022/0105275 A1 | 4/2022 | Jiang |
| 2022/0133993 A1 | 5/2022 | Smith |

(56) References Cited

U.S. PATENT DOCUMENTS

| | | |
|---|---|---|
| 2022/0152296 A1 | 5/2022 | Wei |
| 2022/0152308 A1 | 5/2022 | Tan-Malecki et al. |
| 2022/0160960 A1 | 5/2022 | Scott et al. |
| 2022/0160964 A1 | 5/2022 | Besson |
| 2022/0168501 A1 | 6/2022 | Cole |
| 2022/0176033 A1 | 6/2022 | Schabbach et al. |
| 2022/0184316 A1 | 6/2022 | Bayer et al. |
| 2022/0184318 A1 | 6/2022 | Rahbari et al. |
| 2022/0193343 A1 | 6/2022 | Burgess et al. |
| 2022/0203032 A1 | 6/2022 | Halbig et al. |
| 2022/0211938 A1 | 7/2022 | Diianni et al. |
| 2022/0218900 A1 | 7/2022 | Gibson et al. |
| 2022/0233775 A1 | 7/2022 | Hassan |
| 2022/0241497 A1 | 8/2022 | Burren et al. |
| 2022/0257862 A1 | 8/2022 | McCullough et al. |
| 2022/0257864 A1 | 8/2022 | Paramanandam et al. |
| 2022/0273866 A1 | 9/2022 | Cabiri et al. |
| 2022/0273878 A1 | 9/2022 | McCullough et al. |
| 2022/0280385 A1 | 9/2022 | Converse et al. |
| 2022/0288314 A1 | 9/2022 | Rioux et al. |
| 2022/0313902 A1 | 10/2022 | Gonnelli et al. |
| 2022/0313925 A1 | 10/2022 | Clasen |
| 2022/0318455 A1 | 10/2022 | Kenyon |
| 2022/0339348 A1 | 10/2022 | Othel-Jacobsen |
| 2022/0362458 A1 | 11/2022 | Schrul et al. |
| 2022/0370715 A1 | 11/2022 | Vatelmacher et al. |
| 2022/0387705 A1 | 12/2022 | Bourelle et al. |
| 2022/0401642 A1 | 12/2022 | Giambattista et al. |
| 2022/0401657 A1 | 12/2022 | Krulevitch et al. |
| 2023/0038182 A1 | 2/2023 | Kunaparaju et al. |
| 2023/0074484 A1 | 3/2023 | Zoda et al. |
| 2023/0076855 A1 | 3/2023 | Edwards et al. |
| 2023/0090486 A1 | 3/2023 | Stefanov et al. |
| 2023/0096391 A1 | 3/2023 | Chen et al. |
| 2023/0101280 A1 | 3/2023 | Barmaimon et al. |
| 2023/0105585 A1 | 4/2023 | Grygus et al. |
| 2023/0122652 A1 | 4/2023 | Breingan et al. |
| 2023/0128850 A1 | 4/2023 | Marcoz et al. |
| 2023/0130563 A1 | 4/2023 | Richards et al. |
| 2023/0145128 A1 | 5/2023 | Demirozer et al. |
| 2023/0149632 A1 | 5/2023 | Grygus |
| 2023/0233755 A1 | 7/2023 | Smith |
| 2023/0241310 A1 | 8/2023 | Stewart et al. |
| 2023/0285680 A1 | 9/2023 | Huang |
| 2023/0293818 A1 | 9/2023 | Johnson et al. |
| 2024/0033445 A1 | 2/2024 | Günay et al. |
| 2024/0033446 A1 | 2/2024 | Günay et al. |
| 2024/0066216 A1 | 2/2024 | Pizzochero et al. |
| 2024/0148965 A1 | 5/2024 | Scheurer et al. |

FOREIGN PATENT DOCUMENTS

| | | |
|---|---|---|
| CA | 2669616 A1 | 5/2008 |
| CA | 2669616 C | 6/2016 |
| CH | 144526 | 7/2021 |
| CL | 201903061 | 3/2020 |
| CL | 202201235 | 11/2022 |
| CL | 202301857 | 6/2023 |
| CL | 202301861 | 6/2023 |
| CL | 202301862 | 6/2023 |
| CL | 202301863 | 6/2023 |
| CL | 202301864 | 6/2023 |
| CN | 1026391 C | 11/1994 |
| CN | 101132822 | 2/2008 |
| CN | 101516424 A | 8/2009 |
| CN | 101531585 A | 9/2009 |
| CN | 102015011 A | 4/2011 |
| CN | 102149416 A | 8/2011 |
| CN | 102665795 | 9/2012 |
| CN | 103118723 A | 5/2013 |
| CN | 103619378 A | 3/2014 |
| CN | 104602733 A | 5/2015 |
| CN | 104602735 A | 5/2015 |
| CN | 105263562 | 1/2016 |
| CN | 105413021 | 3/2016 |
| CN | 306715264 S | 7/2021 |
| CO | 6920282 A2 | 4/2014 |
| EUIPO | -001371280-0001 | 5/2013 |
| EUIPO | -003147776-0001 | 5/2016 |
| EUIPO | -003814102-0001 | 3/2017 |
| EUIPO | -003814102-0004 | 3/2017 |
| EUIPO | -007257621-0001 | 11/2019 |
| EP | 1002551 A2 | 5/2000 |
| EP | 1284758 | 11/2001 |
| EP | 1219283 A3 | 12/2002 |
| EP | 1064035 B1 | 11/2003 |
| EP | 1518575 A1 | 3/2005 |
| EP | 1646412 B1 | 3/2007 |
| EP | 1 920 793 A1 | 5/2008 |
| EP | 1465689 B1 | 9/2009 |
| EP | 1855754 B1 | 9/2009 |
| EP | 1696981 B1 | 10/2009 |
| EP | 2396058 | 8/2010 |
| EP | 2219710 B1 | 4/2011 |
| EP | 2301611 B1 | 8/2012 |
| EP | 2608825 B1 | 8/2014 |
| EP | 2946800 A1 | 11/2015 |
| EP | 2571549 B1 | 2/2016 |
| EP | 2300078 B1 | 3/2016 |
| EP | 3000497 A3 | 7/2016 |
| EP | 2902060 B1 | 9/2016 |
| EP | 2736565 B1 | 7/2017 |
| EP | 3260146 A1 | 12/2017 |
| EP | 3260147 A1 | 12/2017 |
| EP | 3260149 A1 | 12/2017 |
| EP | 3260151 A1 | 12/2017 |
| EP | 2929900 B1 | 2/2019 |
| EP | 3852840 A1 | 7/2021 |
| EP | 3862038 A1 | 8/2021 |
| EP | 2731641 B1 | 9/2021 |
| EP | 3705149 B1 | 9/2021 |
| EP | 3233163 B1 | 10/2021 |
| EP | 3630227 B1 | 11/2021 |
| EP | 3925643 A1 | 12/2021 |
| EP | 3928812 A1 | 12/2021 |
| EP | 3077022 B1 | 1/2022 |
| EP | 3618895 B1 | 4/2022 |
| EP | 3760253 B1 | 4/2022 |
| EP | 3714922 B1 | 5/2022 |
| EP | 3756704 B1 | 5/2022 |
| EP | 3664864 B1 | 6/2022 |
| EP | 4029545 A1 | 7/2022 |
| EP | 3658203 B1 | 8/2022 |
| EP | 2991711 B1 | 10/2022 |
| EP | 3256189 B1 | 10/2022 |
| EP | 4 088 761 A1 | 11/2022 |
| EP | 3549524 B1 | 1/2023 |
| EP | 3268065 B1 | 5/2023 |
| EP | 3474926 B1 | 5/2023 |
| FR | 1137035 A | 11/1955 |
| GB | 20334 | 9/1902 |
| GB | 676973 | 4/1950 |
| GB | 2064964 A | 6/1981 |
| GB | 0229384 | 1/2003 |
| GB | 2396298 A | 6/2004 |
| GB | 2467904 A | 8/2010 |
| IN | 3612/DELNP/2010 | 11/2011 |
| JP | S4876390 A | 10/1973 |
| JP | S645565 A | 1/1989 |
| JP | H03250270 A | 11/1991 |
| JP | 6-207644 A | 7/1994 |
| JP | H07501234 A | 2/1995 |
| JP | H0852213 A | 2/1996 |
| JP | 2003527159 A | 9/2003 |
| JP | 2005058415 A | 3/2005 |
| JP | 2005-145384 A | 6/2005 |
| JP | 2005524447 A | 8/2005 |
| JP | 2005-534433 A | 11/2005 |
| JP | 2009-505720 A | 2/2009 |
| JP | 2011-508634 A | 3/2011 |
| JP | 2013/529520 A | 7/2013 |
| JP | 2014510573 A | 5/2014 |
| JP | 2014-124452 A | 7/2014 |
| JP | D1692548 S | 8/2021 |

(56) References Cited

FOREIGN PATENT DOCUMENTS

| | | |
|---|---|---|
| JP | 1736157 S | 2/2023 |
| JP | 1736158 S | 2/2023 |
| JP | 1736189 S | 2/2023 |
| JP | 1736190 S | 2/2023 |
| JP | 1743322 S | 5/2023 |
| JP | 1746594 S | 6/2023 |
| JP | 1746678 S | 6/2023 |
| KR | 10-2004-0064320 A | 7/2004 |
| KR | 10-2004-0096561 A | 11/2004 |
| KR | 10-2005-0092690 A | 9/2005 |
| KR | 10-2013-0137249 A | 12/2013 |
| KR | 10-1496207 A | 3/2015 |
| KR | 10-2016-0001262 A | 1/2016 |
| NZ | 576654 A | 7/2012 |
| RU | 2127131 C1 | 3/1999 |
| RU | 2573042 C2 | 1/2016 |
| TW | D211147 S | 4/2021 |
| WO | 94/07553 A1 | 4/1994 |
| WO | 99/07425 A1 | 2/1999 |
| WO | 00/20058 | 4/2000 |
| WO | WO-03024511 A1 | 3/2003 |
| WO | WO-03092771 A1 | 11/2003 |
| WO | WO-2004044464 A1 | 5/2004 |
| WO | WO-2004075955 A1 | 9/2004 |
| WO | 2006/067217 A2 | 6/2006 |
| WO | WO-2006061170 A1 | 6/2006 |
| WO | WO-2007035621 A1 | 3/2007 |
| WO | 2007/050788 | 5/2007 |
| WO | WO-2008091838 A2 | 7/2008 |
| WO | 2009/024608 A1 | 2/2009 |
| WO | WO-2009030974 A1 | 3/2009 |
| WO | WO-2009030975 A1 | 3/2009 |
| WO | WO-2009128265 A1 | 10/2009 |
| WO | WO-2009158613 A1 | 12/2009 |
| WO | WO-2010029054 A1 | 3/2010 |
| WO | WO-2010035057 A1 | 4/2010 |
| WO | WO-2010035059 A1 | 4/2010 |
| WO | WO-2011014514 A1 | 2/2011 |
| WO | WO-2011060197 A1 | 5/2011 |
| WO | WO-2011084951 A2 | 7/2011 |
| WO | 2011/095091 A1 | 8/2011 |
| WO | WO-2011125133 A1 | 10/2011 |
| WO | WO-2011133823 A1 | 10/2011 |
| WO | 2011139110 A2 | 11/2011 |
| WO | 2011/156373 A1 | 12/2011 |
| WO | WO-2012032411 A2 | 3/2012 |
| WO | 2012/114105 A1 | 8/2012 |
| WO | WO-2012101669 A1 | 8/2012 |
| WO | 2013/034647 A1 | 3/2013 |
| WO | 2013/077800 A1 | 5/2013 |
| WO | WO-2013155153 A1 | 10/2013 |
| WO | 2013/179137 A2 | 12/2013 |
| WO | WO-2014037946 A1 | 3/2014 |
| WO | WO-2014049745 A1 | 4/2014 |
| WO | WO-2014054535 A1 | 4/2014 |
| WO | 2014066256 A1 | 5/2014 |
| WO | WO-2014106096 A1 | 7/2014 |
| WO | WO-2014149357 A1 | 9/2014 |
| WO | 2014185681 A1 | 11/2014 |
| WO | WO-2015024960 A1 | 2/2015 |
| WO | 2015/055747 A1 | 4/2015 |
| WO | WO-2015081337 A2 | 6/2015 |
| WO | WO-2015123688 A1 | 8/2015 |
| WO | 2015/143058 A1 | 9/2015 |
| WO | WO-2015164647 A1 | 10/2015 |
| WO | WO-2015164648 A1 | 10/2015 |
| WO | WO-2015185176 A1 | 12/2015 |
| WO | WO-2015187793 A1 | 12/2015 |
| WO | 2016033496 A1 | 3/2016 |
| WO | WO-2016041871 A1 | 3/2016 |
| WO | WO-2016041873 A1 | 3/2016 |
| WO | WO-2016049532 A1 | 3/2016 |
| WO | 2016/052332 | 4/2016 |
| WO | WO-2016053954 A1 | 4/2016 |
| WO | WO-2016074850 A1 | 5/2016 |
| WO | 2016/100055 A1 | 6/2016 |
| WO | WO-2016091841 A1 | 6/2016 |
| WO | WO-2016100781 A1 | 6/2016 |
| WO | WO-2016115372 A1 | 7/2016 |
| WO | WO-2016130679 A2 | 8/2016 |
| WO | 2016149038 A1 | 9/2016 |
| WO | WO-2016141082 A1 | 9/2016 |
| WO | 2016157638 A1 | 10/2016 |
| WO | WO-2016210404 A1 | 12/2016 |
| WO | WO-2017037468 A1 | 3/2017 |
| WO | WO-2017050781 A1 | 3/2017 |
| WO | 2014/049712 A1 | 4/2017 |
| WO | 2017/062943 A2 | 4/2017 |
| WO | WO-2017089271 A1 | 6/2017 |
| WO | WO-2017089287 A1 | 6/2017 |
| WO | WO-2017089288 A1 | 6/2017 |
| WO | WO-2017139003 A1 | 8/2017 |
| WO | WO-2017139573 A1 | 8/2017 |
| WO | WO-2017139741 A1 | 8/2017 |
| WO | WO-2017141255 A1 | 8/2017 |
| WO | WO-2017219156 A1 | 12/2017 |
| WO | WO-2017219157 A1 | 12/2017 |
| WO | WO-2017219158 A1 | 12/2017 |
| WO | WO-2018015749 A2 | 1/2018 |
| WO | WO-2018100201 A1 | 6/2018 |
| WO | WO-2018130944 A1 | 7/2018 |
| WO | WO-2018144056 A1 | 8/2018 |
| WO | WO-2018164829 A1 | 9/2018 |
| WO | WO-2018204779 A1 | 11/2018 |
| WO | WO-2018222521 A1 | 12/2018 |
| WO | WO-2019018169 A1 | 1/2019 |
| WO | WO-2020058069 A1 | 3/2020 |
| WO | WO-2020173993 A1 | 9/2020 |
| WO | 2020/219127 A1 | 10/2020 |
| WO | WO-2021012852 A1 | 1/2021 |
| WO | 2021093327 A1 | 5/2021 |
| WO | WO-2021222057 A1 | 11/2021 |
| WO | WO-2021224388 A1 | 11/2021 |
| WO | WO-2021233982 A1 | 11/2021 |
| WO | WO-2022072809 A1 | 4/2022 |
| WO | WO-2022088501 A1 | 5/2022 |
| WO | WO-2022097057 A1 | 5/2022 |
| WO | WO-2022116603 A1 | 6/2022 |
| WO | WO-2022121945 A1 | 6/2022 |
| WO | WO-2022147166 A1 | 7/2022 |
| WO | WO-2022147985 A1 | 7/2022 |
| WO | WO-2022148048 A1 | 7/2022 |
| WO | WO-2022159242 A1 | 7/2022 |
| WO | WO-2022212239 A1 | 10/2022 |
| WO | WO-2022212713 A2 | 10/2022 |
| WO | WO-2022271950 A1 | 12/2022 |
| WO | WO-2023272784 A1 | 1/2023 |
| WO | 2023150090 A1 | 8/2023 |
| WO | 2023187749 A1 | 10/2023 |
| WO | 2024052442 A1 | 3/2024 |
| WO | 2024053149 A1 | 3/2024 |
| WO | 2024068801 A1 | 4/2024 |
| WO | 2024069630 A1 | 4/2024 |

OTHER PUBLICATIONS

International Search Report and Written Opinion mailed May 23, 2023 in International Application No. PCT/2022/079921 (32 pages).
Chinese Office Action for Chinese Application No. 201680027080.7 mailed on Sep. 4, 2019, 9 pages.
Dia Tribe, Making Sense of Diabetes, Calibre Finesse Bolus Insulin Patch Pump to Launch in the US in 2016, 2016, [retrieved on Nov. 22, 2016]. Retrieved from the Internet: (URL: https://diatribe.org/calibra-finesse-bolus-insulin-patch-pump-launch-us-2016), 1 Page.
Diabetes, The Healthy Living Magazine, How Insulin Pumps Work, An inside look at insulin pump technology, By Erika Gebel Berg, PhD, Sep. 2014, [Retrieved on Nov. 22, 2016], retrieved from the Internet: (URL: http://www.diabetesforecast.org/2014/09-sep/how-insulin-pumps-work.html), 2016 American Diabetes Association, 6 pages.
Drug Delivery Performance and Antibody Viability after gas powered plunger injection, PODD, altaviz, Oct. 15, 2018, 15 pages.

(56) References Cited

OTHER PUBLICATIONS

European Examination Report for Application No. 16713195.2, mailed on Aug. 10, 2018, 8 pages.
European search report for European Application No. 20198799.7 mailed on Dec. 21, 2020, 8 pages.
International Search Report for Application No. PCT/US2018/031077 mailed on Sep. 17, 2018, 5 pages.
Japanese Office Action in corresponding Japanese Application No. 2017-547515, mailed on Dec. 24, 2019, 5 pages.
Sorrel Medical, Your Way to Deliver More, PODD, 2018, 18 pages.
Verjans et al. "A New Concept in Aseptic Filling: Closed-Vial Technology", Pharmaceutical Technology, May 2005, 4 pages.
Very Well, What is the V-GO Insulin Patch Pump?, Valeritas V-GO Disposable Insulin Device, Retrieved on Nov. 22, 2016], retrieved from the Internet: (URL: http://www.verywell.com/what-is-an-Insulin-Patch-Pump-1067254), 9 pages.
Chinese Notice of Allowance mailed Mar. 3, 2022 in Chinese Application No. 20188027244.5 (7 pages).
Extended European Search Report dated Aug. 25, 2022 in European Application No. 22160171.9 (8 pages).
Eurasian Patent Office Search Report issued in Eurasian Application No. 202290947 on Sep. 8, 2022 (3 pages).
English Translation of the Preliminary Office Action Report Related to Brazilian Patent Application No. BR112019020705-8, Sep. 19, 2022 (2 pages).
Medicom Innovation Partner, Flexible Wearable Patch Pump, Wearable Injectors, ONdrugDelivery Magazine, Issue 78, <www.issuu.com>, 2017 (1 page).
West Pharmaceutical Services, E3D, OBI-1 Wearable Injector, On Body Injector, Elcam Drug Delivery Services, <www.issuu.com>, 2019 (1 page).
West Pharmaceutical Services, Pharmapack 2021: Gerresheimer with Innocative SensAIR Platform for a Drug Delivery Device for Biologics, Sensair, Gerresheimer's Group, Pharmaceutical Technology, <www.issuu.com>, 2022 (1 page).
West Pharmaceutical Services, Wearable Drug Delivery Device, Eitan Sorrel Medical, <www.issuu.com>, 2019 (1 page).
West Pharmaceutical Services, SmartDose® On-Body Delivery System, West, <www.issuu.com>, 2019 (1 page).
Ypsomed, Ypsodose, Delivery Systems, <yds.ypsomed.com>, Webpage last updated Jun. 4, 2022 (1 page).
West Pharmaceutical Services, SmartDose® On-Body Delivery System Platform (OBDS), <www.issuu.com>, 2017 (1 page).
BD Libertas, Wearable Injector, BD Drug Delivery Systems, <drugdeliverysystems.bd.com>, Accessed Jun. 27, 2023.
International Search Report and Written Opinion mailed Sep. 30, 2024 in International Application No. PCT/US2024/034116 (10 pages).
Invitation to Pay Additional Fees and, Where Applicable, Protest Fee, mailed Oct. 2, 2024, in International Application No. PCT/US2024/034114 (15 pages).
International Preliminary Report on Patentability mailed May 30, 2024 in International Application No. PCT/US2022/079921 (23 pages).
International Search Report and Written Opinion mailed Aug. 26, 2024 in International Application No. PCT/US2024/029782 (13 pages).
International Search Report and Written Opinion mailed Sep. 3, 2024 in International Application No. PCT/US2024/029802 (12 pages).
International Search Report and Written Opinion mailed Sep. 19, 2024 in International Application No. PCT/US2024/029801, 12 pages.

\* cited by examiner

AUTO-INJECTOR AND RELATED METHODS OF USE

CROSS-REFERENCE TO RELATED APPLICATION(S)

This patent application is a continuation of and claims the benefit of priority to U.S. application Ser. No. 16/495,868, filed Sep. 20, 2019, which is the U.S. national phase entry under 35 U.S.C. § 371 of International Application No. PCT/US2018/031077, filed May 4, 2018, which claims the benefit under 35 U.S.C. § 119 to U.S. Provisional Patent Application No. 62/502,278, filed on May 5, 2017, the entireties of which are incorporated herein by reference.

TECHNICAL FIELD

This disclosure is directed to an auto-injector and related methods of use.

INTRODUCTION

In various available auto-injectors, upon activation by a user, a needle is deployed, and fluid is delivered from the needle into the user. After completion of fluid delivery, the needle may be retracted for user comfort, needle safety, and positive perception of the product. However, many auto-injectors use separate springs or motors for the injection and needle removal steps. In addition, such injection assemblies generally require separate user actions for both inserting and removing the needle.

SUMMARY OF THE DISCLOSURE

In one aspect, the present disclosure is directed to an injection device. The injection device includes a carrier, a needle, a driver coupled to the needle, the driver being slidable relative to the carrier between a retracted configuration and a deployed configuration, a shuttle configured to move the driver between the retracted configuration and the deployed configuration, and a stop configured to move from a first configuration to a second configuration, wherein the stop is configured to maintain the driver in the deployed configuration, and movement of the stop from the first configuration to the second configuration allows the shuttle to move the driver from the deployed configuration to the retracted configuration.

The shuttle is movable from a first position to a second position, and from the second position to a third position, wherein when the shuttle is in the first position, the driver is in the retracted configuration, when the shuttle is in the second position, the driver is in the deployed configuration, when the shuttle is in the third position, the driver is in the retracted configuration. The first position and the third position are different. The shuttle moves in one direction along an axis to move from the first position to the second position, and from the second position to the third position. The shuttle is configured to move only in the one direction. The injection device also includes a deployment gear coupled to the carrier, and a retraction gear coupled to the carrier, wherein the driver is coupled to the deployment gear and the retraction gear, the shuttle includes a rack gear configured to engage the deployment gear and the retraction gear, wherein direct engagement of the rack gear with the deployment gear moves the driver from the retracted configuration to the deployed configuration, and direct engagement of the rack gear with the retraction gear moves the driver from the deployed configuration to the retracted configuration. The rack gear directly contacts only one of the deployment gear and the retraction gear at any time. The rack gear is configured to drive rotation of the deployment gear in a first direction to move the driver from the retracted configuration to the deployed configuration, and drive rotation of the retraction gear in the first direction to move the driver from the deployed configuration to the retracted configuration. The driver includes a first rack and a second rack, wherein the first rack is configured to engage the deployment gear, and the second rack is configured to engage the retraction gear. The first rack and the second rack are located on opposing sides of the driver. The shuttle is configured to move along a first axis, the driver is configured to move along a second axis, and the first axis and the second axis are perpendicular to one another. The driver, before activation, is in contact with an impediment, and is prevented from moving out of the retracted configuration by the impediment. The injection device also includes a housing enclosing the carrier, wherein the impediment is integral with the housing. The movement of the carrier relative to the housing moves the driver out of contact with the impediment, allowing the driver to move from the retracted configuration to the deployed configuration. The injection device also includes a resilient member coupled to the shuttle, wherein, after the driver is moved out of contact with the impediment, the resilient member is configured to expand from a first compressed state to a second compressed state to move the shuttle from the first position to the second position. After the stop is moved from the first configuration to the second configuration, the resilient member is configured to expand from the second compressed state to a resting state to move the shuttle from the second position to the third position.

In another aspect, the present disclosure is directed to an injection device that includes a carrier including a stop, wherein the stop has a first end fixed to a remainder of the carrier, and a free second end, a first gear coupled to the carrier, a needle, a driver coupled to the carrier, the first gear, and the needle, the driver being slidable relative to the carrier between a retracted configuration and a deployed configuration, a shuttle including a rack gear configured to drive rotation of the first gear, wherein the rotation of the first gear moves the driver from the retracted configuration to the deployed configuration, wherein the free second end of the stop is configured to at least temporarily prevent movement of the shuttle while the driver is in the deployed configuration.

The injection device further includes a second gear coupled to the carrier, wherein flexion of the stop about the fixed first end, while the free second end is in contact with the shuttle, causes the shuttle to slide relative to the stop and drive rotation of the second gear, wherein the rotation of the second gear moves the driver from the deployed configuration to the retracted configuration.

In another aspect, the present disclosure is directed to an injection device that includes a needle movable between a retracted configuration and a deployed configuration, a vial configured to be in fluid communication with the needle, a piston configured to move within the vial, a motor configured to drive the piston, and a controller coupled to the motor, wherein the controller is configured to receive an indication that the injection device is positioned in contact a user, after receiving the indication, sending a signal to the motor to drive the piston in a first direction to put the needle and the vial in fluid communication and move the needle from the retracted configuration to the deployed configuration, and without requiring any intervention by a user after receiving the indication, and after sending the signal to drive the motor in the first direction, automatically sending a signal to the motor to drive the piston in a second direction to move the needle from the deployed configuration to the retracted configuration.

The injection device further includes a housing enclosing the vial, the piston, the motor, the controller, and the needle when the needle is in the retracted configuration, wherein the needle extends out of the housing in the deployed configuration. The injection device may include a cover or a shield that contains the distalmost portion of the needle in the retracted configuration. The injection device may include an audio module, a visual module, and a haptic module, each of the modules being coupled to the controller and configured to provide feedback to a user of the injection device. The injection device may include a top that seals an opening of the vial, the top including a portion including a rubber material that is permeable to a sterilant, wherein the needle includes a proximalmost portion configured to be coupled with the vial, and, before the needle and vial are in fluid communication with one another, the proximalmost portion of the needle is disposed within the portion formed of the rubber material. The injection device may include a cantilever coupled to the controller, and movable by the needle, wherein, when the needle is in the retracted configuration, the cantilever forms part of an open circuit that signals to the controller that the needle is in the retracted configuration, and when the needle is in the deployed configuration, the cantilever forms part of a closed circuit that signals to the controller that the needle is in the deployed configuration.

BRIEF DESCRIPTION OF THE FIGURES

The accompanying drawings, which are incorporated in and constitute a part of this specification, illustrate various examples and together with the description, serve to explain the principles of the disclosed examples and embodiments.

Aspects of the disclosure may be implemented in connection with embodiments illustrated in the attached drawings. These drawings show different aspects of the present disclosure and, where appropriate, reference numerals illustrating like structures, components, materials and/or elements in different figures are labeled similarly. It is understood that various combinations of the structures, components, and/or elements, other than those specifically shown, are contemplated and are within the scope of the present disclosure.

Moreover, there are many embodiments described and illustrated herein. The present disclosure is neither limited to any single aspect nor embodiment thereof, nor to any combinations and/or permutations of such aspects and/or embodiments. Moreover, each of the aspects of the present disclosure, and/or embodiments thereof, may be employed alone or in combination with one or more of the other aspects of the present disclosure and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended reflect or indicate the embodiment(s) is/are "example" embodiment(s).

Figure 1:
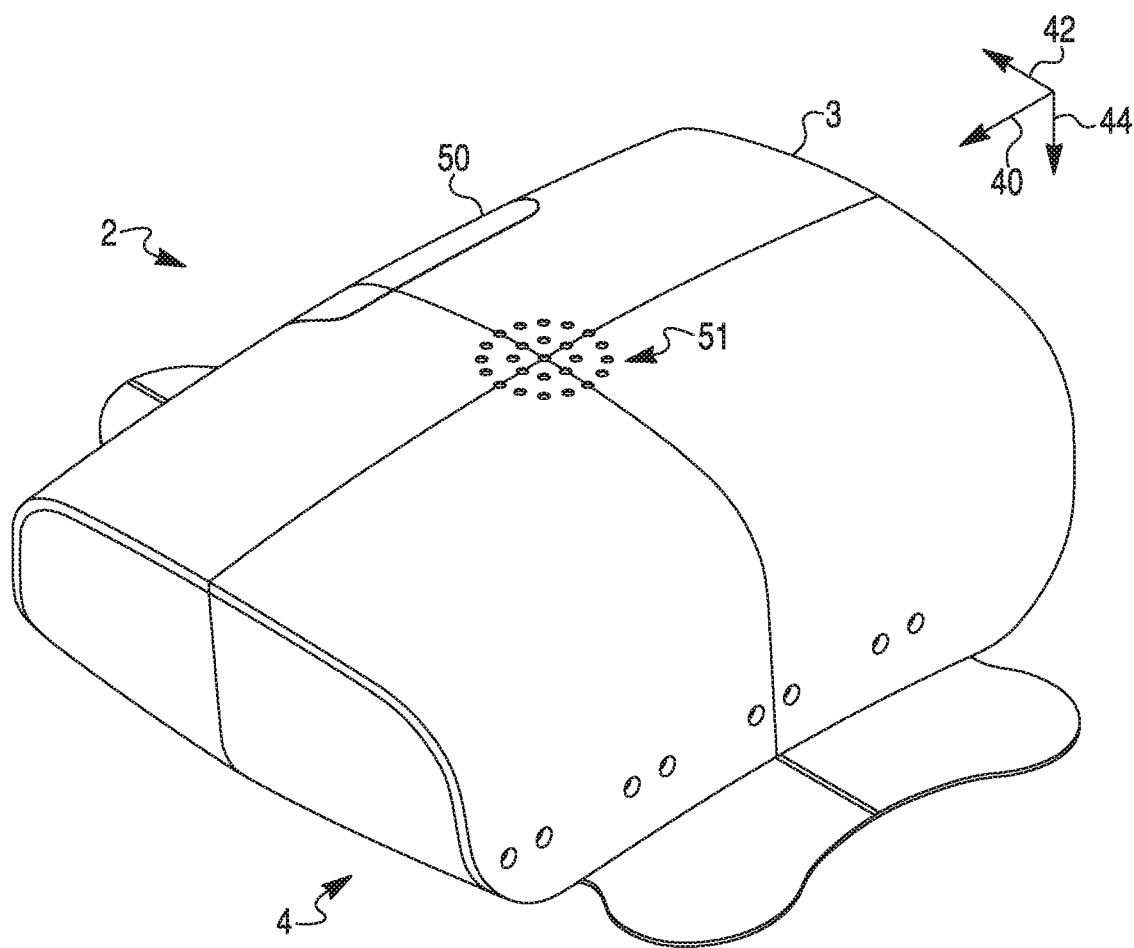

FIG. 1 is a perspective view of an auto-injector, according to an example of the disclosure.

Figure 2:
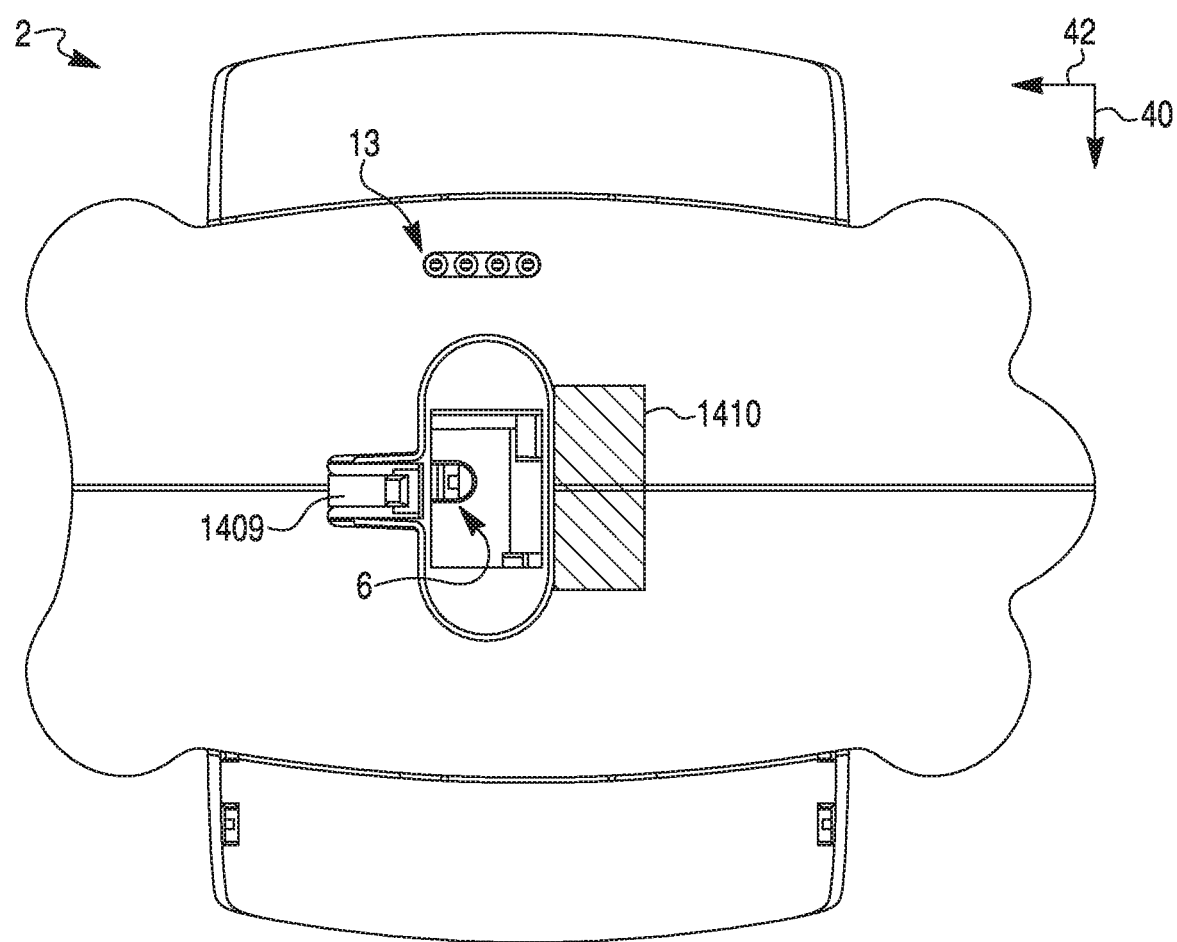

FIG. 2 is a bottom view of the auto-injector of FIG. 1.

Figure 3:
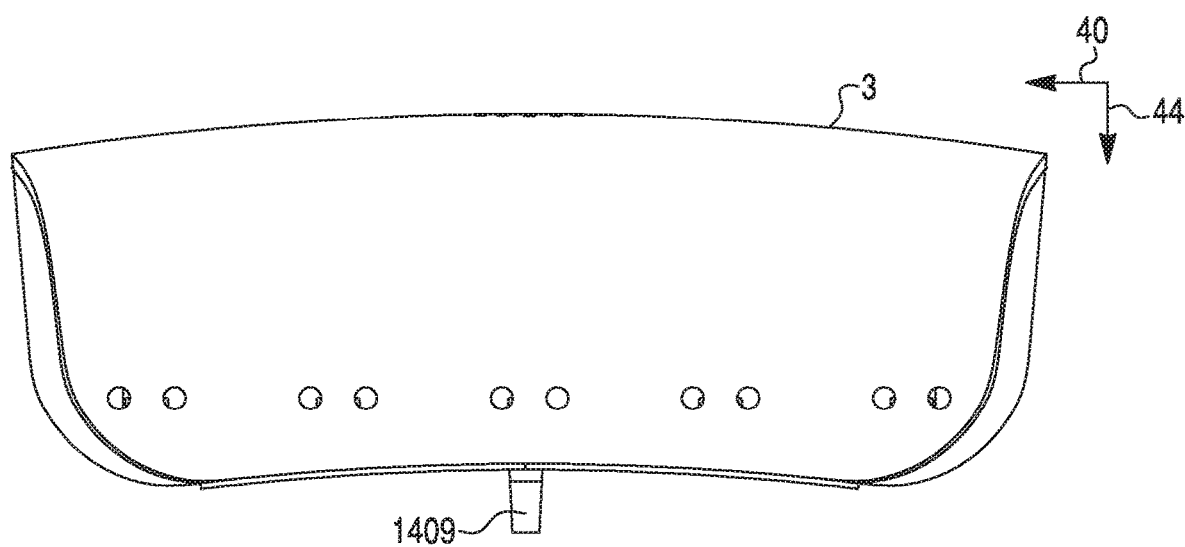

FIG. 3 is a side view of the auto-injector of FIG. 1, showing an activating switch extending away from a tissue-facing surface.

Figure 4:
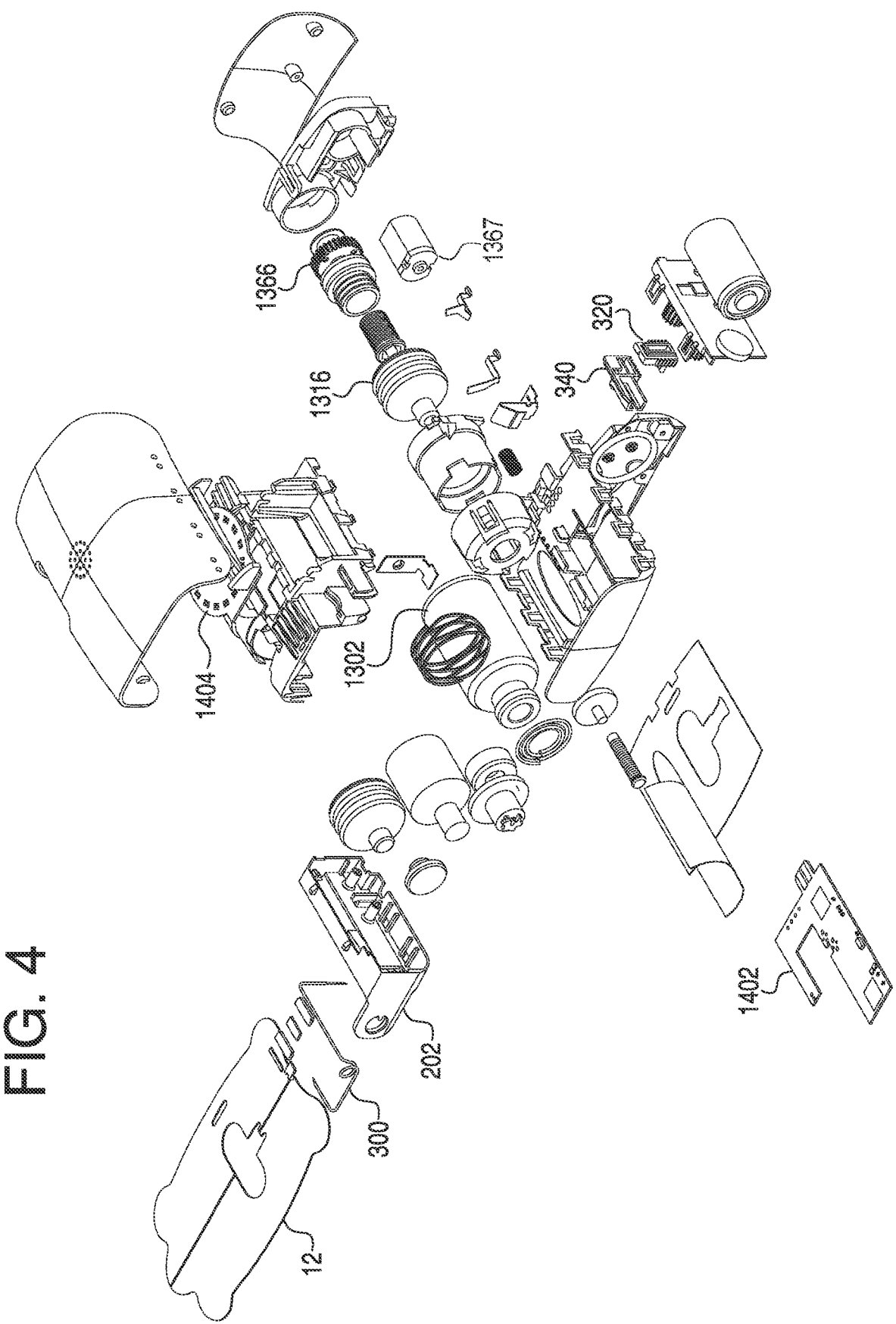

FIG. 4 is an exploded view of the auto-injector of FIG. 1.

Figure 4A:
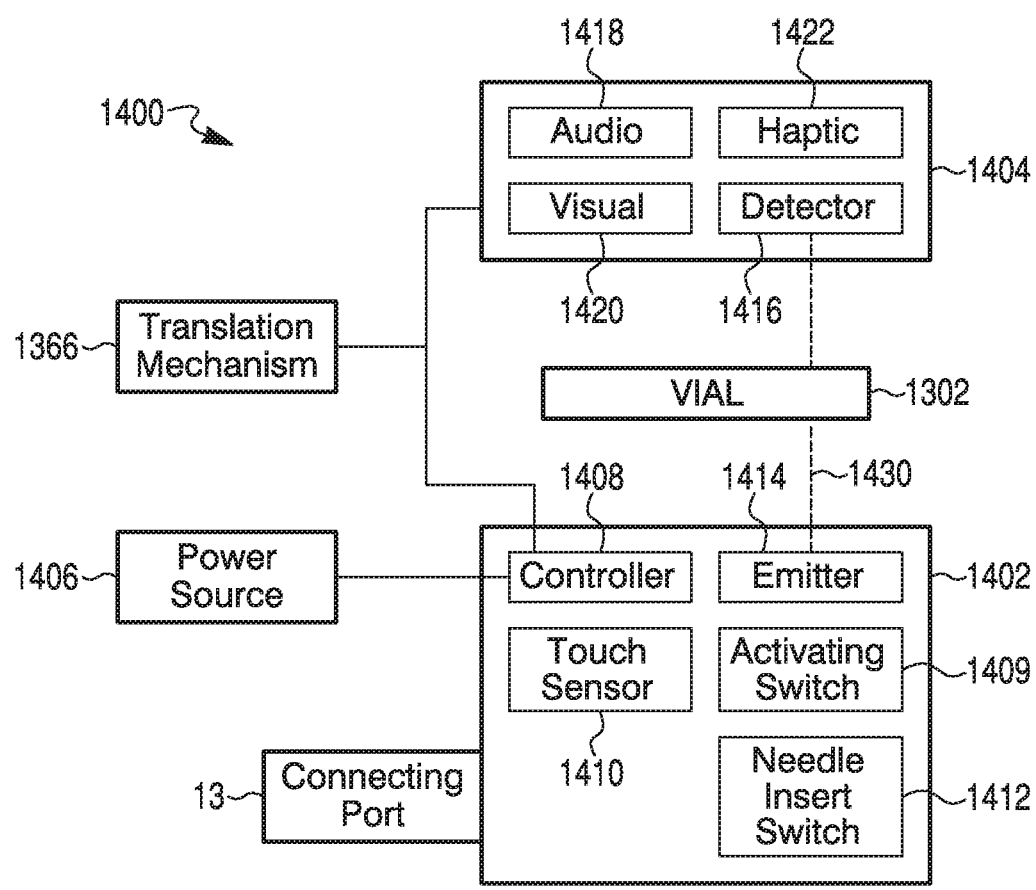

FIG. 4A is a schematic illustration of a control system of the auto-injector of FIG. 1.

Figure 4B:
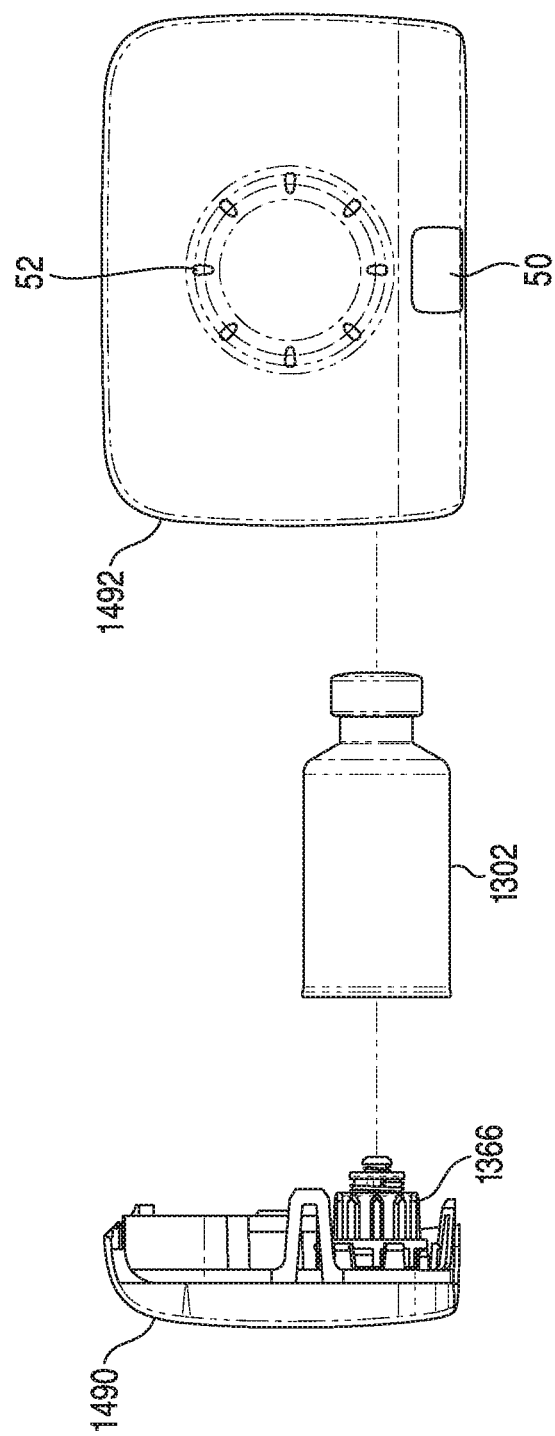

FIG. 4B is an exploded view of an auto-injector according to the disclosure.

Figure 4C:
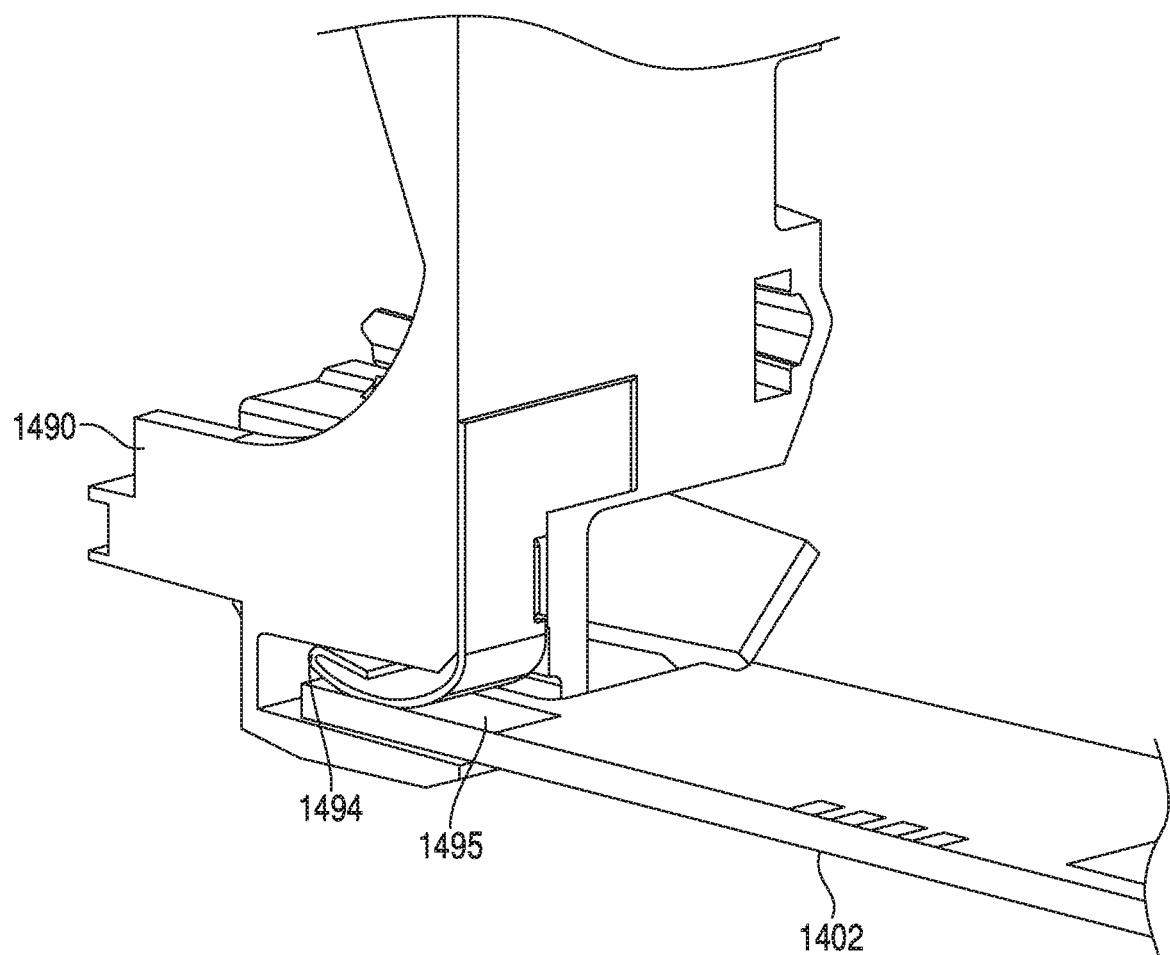

FIG. 4C is a perspective view of a portion of a housing and an electronics board, according to an aspect of the disclosure.

Figure 5:
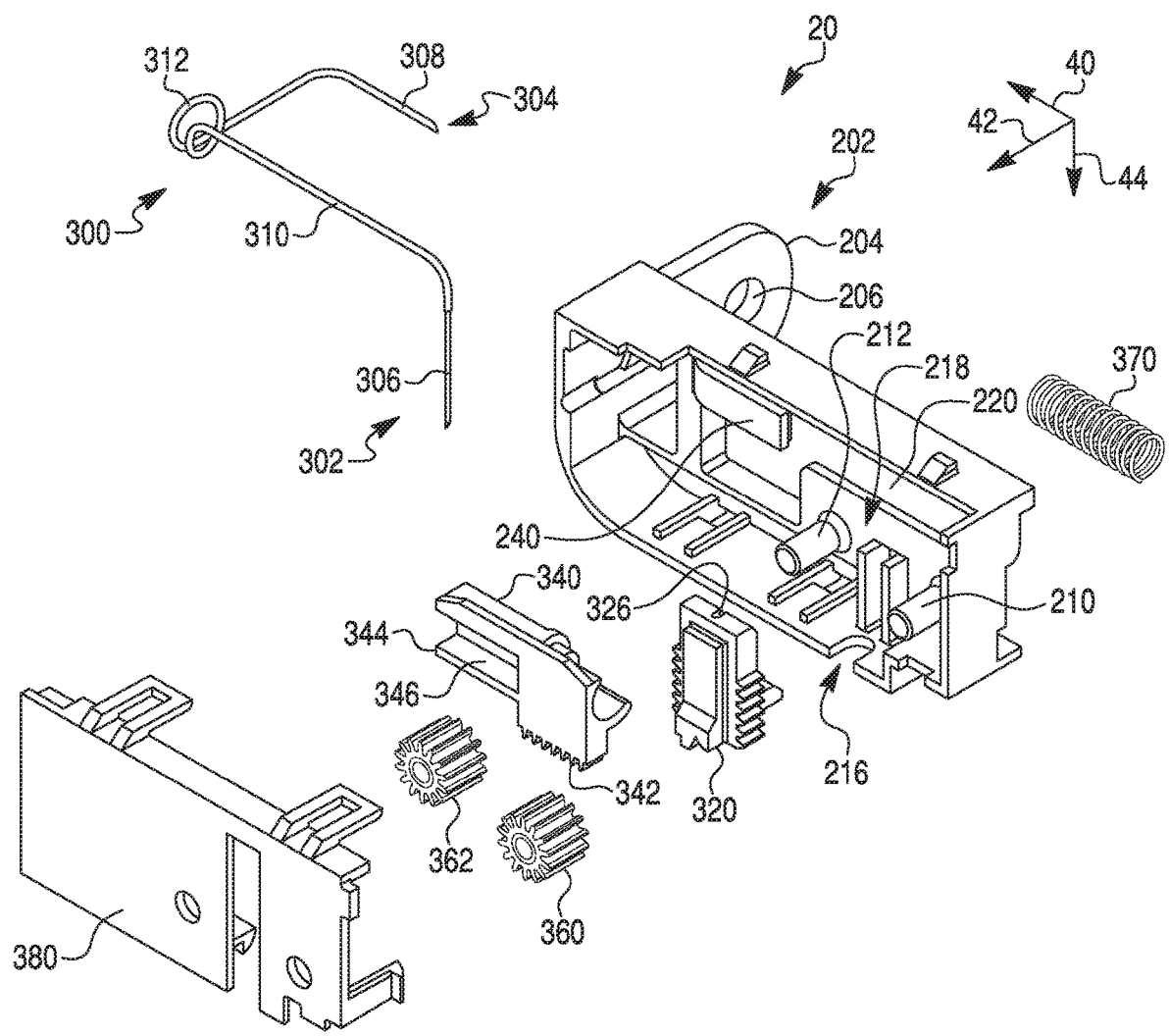

FIG. 5 is an exploded view of a needle mechanism.

Figure 6:
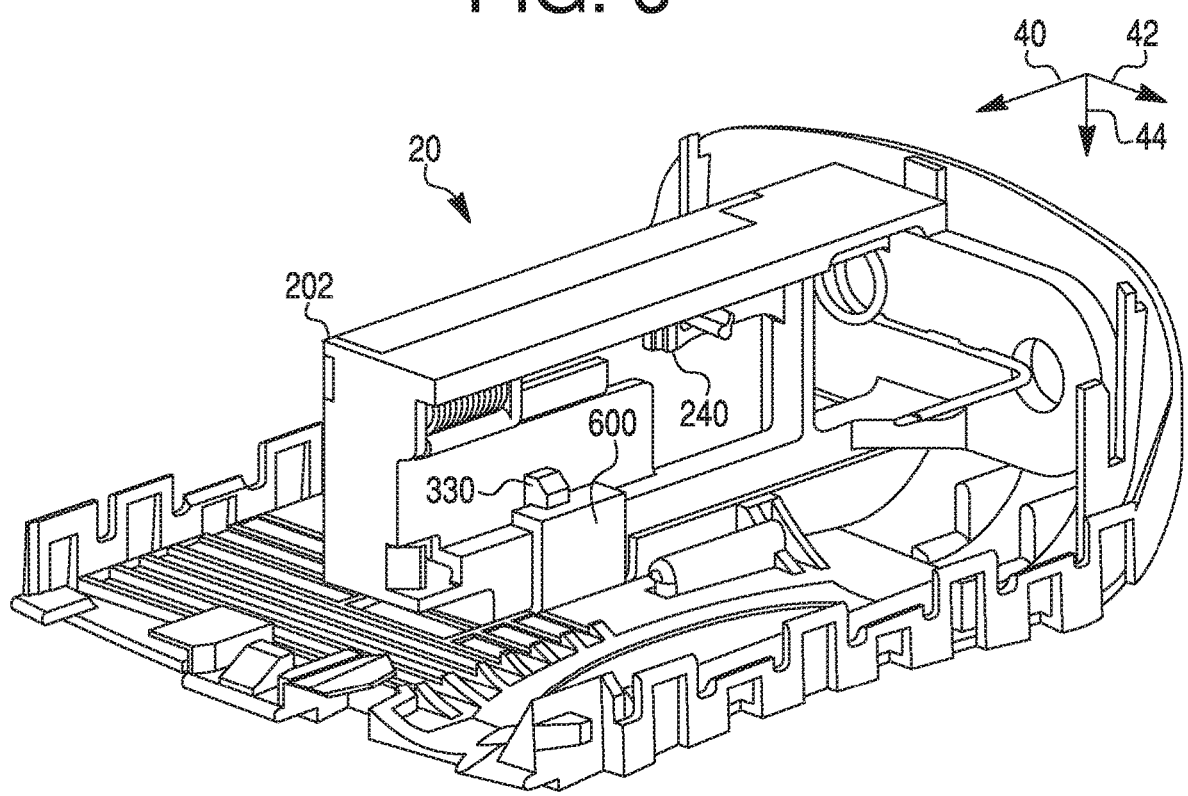

FIG. 6 is a perspective view of the needle mechanism of FIG. 5 in a first position.

FIGS. 7-11 are side views of the needle mechanism of FIG. 5.

Figure 12:
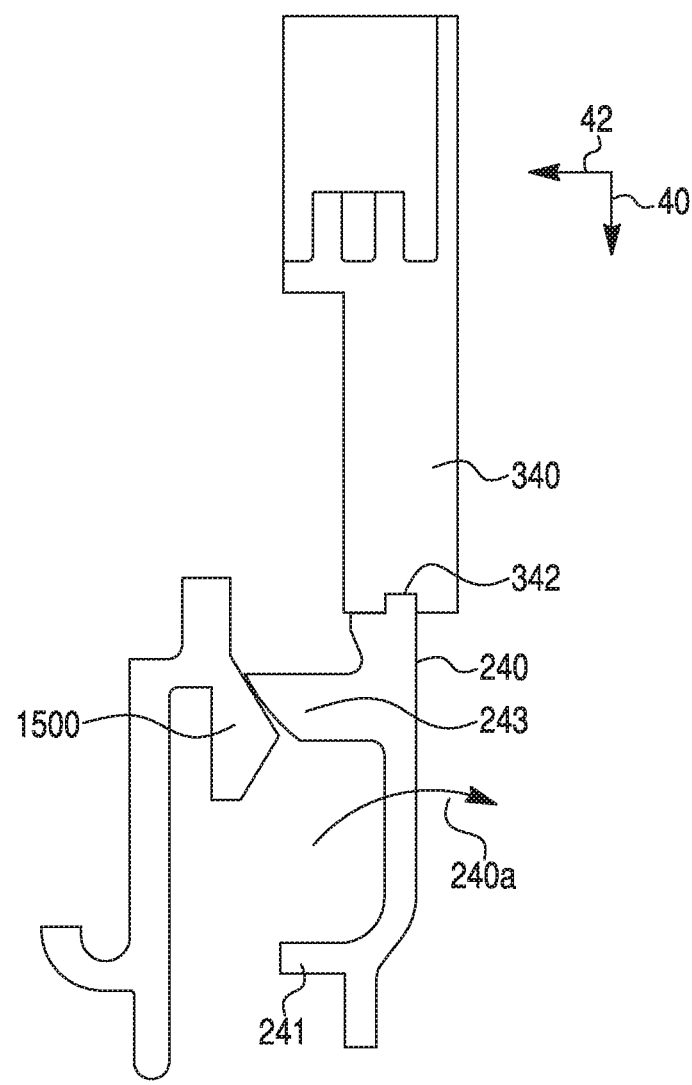

FIG. 12 is a side cross-sectional view of a portion of the auto-injector of FIG. 1.

Figure 13:
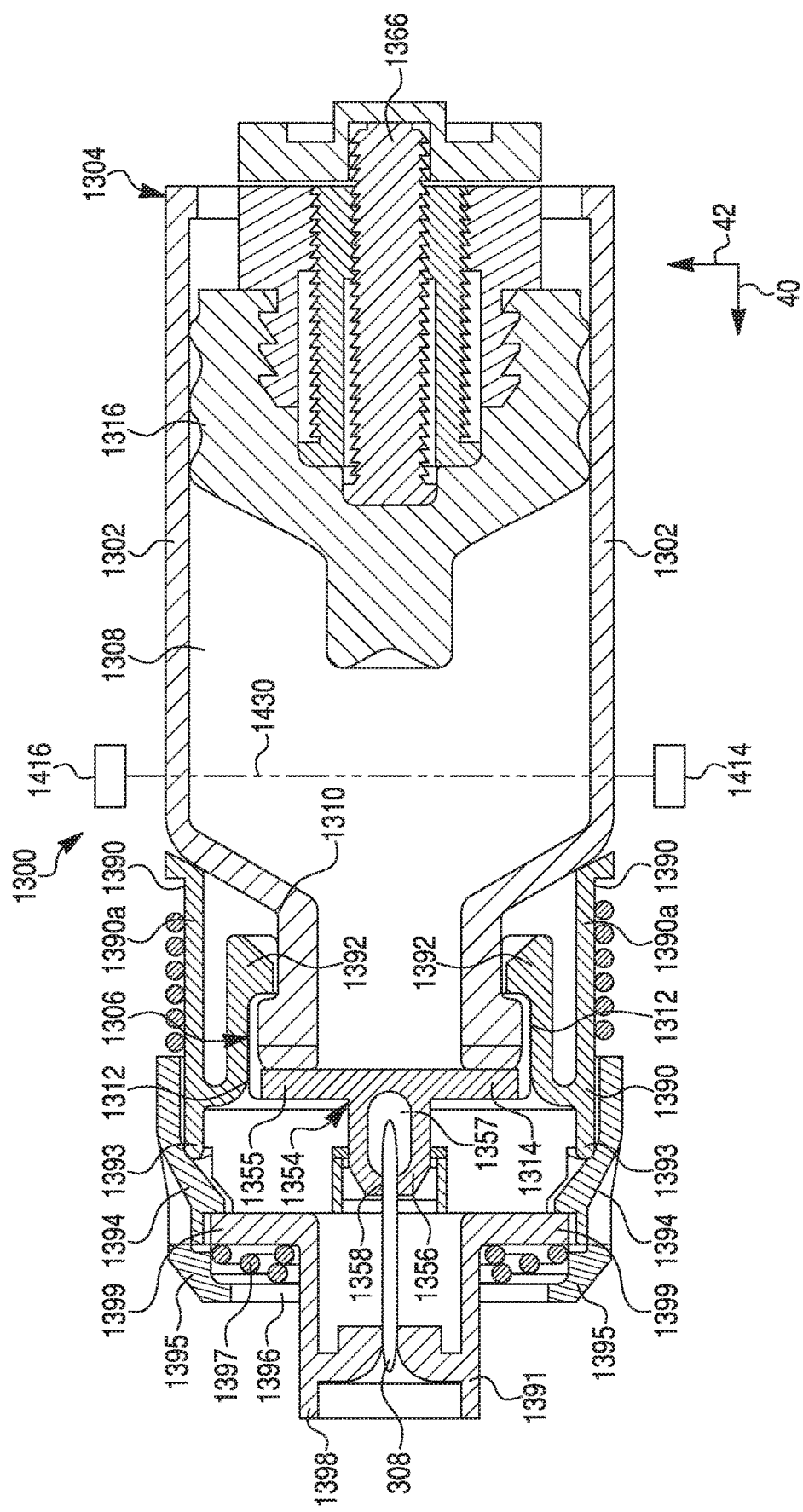
Figure 14:
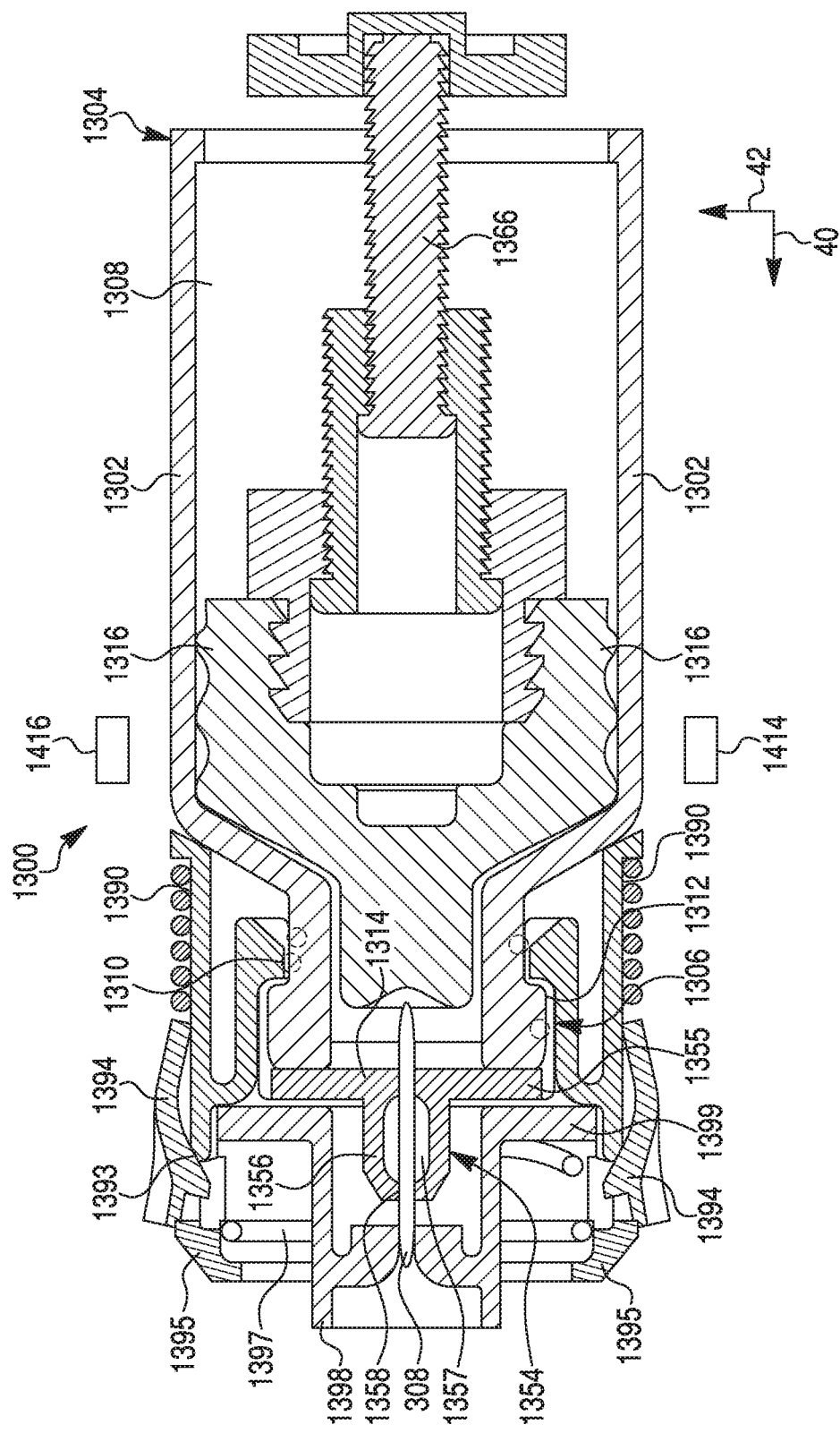

FIGS. 13 and 14 are side cross-sectional views of a piercing mechanism.

Figure 14A:
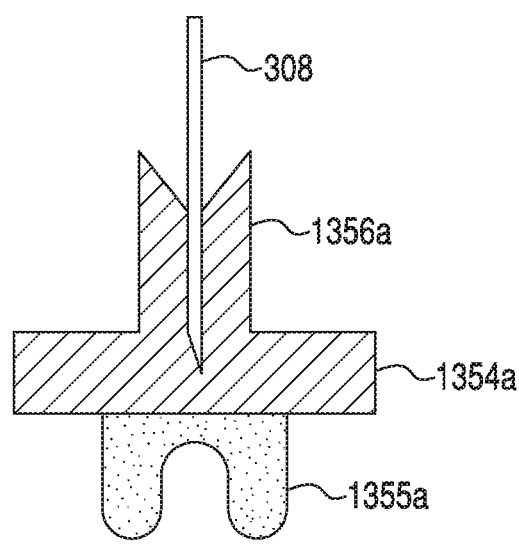

FIG. 14A is a cross-sectional view of a cap used in an alternative piercing mechanism.

Figure 15:
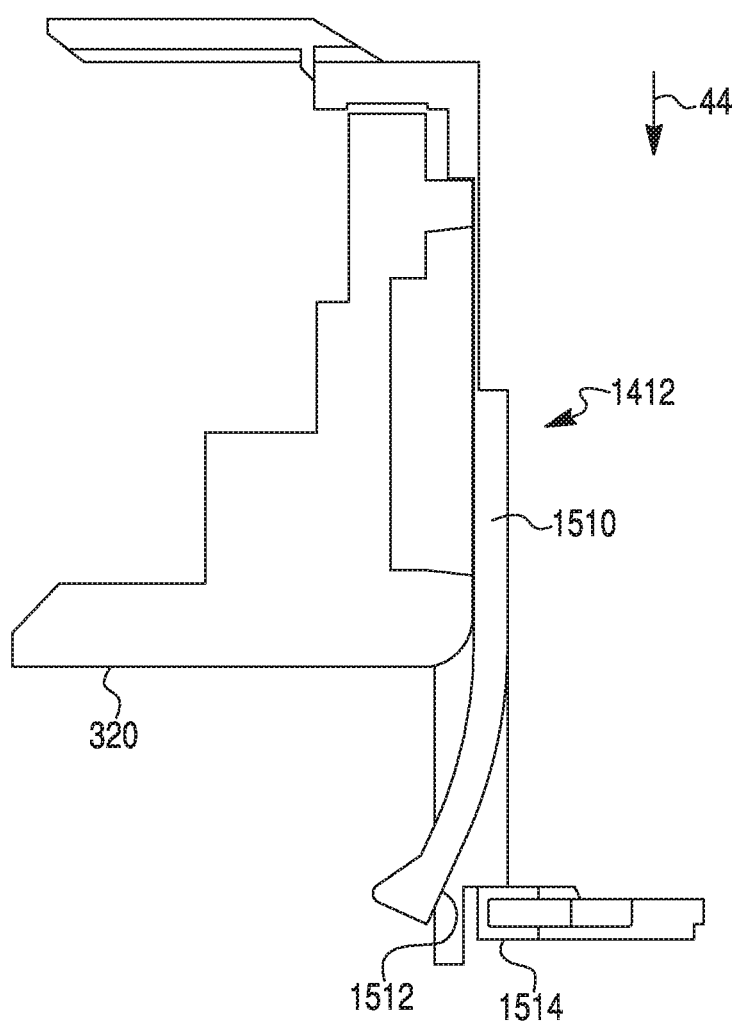

FIG. 15 is a side view of a needle insert switch.

Figure 16:
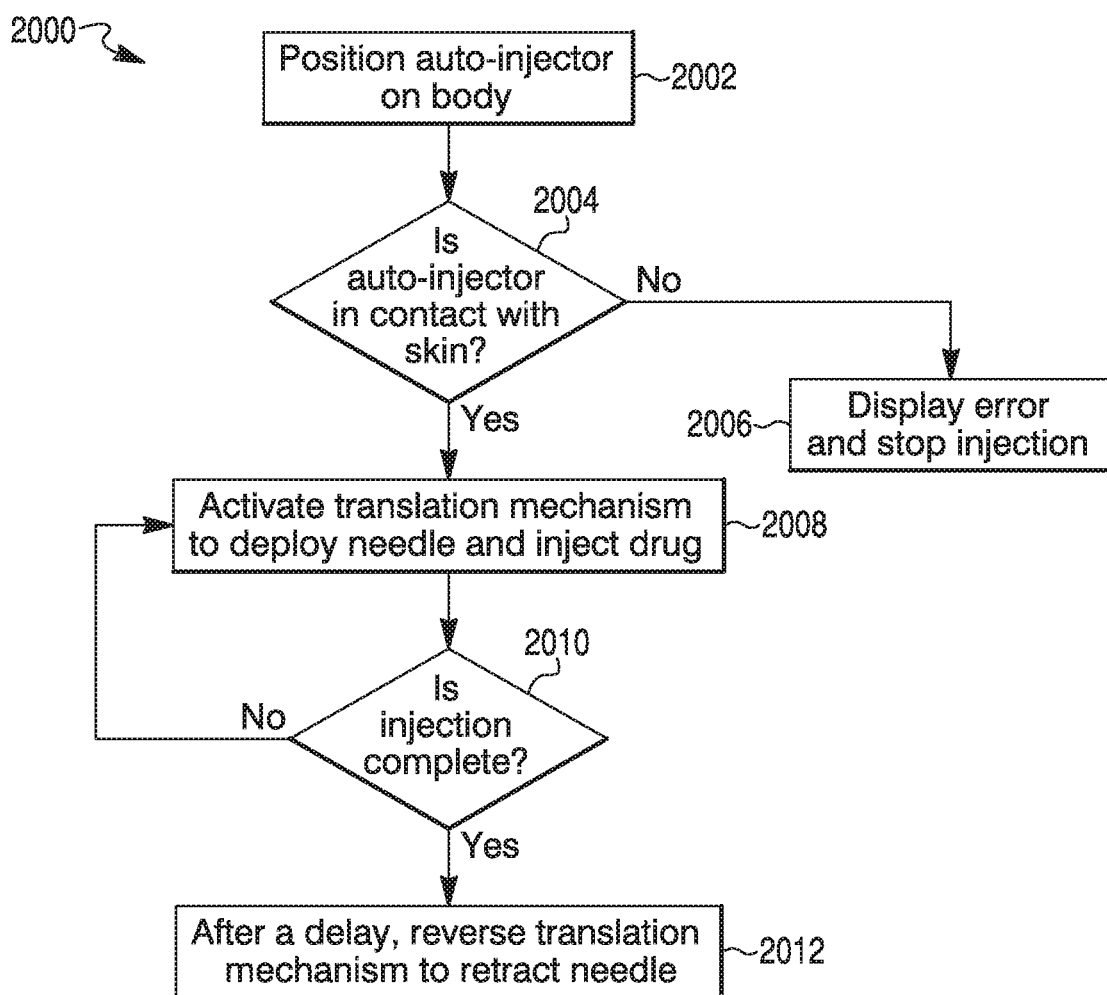

FIG. 16 is a flowchart of an exemplary method according to the disclosure.

FIGS. 17-23 illustrate needle mechanisms according to other examples of the present disclosure.

Figure 24:
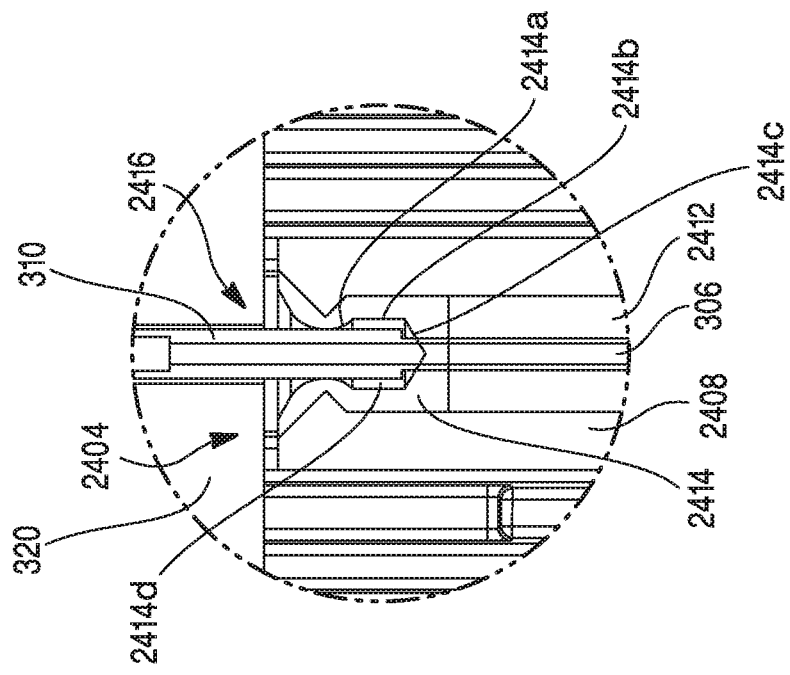

FIG. 24 is a cross-sectional view of the auto-injector of FIG. 1 and a needle shield.

Figure 25:
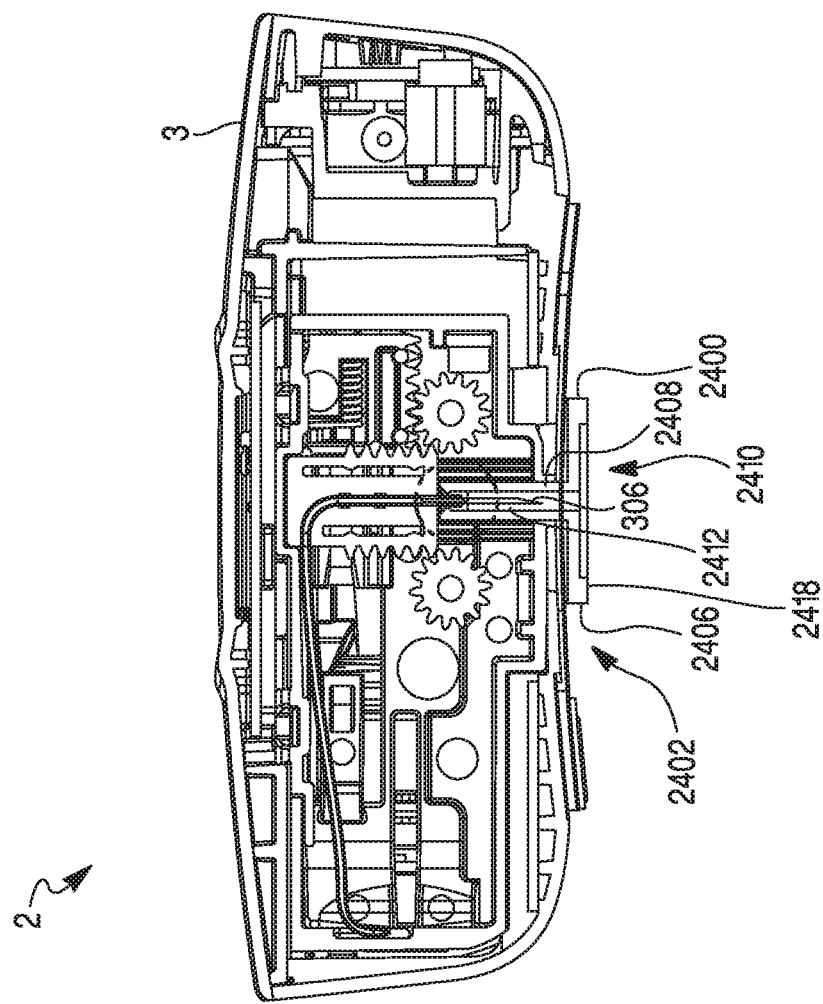

FIG. 25 is an enlargement of a portion of FIG. 24.

Again, there are many embodiments described and illustrated herein. The present disclosure is neither limited to any single aspect nor embodiment thereof, nor to any combinations and/or permutations of such aspects and/or embodiments. Each of the aspects of the present disclosure, and/or embodiments thereof, may be employed alone or in combination with one or more of the other aspects of the present disclosure and/or embodiments thereof. For the sake of brevity, many of those combinations and permutations are not discussed separately herein.

Notably, for simplicity and clarity of illustration, certain aspects of the figures depict the general structure and/or manner of construction of the various embodiments. Descriptions and details of well-known features and techniques may be omitted to avoid unnecessarily obscuring other features. Elements in the figures are not necessarily drawn to scale; the dimensions of some features may be exaggerated relative to other elements to improve understanding of the example embodiments. For example, one of ordinary skill in the art appreciates that the cross-sectional views are not drawn to scale and should not be viewed as representing proportional relationships between different components. The cross-sectional views are provided to help illustrate the various components of the depicted assembly, and to show their relative positioning to one another.

DETAILED DESCRIPTION

Reference will now be made in detail to examples of the present disclosure, which are illustrated in the accompanying drawings. Wherever possible, the same reference numbers will be used throughout the drawings to refer to the same or like parts. In the discussion that follows, relative terms such as "about," "substantially," "approximately," etc. are used to indicate a possible variation of ±10% in a stated numeric value.

As described above, existing auto-injectors often require multiple user interactions to self-administer a drug, including, e.g., separate user interactions for deploying a needle and subsequently retracting the needle after drug delivery. These additional steps can increase complexity of self-administration of drugs, introduce user errors, and cause user discomfort. Accordingly, the present disclosure is directed to various embodiments of an injection device (e.g., auto-injector) that simplifies self-administration of drugs, or other therapeutic agents, by a user. Specifically, according to certain embodiments, the auto-injector may not require any additional user interaction to withdraw a needle once the needle is subcutaneously inserted into the user. Thus, auto-injectors of the present disclosure are simplified to help prevent misuse or user error.

Overall System

An example of such an auto-injector 2 is shown in FIGS. 1-4. Auto-injector 2 may include a housing 3 having a tissue-engaging (e.g., bottom) surface 4 through which a needle may be deployed and retracted via an opening 6 (FIG. 2). An activating switch 1409 (FIG. 2) may be disposed on tissue-engaging surface 4, and may be configured to activate auto-injector 2, or otherwise place auto-injector 2 in a "ready" mode. A touch sensor 1410 (FIG. 2) also may be disposed on tissue-engaging surface 4, and may be configured to help a controller of auto-injector 2 determine whether auto-injector 2 is disposed on the skin of a user (indicating that the auto-injector should fire or otherwise deploy a needle), or whether activating switch 1409 was improperly triggered (indicating that operation of auto-injector 2 should be stopped). Activating switch 1409 and touch sensor 1410 will be discussed in further detail below with respect to FIG. 4A. A connecting port 13 also may be disposed on tissue-engaging surface 4 to facilitate programming of auto-injector 2. Housing 3 may include a transparent window 50 to enable a viewer to visualize one or more displays or LEDs 52 (referring to FIG. 4B) disposed within housing 3, and also may include a plurality of openings 51 configured to facilitate the travel of sound generated within housing 3 (by, e.g., a speaker). The LEDs 52 may be arranged in a ring-like formation, or any other suitable formation. Auto-injector 2 may have any suitable dimensions suitable to enable portability and self-attachment by a user. In one example, auto-injector 2 may have a length of about 2.98 inches, a width of about 2.07 inches, and a height of about 1.07 inches. However, other suitable values also may be utilized, including, e.g., a length from about 0.5 inches to about 5.0 inches, a width of about 0.5 inches to about 3.0 inches, and a height from 0.5 inches to about 2.0 inches.

Auto-injector 2 may be oriented about a longitudinal axis 40 (e.g., an X axis), a lateral axis 42 (e.g., a Y axis) that is substantially perpendicular to longitudinal axis 40, and a vertical axis 44 (e.g., a Z axis) that is substantially perpendicular to both longitudinal axis 40 and lateral axis 42.

An adhesive patch 12 may be coupled to tissue-engaging surface 4 to help secure auto-injector 2 to a user's body (e.g., skin). Adhesive patch 12 may be formed from fabric or any other suitable material, and may include an adhesive. The adhesive may be an aqueous or solvent-based adhesive, or may be a hot melt adhesive, for example. Suitable adhesives also include acrylic based, dextrin based, and urethane based adhesives as well as natural and synthetic elastomers. In some examples, the adhesive provided on patch 12 may be activated upon contact with a user's skin. In yet another example, patch 12 may include a non-woven polyester substrate and an acrylic or silicone adhesive. Patch 12 may be joined to housing 3 by, e.g., a double-sided adhesive, or by other mechanisms like ultrasonic welding. Patch 12 may have a length dimension greater than a width of auto-injector 2.

Needle Mechanism

Figure 7:
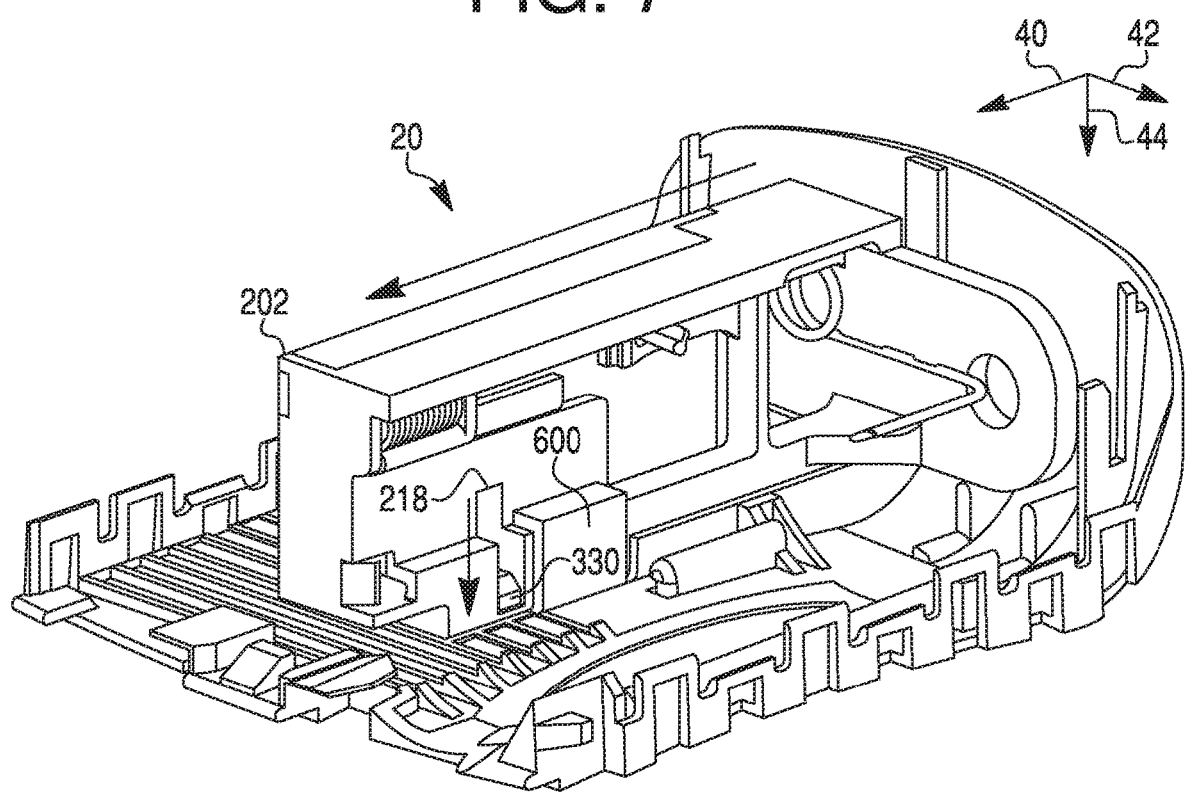

Referring to FIGS. 5-11, a needle mechanism 20 includes a carrier 202 that is movable (e.g., slidable) within housing 3 between a first position (FIG. 6) and a second position (FIG. 7). Needle mechanism 20 also may include a fluid conduit 300 that is mounted to carrier 202, and which may be deployed into a user, and retracted by a driver 320. A shuttle 340 (e.g., a shuttle actuator) may be configured to move driver 320 via a deployment gear 360, and a retraction gear 362. Shuttle 340 may be coupled to a resilient member (e.g., a spring 370). A cover 380 (FIG. 5) may be coupled to carrier 202 to enclose various components of needle mechanism 20.

Referring to FIG. 5, fluid conduit 300 may extend from a first end 302 to a second end 304. First end 302 may include a needle 306 that is configured to be injected into a user. Needle 306 may include a sharp and/or beveled tip, and may extend generally along or parallel to axis 44. Second end 304 may include a needle 308 that is substantially similar to needle 306, but may be positioned within auto-injector 2 to penetrate a vial 1302 (shown in FIG. 13 and described in further detail below) to access drugs to be injected into the user. Fluid conduit 300 may include an intermediate section 310 including one portion extending along or parallel to axis 40, and a second portion extending along or parallel to axis 40. The first and second portions of intermediate section 310 may be joined in a coil 312 that facilitates flexion of fluid conduit 300 and movement of needle 306 along axis 44 during deployment into the user, and during retraction out of the user. While a coil 312 is shown, any other suitable shape, e.g., a serpentine, curved, or other shape that enables flexion of fluid conduit 300 is also contemplated. Coil 312, or similar structure, may act as a cantilever when needle 306 is deployed and/or retracted. Coil 312 also may bias fluid conduit 300 into the deployed configuration shown in FIG. 5. Once needle 308 penetrates and establishes fluid communication with vial 1302 (see, e.g., FIG. 14), drugs may travel from vial 1302, through needle 308, intermediate section 310, and needle 306 (pierced through the user's skin), and into the user. In some examples, fluid conduit 300 may include only metal or a metal alloy. In other examples, fluid conduit 300 may be include any other suitable material, such as, e.g., polymers or the like. Needle 308 and intermediate portion 310 may define a 22 or 23 Gauge, thin-walled needle, while needle 306 may be a 27 Gauge needle. Other needle sizes ranging from, e.g., 6 Gauge to 34 Gauge, also may be utilized as appropriate. Fluid conduit 300 may reduce the amount of material that contacts the drugs, reduce joints and assembly steps, and require less sterilization than conventional devices.

Carrier 202 may be formed of plastic (e.g., injection-molded plastic), a metal, metal alloy, or the like, and may include a flange 204 with an opening 206, and posts 210 and 212. Carrier 202 also may include an opening 216 through which a needle or other fluid conduit may be deployed. Opening 216 may be a slot that is recessed from an end surface of carrier 202, or, in an alternative embodiment, an entirety of the perimeter of opening 216 may be defined by material of carrier 202. Carrier 202 also includes a driver path 218. Driver path 218 may be a slot in carrier 202 that extends along or parallel to axis 44. Driver path 218 may be configured to receive a protrusion of driver 320, such as, e.g., protrusion 330 discussed in further detail below. Carrier 202 also may include a shuttle path 220, along which shuttle 340 may move, as described in further detail below.

Figure 8:
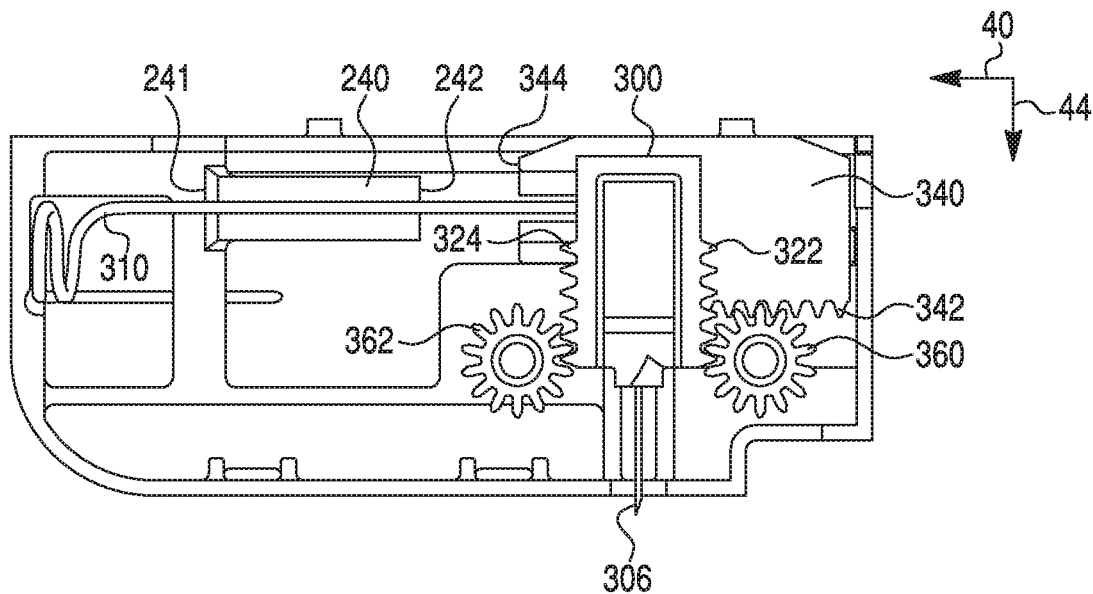

Carrier 202 also may include a stop 240 that is configured to engage shuttle 340. Stop 240 may be a cantilever having a fixed end 241 (FIG. 8) and a free end 242 (FIG. 8). Stop 240 may include an inclined ramp 243 (FIGS. 9 and 12) that, when engaged or pushed by a ramp 1500 (described with reference to FIG. 12), causes stop 240 to deflect about fixed end 241. In a first position, free end 242 may block or otherwise impede movement of shuttle 340, and in a second configuration, may permit movement of shuttle 340. The relationship between stop 240 and shuttle 340 will be discussed in further detail later in the application.

Driver 320 includes two racks 322 and 324 (shown in FIG. 8) parallel to one another and disposed on opposing sides of driver 320. Racks 322 and 324 may include teeth and may be configured to engage with and drive rotation of deployment gear 360 and retraction gear 362, respectively. Driver 320 may include a lumen 326 (or a track, recess, or other suitable structure) (FIG. 5) that is configured to receive needle 306 of fluid conduit 300. Driver 320 also may include protrusion 330 (FIGS. 6 and 7) that is configured to slide within driver path 218 of carrier 202. Protrusion 330 may include a hook-like configuration that can "catch" on impediment 600, as described in further detail below.

With continuing reference to FIG. 5, shuttle 340 may include a rack 342 configured to engage with gears 360 and 362. Shuttle 340 also may include an end surface 344, and a recess 346 that extends along a length of shuttle 340 in the same direction as rack 342. A slot 348 (FIG. 9) may extend along the length of recess 346. Slot 348 may extend through the middle of recess 346 and may extend along an entirety or substantial entirety of recess 346.

Figure 10:
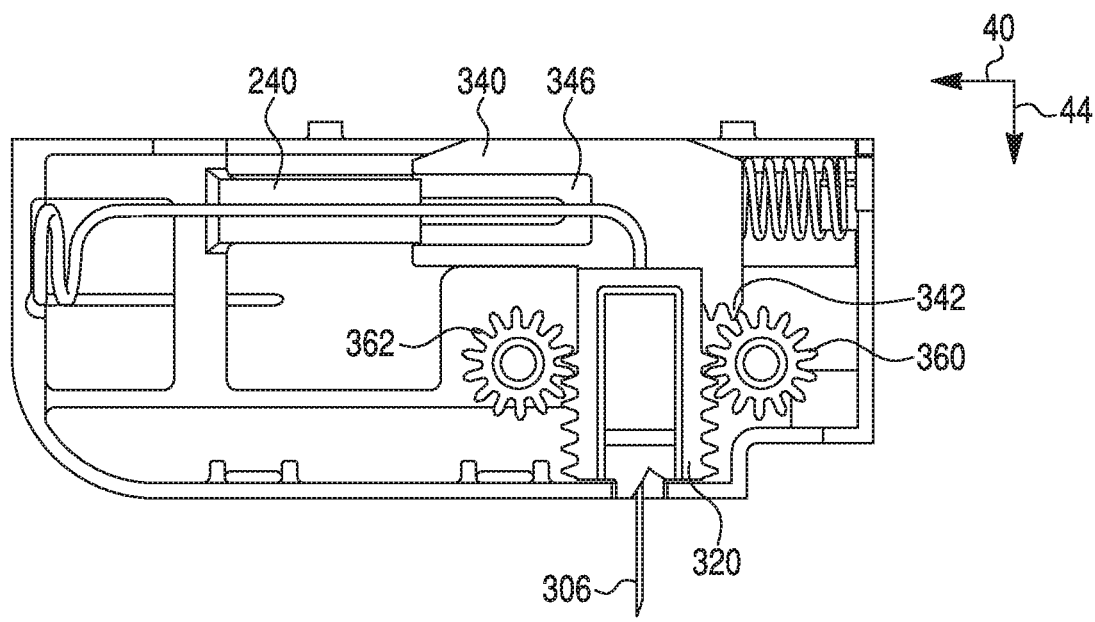
Figure 11:
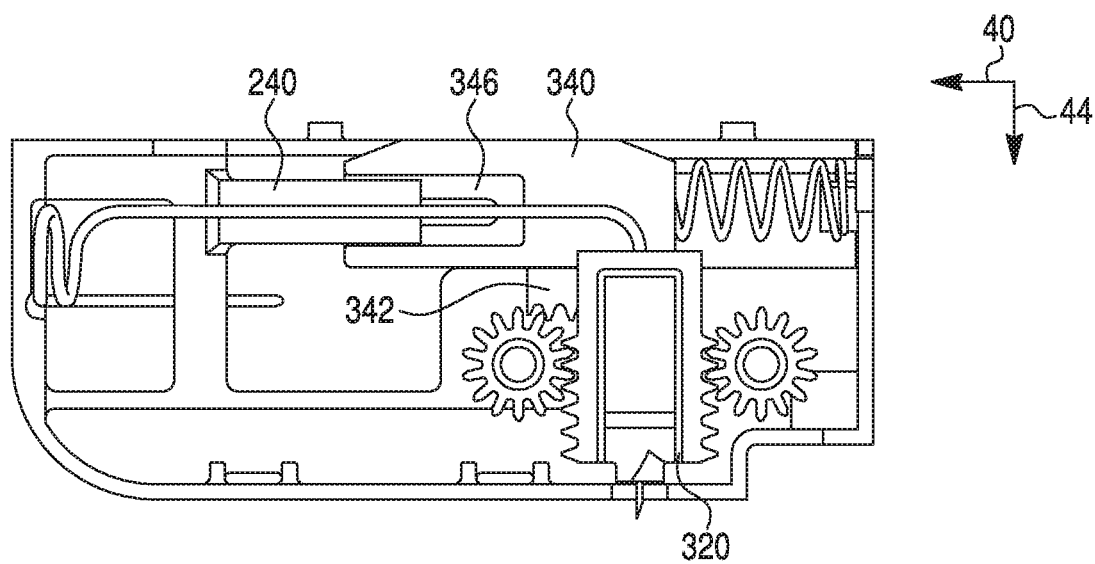

Shuttle 340 may move along track 220 from a first, starting position (FIG. 8), to a second, intermediate position (FIGS. 9 and 10), and from the second position to a third, final position (shown between the second and third configurations in FIG. 11). As shuttle 340 moves along track 220, rack 342 may first engage deployment gear 360, and then retraction gear 362. At certain times, rack 342 engages at most one of deployment gear 360 and retraction gear 362 at any given time. In some examples, such as when rack 342 is disposed longitudinally between deployment gear 360 and retraction gear 362, rack 342 is not engaged with either of deployment gear 360 and retraction gear 362. Shuttle 340 may be configured to move only along one axis (e.g., axis 40) and only in one direction along the one axis. The force required to move shuttle 340 along track 220 may be provided by expansion of spring 370. Spring 370 may be compressed from a resting state, and the expansion of spring 370 may move shuttle 340 along track 220 through the series of positions/configurations set forth above. At various positions of shuttle 340, different features of auto-injector 2 may directly or indirectly block movement of shuttle 340.

The first position of shuttle 340, shown in FIG. 8, may correspond to an unused, undeployed, and/or new state of auto-injector 2. In this first position, driver 320 may be in an undeployed state. Shuttle 340 is maintained in the first position by the positioning of an impediment 600 in the path of driver 320 (FIG. 6). Impediment 600, which may be a shelf of housing 3, or another suitable blocking device, may prevent movement of driver 320 by engaging and/or retaining protrusion 330. Therefore, because driver 320, deployment gear 360, and rack 342 are coupled to one another, the blockage of driver 320 also prevents movement of shuttle 340. Shuttle 340 may move from the first position to the second position by moving impediment 600 relative to carrier 202 (or vice versa). In one example, carrier 202 is moved (e.g., to the left in FIG. 6) while impediment 600 remains stationary.

When the path of driver 320 is free from impediment 600 (FIG. 7), spring 370 may expand and move shuttle 340 along track 220. This linear movement of shuttle 340 may rotate deployment gear 360 counter-clockwise (or clockwise in other examples) via rack 342, and the rotation of deployment gear 360 may move driver 320 downward along axis 44, via rack 322 of driver 320. This downward movement of driver 320 may cause needle 306 to pierce through the skin of a user. In some examples, driver 320 may be configured to move, relative to carrier 202, along only axis 44.

Figure 9:
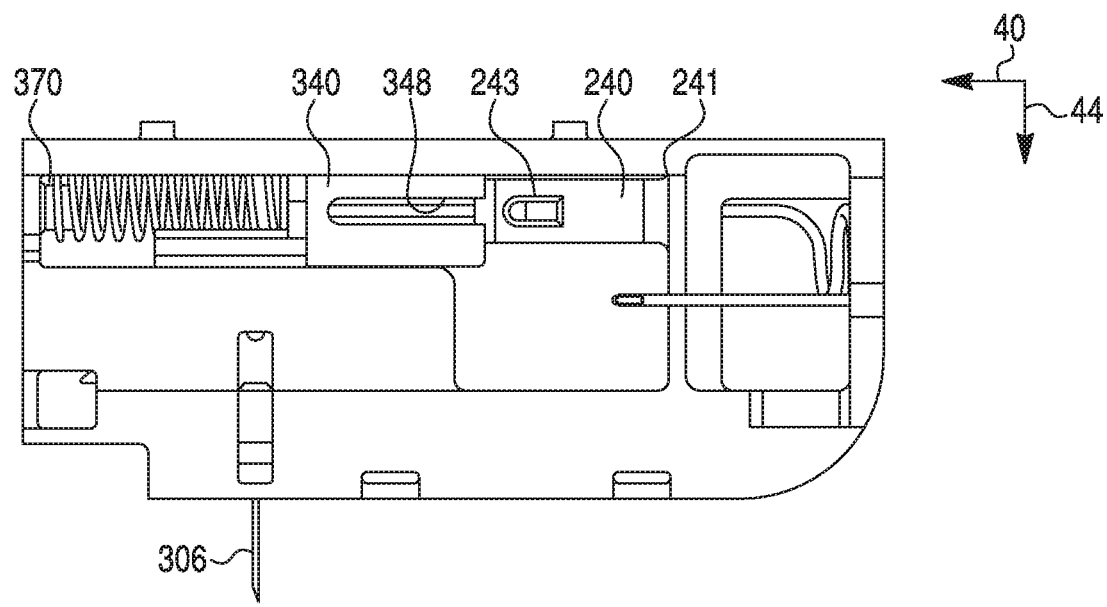

Shuttle 340 may be moved by the expansion of spring 370 until its end surface 344 abuts free end 242 of stop 240 such that shuttle 340 is maintained in the second position shown in FIGS. 9 and 10. At this point, free end 242 may prevent further expansion of spring 370 and further movement of shuttle 340 along track 220. In this second position, fluid conduit 300 may be deployed within a user, and fluid from vial 1302 may be injected into the user via needle 306. Additionally, while shuttle 340 is in the second position, rack 342 may be engaged with deployment gear 360 to maintain needle 306 in the deployed configuration. Shuttle 340 may move from the second position to the third position by the flexion of stop 240 about its fixed end 241. Further details of this flexion are set forth below with respect to FIGS. 12-14. The flexion of stop 240 may allow spring 370 to continue expanding, urging shuttle 340 further along track 220. In some examples, stop 240 may be received by and/or within recess 346 of shuttle 340, and ramp 243 may slide within slot 348, as shuttle 340 moves from the second position to the third position.

The movement of shuttle 340 from the second position to the third position may correspond to the retraction of needle 306 from the user into housing 3. In particular, rack 342 may engage with and rotate retraction gear 362 in the same direction (e.g., counter-clockwise or clockwise) as deployment gear 360 was rotated. The rotation of retraction gear 362 may urge driver 320 back to a retracted position via rack 324. Shuttle 340 may reach the third position, where driver 320 is fully-retracted, when its end surface 344 engages a wall of carrier 202, when free end 242 of stop 240 reaches an end of recess 346, and/or when spring 370 reaches a resting state.

In some embodiments, once driver 320 moves from the deployed state back to the retracted state, it may be prevented from moving out of the retracted state. As a result, needle 306 will be prevented from re-deployment into the user. In this configuration, auto-injector 2 may be a single-use device (e.g., discarded after completing one injection). In other embodiments, auto-injector 2 may be reset and reused. Furthermore, deployment gear 360 and retraction gear 362 may be the only rotating gears disposed within auto-injector 2, in some examples.

Piercing System and Sterile Connector

FIGS. 13 and 14 show features of a piercing system 1300 of auto-injector 2. Additional details of exemplary piercing systems can be found in U.S. Patent Application Publication No. 2016/0262984 A1 to Arnott et al., published on Sep. 15, 2016, the entirety of which is incorporated by reference herein. Piercing system 1300 includes a primary container, chamber, syringe, cartridge, or vial 1302 with a first end 1304 and a second end 1306. Vial 1302 also may include a cavity 1308 opened at first end 1304 and extending toward second end 1306. Second end 1306 may include a neck 1310 with a cap 1312 that engages neck 1310 to close second end

1306. A septum 1314 may be positioned between vial 1302 and cap 1312 to assist with closing second end 1306, and allow for needle 308 (e.g., a staked needle) to be inserted into vial 1302. Cavity 1308 may be closed at first end 1304 by a piston 1316.

Vial 1302 may have a 5 mL capacity in some examples, although any other suitable volume (e.g., from 1 mL to 50 mL, or from 2 mL to 10 mL, or from 3 mL to 6 mL, or from 2 mL to 5 mL, or another suitable range) also may be utilized depending on the drug to be delivered. In other examples, vial 1302 may have a capacity greater than or equal to 1 mL, or greater than or equal to 2 mL, or greater than or equal to 3 mL, or greater than or equal to 4 mL, or greater than or equal to 5 mL. Vial 1302 may contain and preserve a drug for injection into a user, and may help maintain sterility of the drug. Vial 1302 may have a 13 mm diameter neck, a 45 mm length, and an internal diameter of 19.05 mm. These values are merely exemplary, and other suitable dimensions may be utilized as appropriate. In some examples, vial 1302 may be formed using conventional materials, and may be shorter than existing devices, which can help auto-injector 2 remain cost-effective and small. Vial 1302 may be a shortened ISO 10 mL cartridge.

Septum 1314 may include an uncoated bromobutyl material, or another suitable material. Piston 1316 may include a fluoropolymer coated bromobutyl material, and also may include a conical nose 1316a to help reduce dead volume within vial 1302. Piston 1316 may include one or more rubber materials such as, e.g., halobutyls (e.g., bromobutyl, chlorobutyl, florobutyl) and/or nitriles, among other materials.

Piercing system 1300 also may include a top 1354 positioned at second end 1306. Top 1354 may include a base 1355 positioned over septum 1314 and the opening of vial 1302. Top 1354 may include a chamber 1356 extending from base 1355 in a direction away from piston 1316. Chamber 1356 defines a cavity 1357 and includes an opening 1358 in communication with cavity 1357. In some embodiments, top 1354 may be integrated with septum 1314 (e.g., integral or of one-piece construction). In alternative embodiments (not shown), top 1354 may be provided or initially assembled on fluid conduit 300 and not installed directly on/with vial 1302 and/or integrated with septum 1314.

A portion of fluid conduit 300, such as needle 308, a tube or the like, may extend through opening 1358 of chamber 1356 and into cavity 1357, but not through base 1355 in the pre-activated state. Opening 1358 may be pre-formed, or may be formed by the penetration of needle 308 through chamber 1356. Opening 1358 of chamber 1356 may form a sterile sliding seal about needle 308 such that pathogens or other contaminants are prevented from passing into cavity 1357. Needle 308 can move relative to top 1354 without disrupting the sterile seal therebetween. Cavity 1357 may be sterile or aseptic such that the inner surfaces of cavity 1357 and needle 308 are sterile. In another embodiment, cavity 1357 may be sterilized after needle 308 is inserted through opening 1358 and into cavity 1357. In alternative embodiments, rather than top 1354, a convoluted flexible (e.g., rubber) bellows or bladder member may form cavity 1357 and allow translation of vial 1302 relative to needle 308 (or vice versa). The flexible member also may seal or form cavity 1354 about needle 308 after sterilization.

In an alternative embodiment shown in FIG. 14A, a top 1354a may be used with piercing system 1300 in lieu of top 1354. Top 1354a may include a plug 1356a and a base 1355a positioned over the opening of vial 1302. Plug 1356a may extend from base 1355a in a direction away from piston 1316. In the pre-activated state, needle 308 may be disposed within plug 1356a. Plug 1356a may be a solid plug which is devoid of any holes, cavities, or openings, and which may be formed of a first rubber material. The first rubber material may be permeable to a sterilizing gas, such as, e.g., ethylene oxide or vaporized hydrogen peroxide. The first rubber material may include one or more of isoprene, ethylene propylene diene monomer (M-class) rubber (EPDM), and styrene-butadiene, among others. The permeability of the first rubber material to a sterilizing gas may allow needle 308, which is disposed within the plug 1356a, to be sterilized before use. Plug 1356a may be molded about needle 308, so that needle 308 is impaled into plug 1356a. The impermeability of base 1355a to the sterilizing gas may prevent contamination and/or alteration of a drug contained within vial 1302. Base 1355a may include impermeable rubbers such as, e.g., halobutyls (e.g., bromobutyl, chlorobutyl, florobutyl) and/or nitriles, among other materials.

Piston 1316 may be coupled to a translation mechanism 1366 that is configured to translate piston 1316 and vial 1302 in a direction toward second end 1306. The movement of piston 1316 toward second end 1306 causes piston 1316 to act against the contents within vial 1302 (e.g., drugs, medications), which ultimately transfers force against second end 1306 of vial 1302, causing vial 1302 to move along longitudinal axis 40. Translation mechanism 1366 may include a 12 mm motor 1367 with a five-stage gear reduction (360:1). Translation mechanism 1366 may have spring contacts that create an electrical connection with an associated printed circuit board (e.g., first electronic board 1402). The motor 1367 may be configured to generate a torque of about 136 mN*m at 36 rpm. These design parameters of the motor 1367 are merely exemplary, and any other suitable motor also may be utilized.

Translation mechanism 1366 may include a leadscrew mechanism coupled to piston 1316 that extends axially upon relative rotation about longitudinal axis 40. This telescoping leadscrew may have a 100 N output, a 20 mm stroke, and a 7°/45° buttress thread shape with a 0.75 mm pitch. The materials for the leadscrew mechanism may include acetal and polybutylene terephthalate. The leadscrew mechanism may extend within piston 1316 to reduce dead space behind piston 1316. While piston 1316 is shown in FIGS. 13 and 14 with longitudinally spaced threads, in some examples, such threads may not be present. In another exemplary embodiment (not shown), translation mechanism 1366 may include a manually engageable surface or member that is manually manipulated by a user to move piston 1316. For example, piercing system 1300 may include a cartridge or a plunger coupled to the back side of piston 1316. In another exemplary embodiment (not shown), translation mechanism 1366 may include a pneumatic or hydraulic drive member that is actuated or initiated by a user to move piston 1316. The drive member may be in the form of expanding bellows, an expanding bladder, an expanding diaphragm, or a sliding seal or piston, for example. The direct pneumatic or hydraulic pressure may provide the force required to move piston 1316.

Piercing system 1300 also includes a collar 1390 coupled or fixed to second end 1306. Collar 1390 may include a plurality of circumferentially spaced apart fingers 1392 that engage and surround neck 1310. Collar 1390 may be fixed, or otherwise coupled to second end 1306. Collar 1390 may include a wall 1390a that extends at least partially about neck 1310, the opening of second end 1306, cap 1312, septum 1314, and/or top 1354. Wall 1390a of collar 1390 may be positioned radially or laterally outward of neck 1310 and extend longitudinally past neck 1310, cap 1312, and septum 1314.

In the pre-activated state of piercing system 1300 shown in FIG. 13, an edge 1393 of collar 1390 may engage a corresponding radially or laterally inwardly extending cam, latch or actuation portion 1394 of a driver retainer member 1395. Retainer member 1395 may be slidable relative to collar 1390. Collar 1390 and retainer member 1395 may be configured such that in the pre-activated state or arrangement shown in FIG. 13, at least a portion of the cam or actuation portion 1394 of retainer member 1395 is positioned directly behind a retaining portion 1399 of a driver 1398 slidable within retainer member 1395. A wall 1391 of driver 1398 may extend into and through an end cap portion 1396 of retainer member 1395 and into an interior portion of retainer member 1395, and retaining portion 1399 of driver 1398 may extend radially outward from wall 1391. In some embodiments, wall 1391 of driver 1398 may be substantially cylindrical and retaining portion 1399 of driver 1398 may be a flange extending about an end of the wall 1391.

In the pre-activated state of piercing system 1300, an elastically deformed biasing or resilient member 1397 may be positioned between cap portion 1396 of retainer member 1395 and retaining portion 1399 of driver 1398. Biasing member 1397 may exert a force against driver 1398 in the pre-activated state of piercing system 1300 acting in the direction towards vial 1302. Biasing member 1397 may be any member effective in applying the force in the pre-activated state, and then releasing such force upon activation, as discussed below with reference to FIG. 14. In some embodiments, biasing member 1397 may be a conical or flat spring.

Needle 308 of fluid conduit 300 may be fixed or coupled to driver 1398 such that fluid conduit 300 moves with driver 1398. In the pre-activated state of piercing system 1300, needle 308 may be positioned within the sterile cavity 1357, but not through base 1355 of top 1354, septum 1314, and/or into cavity 1308 of vial 1302.

To move piercing system 1300 from the pre-activated state of FIG. 13, translation mechanism 1366 may be activated to move piston 1316 towards second end 1306 and translate vial 1302 along longitudinal axis 40 toward driver 1398. Because the needle 308 is not yet in fluid communication with vial 1302, activation of translation mechanism 1366 applies a pressure against the fluid contained in vial 1302, which is then applied to vial 1302 itself. This pressure also causes edge 1393 to push against and deflect actuation portion 1394 radially outward. Without actuation portion 1394 blocking its path, retaining portion 1399 and needle 308 are moved toward vial 1302 by the expansion of biasing member 1397. Driver 1398 may be coupled to flange 204 of carrier 202, and thus, this movement of driver 1398 toward vial 1302 also may move carrier 202 in the same direction. This movement corresponds to the movement of carrier 202 relative to housing 3 in FIGS. 6 and 7, which enables protrusion 330 to clear impediment 600 to inject needle 306.

The movement of needle 308 toward second end 1306 of vial 1302 also causes needle 308 to pierce through base 1355 of top 1354, septum 1314, and cavity 1308, into fluid communication with the contents of vial 1302. Once needle 308 is in fluid communication with vial 1302, further movement of piston 1316 toward second end 1306 urges fluid through needle 308 and a remainder of fluid conduit 300. In some embodiments, piercing system 1300 may be configured such that, after activation, no more of needle 308 than the portion that was already positioned within sterile cavity 1357 extends into cavity 1308. This may help prevent contamination of the contents of vial 1302 with non-sterile portions of needle 308.

Biasing member 1397 may be configured to expand such that fluid conduit 300 pierces top 1354 and/or septum 1314 at a high speed, such as at a speed of at least about 10 mm/sec, or at least about 40 mm/sec. The relatively quick piercing of top 1354 and/or septum 1314 via biasing member 1397 may help prevent leakage of the contents of cavity 1308 which may be under pressure via piston 1316.

After drugs have been delivered to the user via needle 306, needle 306 may be automatically withdrawn from the user. Referring to FIGS. 12-14, translation mechanism 1366 may be operated in a reverse mode such that the rotation of the lead screw is in an opposite direction compared to the insertion step. This counter-rotation may cause piston 316 to move back toward first end 1304, and also cause vial 1302 to move in an opposite direction along axis 40 (as compared to during fluid delivery and insertion of needle 306). The movement of vial 1302 in the opposing direction may cause ramp 1500 in FIG. 12 (which is attached to wall 1391) to push against ramp 243 of stop 240. This may cause stop 240 to deflect about its fixed end 241 in the direction of arrow 240*a*, and allow shuttle 340 to move from its second position to its third position to retract needle 306 as set forth above. in this way, withdrawal and insertion of the needle into a patient can both be accomplished with a single spring within the device.

It is further contemplated that fluid conduit 300 may be the only fluid conduit of auto-injector 2 configured to be in fluid communication with vial 1302. Thus, drugs from vial 1302 may be deployed only through fluid conduit 300 and into the user during normal operation of auto-injector 2. Additionally, needle 306 may be the only needle of auto-injector 2 configured to be deployed into a patient. In this way, a single piece of metal or plastic can be used to carry the fluid from vial 1302 to a patient.

Sterile Needle Shield

Referring to FIGS. 24 and 25, auto-injector 2 may include a needle cover or a needle shield 2400 that is configured to help maintain sterility of needle 306. Needle shield 2400 may extend from a first end 2402 toward a second end 2404. A flange 2406 may be disposed at first end 2402, and a tubular extension 2408 may extend from flange 2406 toward second end 2404. Needle shield 2400 may include an opening 2410 through flange 2406, which may be in communication with a lumen 2412 extending through extension 2408. A seal 2414 may be disposed at second end 2404 within lumen 2412. Seal 2414 may define an opening 2416 that is in communication with a remainder of lumen 2412. Seal 2414 may include a constricted portion 2414*a*, an intermediate portion 2414*b*, and an inner sealing portion 2414*c*. Intermediate portion 2414*b* may be disposed between constricted portion 2414*a* and inner sealing portion 2414*c*, and of the three components, constricted portion 2414*a* may be disposed closest to second end 2404. Intermediate portion 2414*b* may have a larger inner diameter than constricted portion 2414*a*, and constricted portion 2414*a* may have a larger inner diameter than inner sealing zone 2414*c*. Needle shield 2400 also may include a membrane 2418 that covers opening 2410 in flange 2406. Membrane 2418 may be formed from a gas-permeable material that is not permeable to liquids, such as, e.g., a high-density polyethylene fiber membrane. In one example, membrane 2418 may be Tyvek® brand material. Membrane 2418 may help keep seal 2414 sterile, so that seal 2414 does not contaminate needle 306 when needle shield 2400 is disengaged from housing 3.

Flange 2406 and extension 2408 may be formed from a plastic or other suitable material, while seal 2414 is formed from a rubber material. In another embodiment, flange 2406 and extension 2408 also may be formed from rubber. The rubber material may be substantially similar to the material forming plug 1356*a* set forth above. For example, the rubber material forming flange 2406, extension 2408, and seal 2414 may be permeable to a sterilant or a sterilizing gas, such as, e.g., ethylene oxide or vaporized hydrogen peroxide. The rubber material may include one or more of isoprene, ethylene propylene diene monomer (M-class) rubber (EPDM), styrene-butadiene, and thermoplastic elastomers (TPE), among others. In one embodiment, when flange 2406 is formed from a sterilant-permeable rubber material, flange 2406 may not include an opening 2410, and instead may be a solid plug of material.

Needle shield 2400 may be coupled with auto-injector 2 in order to maintain sterility of needle 306 during, e.g., shipping of auto-injector 2 before use. During this coupling, needle 306 may pierce through inner sealing portion 2414*c* of seal 2414, so that seal 2414 forms a seal around needle 306. That is, inner sealing portion 2414*c* initially may be a closed and pierceable membrane. Alternatively, inner sealing portion 2414*c* may be a constricted portion having a smaller inner diameter than constricted portion 2414*a*, and needle 306 may slide through this smaller constricted portion. The pierced portion (inner sealing portion 2414*c*) of seal 2414 may be relatively thin, so that it does not significantly dull needle 306. Constricted portion 2414*a* may engage with and form a seal around a portion of intermediate section 310 of conduit 300. Intermediate section 310 may have a larger outer diameter than an outer diameter of needle 306. Additionally, a volume or gap 2414*d* may be formed between an inner diameter of intermediate portion 2414*b* and the outer diameter of intermediate section 310.

Auto-injector 2 may be sterilized via exposure to a sterilizing gas (e.g., ethylene oxide) after needle shield 2400 is coupled to auto-injector 2. Both lumen 2412 and gap 2414*d*, surfaces defining lumen 2412 and gap 2414*d*, and components contained therein (such as, e.g., exposed portions of needle 306 that pierce through tissue of a patient/user) may be sterilized after exposure to the sterilizing gas. A user may be instructed to manually remove needle shield 2400, for example, by pulling needle shield 2400 away from housing 3. In another embodiment, needle shield 2400 may be integrated with a packaging of auto-injector 2, such that, when auto-injector 2 is removed from the packaging, needle shield 2400 is removed from auto-injector 2. For example, flange 2406 may be secured to the packaging (not shown) by an adhesive. Then, when the user withdraws auto-injector 2 from the packaging, needle shield 2400 will disengage from housing 3, so that needle 306 can be freely deployed in the normal operation of auto-injector 2. In some cases, exposed portions of seal 2414 closer to second end 2404 than constricted portion 2414*a* (and/or constricted portion 2414*a* itself) may become contaminated after sterilization. Thus, it may be important that these contaminated surfaces do not contact needle 306 during withdrawal of shield 2400 from auto-injector 2. The narrower inner diameter of inner seal portion 2414*c* helps ensure that these potentially contaminated portions do not contact needle 306, particularly those portions of needle 306 that are inserted into tissues of a patient/user, by keeping extension 2408 of shield 2400 centered upon removal.

In an alternative embodiment, seal 2414 may be directly coupled to driver 320. In this embodiment, seal 2414 may seal against a plastic or other portion of extension 2408, and would remain within auto-injector 2 when needle shield 2400 is removed.

Electronics

FIG. 4A shows a control system 1400 of auto-injector 2. Control system 1400 may include components positioned on a first electronics board 1402 and a second electronics board 1404, and also may include a power source 1406. First electronics board 1402 may include a controller 1408, an activating switch 1409, a touch sensor 1410, a needle insert switch 1412, and an emitter 1414. Second electronics board 1404 may include a detector 1416, an audio module 1418, a visual module 1420, and a haptic module 1422. One or more of the components of first electronics board 1402 and second electronics board 1404 may be operatively coupled to controller 1408, and powered by power source 1406. Controller 1408 also may be operatively coupled to translation mechanism 1366, and may be configured to control operation of translation mechanism 1366 to initiate and control needle insertion and retraction as set forth above. Translation mechanism 1366 may be coupled to first electronics board 1404 via one or more spring contacts during a final assembly step where vial 1302 is inserted into housing 3.

The majority of the assembly of auto-injector 2 may occur, e.g., on an assembly line at a manufacturing facility. Then, two device halves (or portions) may be shipped to a drug filling or final assembly facility. Indeed, the two separate portions 1490 and 1492 need not be the same size, as illustrated in FIG. 4B. Once a drug vial, e.g., vial 1302, is filled with a drug or other medicament, vial 1302 may be assembled with a remainder of auto-injector 2. For example, the two device halves (portions 1490 and 1492) may be assembled together with the filled drug vial 1302 therein. In one example, portion 1490 and translation mechanism 1366 may be snapped in place behind vial 1302. Portion 1490 may be part of housing 3 including a base or module configured to contain translation mechanism 1366 and its associated electronics. Portion 1492 may be a part of housing 3 containing substantially all of the other components described herein, including, e.g., the needle mechanism, sterile connector, and piercing mechanisms described herein. In this example, an electrical connection of the motor of translation mechanism 1366 must be made during the snapping of translation mechanism 1366 behind vial 1302 (i.e., during the assembly step where portions 1490 and 1492, and vial 1302 are combined to form a complete and functional auto-injector 2). To accommodate such an electrical connection, the drivetrain of translation mechanism 1366 may include one or more spring contacts 1494 (referring to FIG. 4C) that will contact pads 1495 (also referring to FIG. 4C) on the first electronics board 1402 upon assembly. Thus, the connection of translation mechanism 1366 to first electronics board 1402 (including controller 1408) may be made without any loose wires or other similar structures.

Such an assembly process may be relatively simpler than simpler devices (e.g., auto-injectors) with relatively more complex final assembly processes. As a result, the contemplated assembly process described herein may lead to a reduction of labor costs.

Controller 1408 may be configured to accept information from the system and system components described above, and process the information according to various algorithms to produce control signals for controlling translation mechanism 1366. The processor may accept information from the system and system components, process the information according to various algorithms, and produce information signals that may be directed to audio module 1418, visual module 1420, haptic module 1422, or other indicators of, e.g., second electronics board 1404, in order to inform a user of the system status, component status, procedure status or any other useful information that is being monitored by the system. The processor may be a digital IC processor, analog processor or any other suitable logic or control system that carries out the control algorithms.

As discussed above with respect to FIGS. 2 and 3, activating switch 1409 may be a mechanical plunger-type switch that extends away from tissue-engaging surface 4 of auto-injector 2. Activating switch 1409 may include an electrical circuit that is broken unless activating switch 1409 is depressed. For example, when auto-injector 2 is attached to a user's skin, switch 1409 may be depressed, completing the electrical circuit, and indicating to controller 1408 that auto-injector 2 should be activated. In order to conserve power, the components of auto-injector 2 may be in an idle or sleep mode until switch 1409 is activated. In yet another example, auto-injector 2 may not be powered at all until switch 1409 is activated, and deactivation of switch 1409 may cut off power to auto-injector 2 entirely. While a mechanical plunger-type switch is disclosed, any other suitable mechanism for activating auto-injector 2 may be utilized, including, e.g., a button depressed by the user, voice signals, a wireless signal from another electronic device, among others.

Touch sensor 1410 may be configured to help controller 1408 determine whether auto-injector 2 is properly deployed on the skin of a user. In one example, touch sensor 1410 may be a capacitive sensing electrode or any other device configured to differentiate contact with skin versus other materials, such as, e.g., wood, plastic, metal, or another material. When skin is in the proximity of the capacitive sensing electrode, a signal indicative of such contact may be sent to controller 1408. Thus, touch sensor 1410 may serve to verify that auto-injector 2 is properly placed on a user's skin, even if switch 1409 is depressed. Touch sensor 1410 may include a capacitive sensing electrode coupled to first electronics board 1402 and also to an interior of housing 3. Housing 3 and adhesive patch 12 may act as an overlay (insulator) that acts as a dielectric between the skin of the user and the capacitive sensing electrode. Contact of portions of housing 3 and/or adhesive patch 12 near the capacitive sensing electrode may cause the capacitance of the electrode to increase, for example, by about 1 to about 10 pF, indicating placement of auto-injector 2 on a skin surface.

Needle insert switch 1412 may be configured to send a signal to controller 1408 that needle 306 is deployed within a user. For example, referring to FIG. 15, needle insert switch 1412 may include a curved cantilever 1510 including a first contact 1512. Needle insert switch 1412 also may include a second contact 1514. First contact 1512 may be placed into electrical contact with second contact 1514 when needle 306 is deployed into the user. During deployment of needle 306, driver 320 may move downward along axis 44 and deflect curved cantilever 1510 and first contact 1512 toward second contact 1514. When first contact 1512 and second contact 1514 connect to one another, a signal may be sent to controller 1408 indicating that needle 306 has been successfully deployed into the user. The separation of first contact 1512 and second contact 1514 may indicate that needle 306 has been retracted from the user.

Emitter 1414 and detector 1416 may operate as an optical interruption sensor, or photo-interrupter in order to allow controller 1408 to determine a state of auto-injector 2. Emitter 1414 may be a light emitting diode (LED) or other suitable light emitter, and detector 1416 may be, e.g., a phototransistor configured to receive light emitted by emitter 1414. In one example, emitter 1414 may emit infrared light, although other suitable wavelengths of light also may be used. The use of infrared light may help reduce interference from external light. Emitter 1414 and detector 1416 may be arranged across from one another within housing 3 to enable a beam of light 1430 to pass from emitter 1414, through vial 1302, to detector 1416. Vial 1302, and any fluid contained therein may be at least partially transparent to beam 1430 so that beam 1430 may pass through vial 1302 and its contents. As piston 1316 is moved toward second end 1306 during drug delivery (referring to FIGS. 13 and 14), piston 1316, and in particular a shoulder of piston 1316, may interrupt beam 1430. When detector 1416 fails to sense beam 1430, a signal may be sent to controller 1408, which may interpret the signal to indicate an end of an injection (e.g., that all of the drug contained within vial 1302 has been expelled). In some examples, the refraction path of beam 1430 may be considered when positioning emitter 1414 and detector 1416 relative to one another. For example, beam 1430 may be refracted as it passes through vial 1302 and any liquid contained therein, and emitter 1414 and detector 1416 may be offset from one another accordingly. Additionally, emitter 1414 and detector 1416 may be offset from a center of housing 3 so that the shoulder of piston 1316 may block beam 1430. In at least some examples, an optical interruption sensor or similar mechanism may help avoid false positives in the event of a drive train failure. That is, the optical switch may help controller 1408 determine that an injection was not completed with greater accuracy than other mechanisms.

Audio module 1418 may include a speaker or the like to provide audio feedback to the user. Openings in housing 3 may facilitate the travel of sound from audio module 1418 to the user. Audio module 1418 may generate a tone or other sound at the start and at the end of injection, and/or to indicate any other benchmark during the injection. Visual module 1420 may include one or more LEDs or similar devices to provide visual feedback to the user. Visual module 1420 may include different colored LEDs to provide various messages to the user. For example, a plurality of green LEDs arranged in a ring could be used to display progress of the injection over time, while a red LED could be used to display an error to the user. Any other suitable colors, combinations, and/or numbers of LEDs may be used in various examples. For example, a combination of red, blue, and purple LEDs may be utilized. In one arrangement, sixteen LEDs may be arranged in a circle having a diameter of about 26.5 mm, or a diameter from about 10.0 mm to about 40.0 mm. The LEDs may be activated sequentially around the circle to indicate progress of an injection (e.g., in a progress ring arranged in a similar manner as a clock—see, for example, LEDs 52 on FIG. 4C). Controller 1408 also may be configured to receive feedback from various sensors, and rescale a speed that various LEDs are activated based on feedback from the sensors. For example, the LEDs in the progress ring may be activated in three or more operation phases including, e.g., an injection sequence activation phase, an injection phase, and a retraction phase. Those of ordinary skill in the art will recognize that auto-injector 2 may have more or less than the above-described three operation phases. There may be an expected time for completing each phase, but there also may be some variability in the actual times experienced during any of the aforementioned operation phases of auto-injector 2. An algorithm may be utilized to help avoid the premature activation of LEDs, for example, when a certain phase finishes earlier than expected, or to have progress along the ring stopped when a certain phase takes longer than expected. At any given point, the algorithm may divide the remaining estimated time for completion of drug delivery by the number of unactivated LEDs in the progress ring, to determine a rate at which the remaining LEDs in the progress ring should be activated.

For example, before the injection sequence activation phase, the LEDs may be activated at a rate equal to the estimated time of the entire drug delivery process (e.g., the estimated time to complete all of injection sequence activation phase, the injection phase, and the retraction phase) divided by the total number of unactivated LEDs in the progress ring. Stated differently, the estimated time of the entire drug delivery process may be divided by a number that is the total number of LEDs in the progress ring less any already-activated LEDs. Thus, if, for example, one LED is already activated, the estimated time of the entire drug delivery process may be divided by one less than the total number of LEDs in the progress ring.

After completion of the injection sequence activation phase, the LEDs may be activated at a rate equal to the sum of estimated times for completing the remaining phases (e.g., the injection phase and the retraction phase) divided by the number of unlit LEDs in the progress ring. After completion of the injection phase, the LEDs may be activated at a rate equal to the estimated time to complete the retraction phase, divided by the number of unlit LEDs.

Visual module 1420 also may include a display screen, touch screen, or other suitable device to provide one-way or two-way communication with the user. Visual module 1420 may be visible by the user from outside of housing 3 via a window in housing 3. Haptic module 1422 may include, e.g., a haptic motor configured to generate vibrations that can be felt by the user. Vibrations may signal the start and the end of an injection, and/or may help provide additional information to a user.

Controller 1408 may be coupled to a wireless communication module and an antenna. The wireless communication module may be configured to transmit data from controller 1408 to, e.g., a mobile device, computer, cell phone, or the like. The wireless communication module may be configured to transmit information over one or more wireless modalities, such as, e.g., Bluetooth, Bluetooth low energy (BLE), infrared, cellular networks, and wireless networks, among others. The antenna may be any suitable device configured to assist the wireless communication module in data transmission and/or amplification. Thus, controller 1408 may be configured to transmit diagnostic information of the user and/or auto-injector 2, information pertaining to completion of an injection, and/or information pertaining to an error state of auto-injector 2 to a device of the user, or to the cloud. Signals indicative of needle insertion and/or early device removal also could be transmitted via the wireless communication module. Controller 1408 also may receive activation and/or delay commands via the wireless communication module.

FIG. 16 shows an exemplary method 2000 according to the disclosure. Method 2000 may start at step 2002, where a user may position auto-injector 2 on her body so that tissue-engaging surface 4 contacts a skin surface. Auto-injector 2 may be mounted in any suitable location, such as, e.g., the thigh, abdomen, shoulder, forearm, upper arm, leg, buttocks, or another suitable location. Auto-injector 2 may be secured to the skin by adhesive patch 12. The securement of auto-injector 2 at step 2002 may cause activating switch 1409, which extends outward from tissue-engaging surface 4 to be depressed and complete a circuit. The completion of the circuit may cause a signal to be sent to controller 1408 to transition from a power-saving, sleep mode, to an active mode. Alternatively, any other suitable mechanism may power on or otherwise activate auto-injector 2 before or after step 2002.

Once auto-injector 2 is activated at step 2002, method 2000 may proceed to step 2004, where controller 1408 may determine whether tissue-engaging surface 4 is positioned on a skin surface. At step 2004, controller 1408 may receive a measurement from touch sensor 1410 indicating whether auto-injector 2 is positioned on skin or another surface. If controller 1408 determines that touch sensor 1410 is in contact with skin, for example, when a capacitance value received from touch sensor 1410 is within a predetermined range, method 2000 may proceed to step 2008. If controller 1408 determines that touch sensor is not in contact with skin, for example, if the capacitance measurement received from touch sensor 1410 indicates that auto-injector 2 is in contact with a non-skin surface like wood or metal, method 2000 may proceed to step 2006. At step 2006, auto-injector 2 may be placed into an error condition. In the error condition, an LED may be activated (e.g., a red LED) to indicate to the user that an error has occurred, or a message may be displayed on a display screen. In some examples, auto-injector 2 may need to be manually reset before an injection can be completed. In other examples, auto-injector 2 may loop back to step 2004, wherein controller 1408 continuously attempts to determine whether touch sensor 1410 is in contact with skin. Method 2000 also may require that touch sensor 1410 be in contact with skin during the entire injection. Thus, if at any point during the injection, controller 1408 determines that touch sensor 1410 is no longer in contact with skin, controller 1408 may stop the injection (e.g., by stopping further movement of translation mechanism 1366), may generate an error signal or message, and may retract needle 306 if it had been extended.

At step 2008, controller 1408 may send a signal to activate translation mechanism 1366. Once activated, translation mechanism 1366 may move toward second end 1306 of vial 1302 (referring to FIGS. 13 and 14), causing vial 1302 itself to move in the same direction. This may cause needle 308 to move in the opposing direction to access vial 1302 as set forth above. The movement of driver 1398 and needle 308 causes carrier 202 to move in the same direction, which sets forth the chain of events that ultimately deploys needle 306 into the user by the mechanisms set forth in FIGS. 5-11. Translation mechanism 1366 will continue to move toward second end 1306 until a desired amount of the drug contained within vial 1302 is dispensed into the user.

Method 2000 may proceed to step 2010, where controller 1408 may determine whether the injection is complete. This determination may be based on interruption of beam 1430 by piston 1316 (as described with reference to FIGS. 4A, 13, and 14). That is, when beam 1430 is broken (not received by detector 1416), controller 1408 may determine that injection is complete. Once controller 1408 determines that the injection is complete, controller 1408 may send a signal to translation mechanism 1366 to reverse the direction of rotation of the lead screw, which may cause ramp 1500 to push against ramp 243 of stop 240, enabling retraction of needle 306 as discussed above with reference to FIG. 11. In one example, controller 1408 may institute a delay after receiving an indication that beam 1430 has been interrupted. The delay may be from, e.g., 0.1 to 60 seconds. An additional end detection mechanism may be used instead of or in combination with the interruption-type sensor described above. For example, a current of the motor of translation mechanism 1366 may be utilized to determine whether an injection has been completed. That is, when piston 1316 reaches second end 1306 of vial 1302, the current on the motor will increase (e.g., as a result of piston 1316 engaging the end of vial 1302), signaling the expulsion of all or substantially all of the contents of vial 1302. One exemplary combination could include the use of beam 1430, where interruption of beam 1430 indicates that, e.g., 90 to 98 percent of the injection has been completed. Then, the current of the motor of translation mechanism 1366 could be analyzed to determine whether the remaining 2 to 10 percent of the injection has been completed. In another example, instead of using an optical switch, a delay from the initiation of the translation mechanism 1366 may be used by controller 1408 to determine when to reverse translation mechanism 1366. In one example, this delay may be from, e.g., about 1 to about 120 seconds, although other suitable times are also contemplated. In any event, the delay from initiation may be long enough to permit emptying of vial 1302.

In some examples, a timing of an injection procedure, measured from the initial activation of activating switch 1409 to retraction of needle 306 from the user after drug delivery, may be from about 20 seconds to about 90 seconds, or from about 25 seconds to about 60 seconds, from about 30 seconds to about 45 seconds, or less than or equal to about 120 seconds, or less than or equal to about 90 seconds, or less than or equal to about 60 seconds, or less than or equal to about 45 seconds, or less than or equal to about 30 seconds.

Method 2000 also may include additional steps. For example, method 2000 may include determining whether a drug within vial 1302 is too cold for delivery into the user, whether power source 1406 has enough energy to complete an injection, whether needle 306 has been prematurely deployed and/or retracted, whether the current of the motor of translation mechanism 1366 is in an appropriate range, and whether an injection procedure has extended beyond a maximum acceptable procedure time. When controller 1408 senses any of the above errors, it may communicate such errors to the user, and may end an ongoing injection by, e.g., halting or reversing translation mechanism 1366 and retracting needle 306 from the user.

Alternate Embodiments

Figure 17:
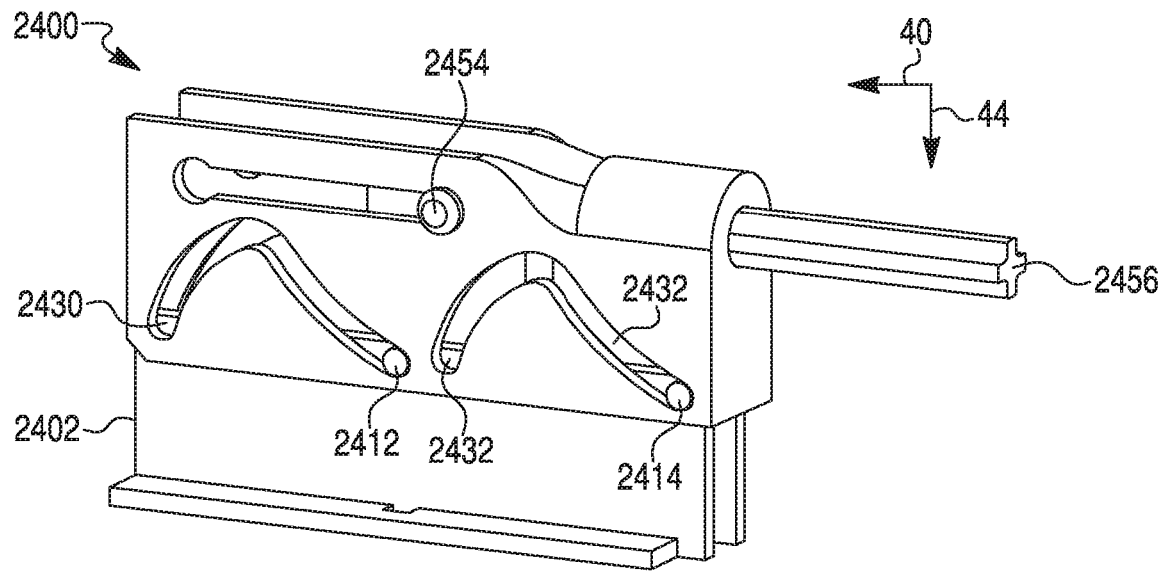
Figure 18:
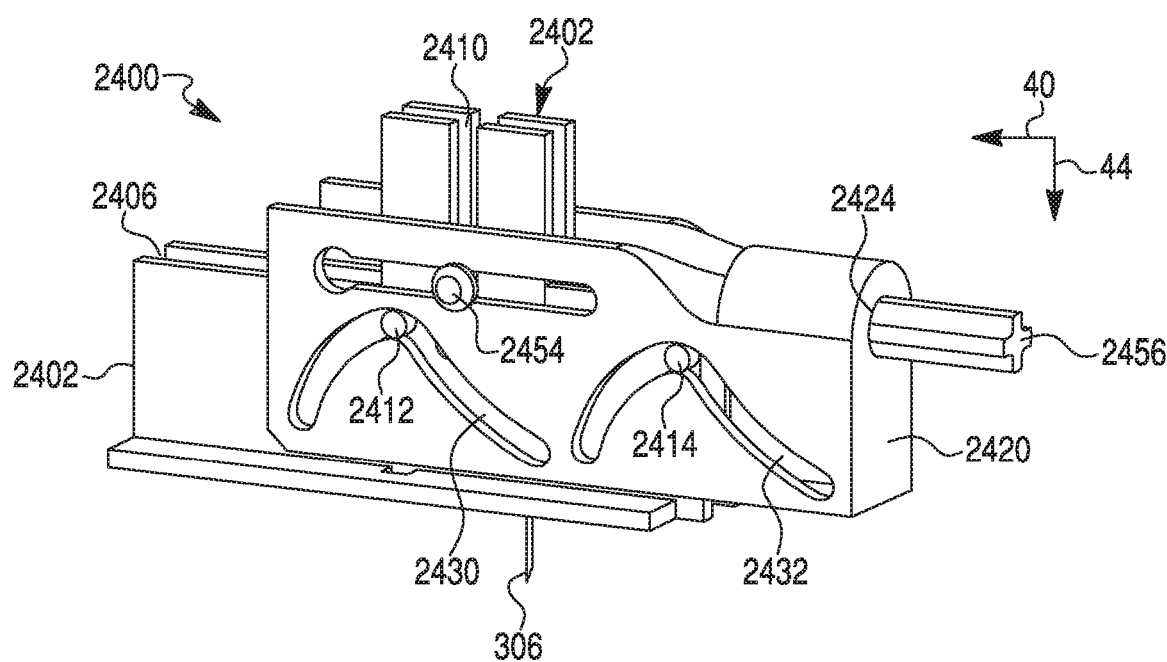
Figure 19:
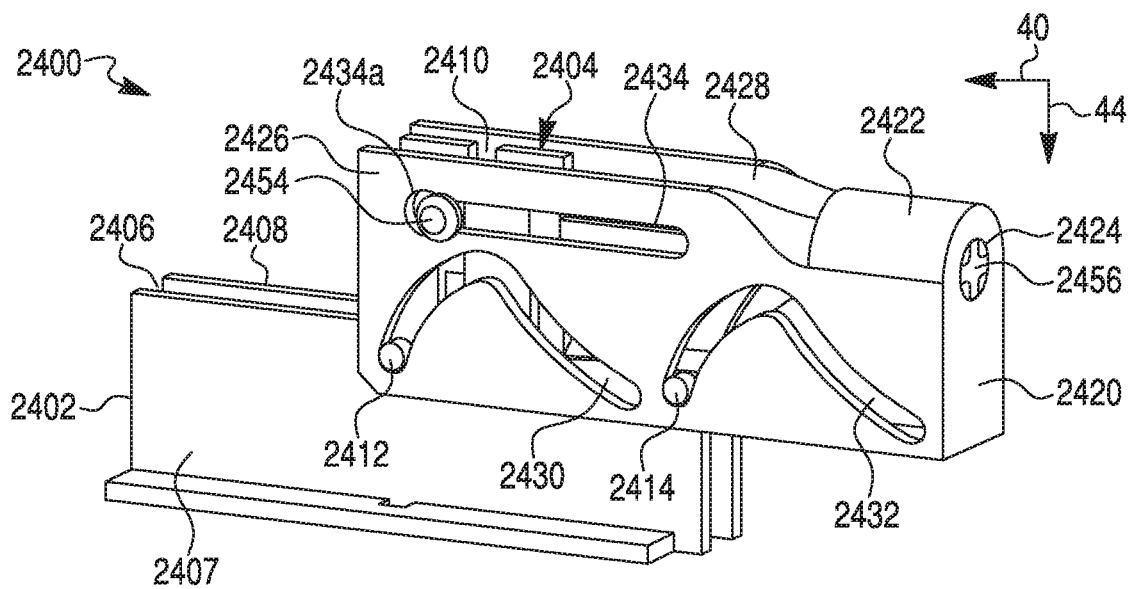

Another embodiment of a needle mechanism is shown in FIGS. 17-19. Needle mechanism 2400 may include a base 2402 and a shuttle 2420. Base 2402 may have an extension member 2404 extending away from a top surface of base 2402. Base 2402 also may include a channel 2406 extending along a longitudinal axis of base 2402 (parallel to axis 40) and recessed into a top surface of base 2402. Channel 2406 may extend through a first wall 2407 and a second wall 2408 of base 2402, and also extend through the extension member 2404. The extension member 2404 may include, for example, a slot 2410 extending from a top of the extension member 2404 through a portion of base 2402 towards the bottom surface of base 2402. The slot 2410 may be positioned generally perpendicular to channel 2406 and extend parallel to axis 44. Base 2402 may further include a pin 2412 and a second pin 2414.

Shuttle 2420 may include an end member 2422 coupled to a first wall 2426 on a first side, and a second wall 2428 on a second side. First wall 2426 and second wall 2428 may be substantially parallel to one another. The first and second walls 2426, 2428 may be spaced apart by the distance of the width of base 2402 to allow for base 2402 to translate with respect to shuttle 2420. An opening 2424 may extend through the end member 2422, which may be configured to receive a first end of a shaft 2456.

Wall 2426 may include a first slot 2430, a second slot 2432, and a driver member opening 2434 with an enlarged portion 2434a (where a projection 2454 may rest in a first, undeployed configuration). First slot 2430 may be positioned adjacent to and longitudinally spaced apart from second slot 2432. First slot 2430 engages the pin 2412 and second slot 2432 engages pin 2414. Slots 2430, 2432 may include a first curved portion or injection slope extending from a bottom toward a top of shuttle 2420, a peak positioned near opening 2434, and a second curved portion or removal slope extending from the peak to a position near the bottom of shuttle 2420. The first curved portion may have, for example, a convex shape and the second curved portion may have, for example, a concave shape when viewed from above needle mechanism 2400. The injection slope may have, for example, an angle and curvature less than the angle and curvature of the removal slope. The shallower injection slope may provide a mechanical advantage while the parts are at rest to help overcome static friction. The first curved portion allows for the insertion of a needle (e.g., needle 306 described above) into a user for administration of a medication and the second curved portion allows for removal of the needle 306 from the user. Second wall 2428 also may include two slots and an opening similar to slots 2430 and 2432, and openings 2434. The slots and openings of second wall 2428 may be arranged in a similar or identical manner as those positioned on wall 2426.

Needle mechanism 2400 also may include an elastic member or spring (not shown) that is coupled to shaft 2456. Shaft 2456 may be positioned in opening 2424 of shuttle 2420. Shaft 2456 may be coupled to a projection 2454. Projection 2454 may slide through slot 2410 of extension member 2404, and may be coupled to needle 306.

To move from an undeployed configuration shown in FIG. 17 to a deployed configuration shown in FIG. 18, the spring may be allowed to expand, causing shuttle 2420 to slide longitudinally relative to shaft 2456 along longitudinal axis 40. Due to the curvature of slots 2430 and 2432, the longitudinal force applied to shuttle 2420 also pushes shuttle 2420 downward. This downward motion also causes projection 2454 to move downward through slot 2410, deploying needle 306. When needle mechanism 2400 is in the deployed configuration, pins 2412 and 2414 are positioned at the peak or connection between the injection slope and removal slope of slots 2430 and 2432. In addition, the projection 2454 is positioned near the middle or center of opening 2434. Projection 2454 also is positioned near a middle of the slot 2410 between a top surface of the extension member 2404 and a bottom of the slot 2410. Shaft 2456 may extend out of opening 2424 beyond the end of shuttle 2420.

Once the medication has been administered, the injection needle 470 may be removed by allowing the spring to expand further. Further expansion of the spring causes shuttle 2420 to slide further longitudinally relative to shaft 2456 along the longitudinal axis 40. Due to the curvature of slots 2430 and 2432, the additional longitudinal force applied to shuttle 2420 also pushes shuttle 2420 upward. This upward motion also causes projection 2454 to move upward through slot 2410, retracting needle 306. Projection 2454 may be positioned in the drive member opening 2434 at an end closest to end surface 2422. In addition, projection 2454 is positioned near a top of slot 2410. Shaft 2456 may extend even further out of opening 2424 beyond the end of shuttle 2420.

Figure 20:
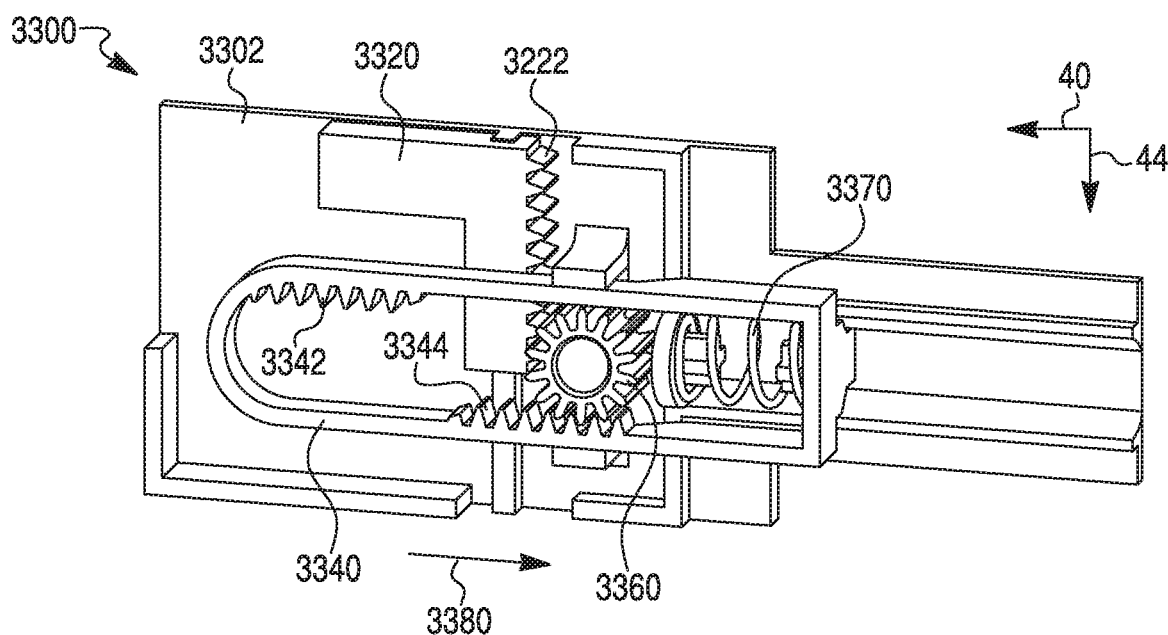

Another embodiment of an needle assembly is shown in FIG. 20. Needle assembly 3300 includes a carrier 3302, a driver 3320, a shuttle 3340, a gear 3360, and a spring (resilient member) 3370. Driver 3320 may be coupled to a fluid conduit (such as fluid conduit 300 described above) and may be configured to drive a needle at the end of that fluid conduit into the user. Driver 3320 may be similar to driver 320, except that driver 320 may include only one rack gear 3222 that is configured to be driven by gear 3360. Shuttle 3340 may be similar to shuttle 340, except that it may include a first rack 3342 and a second rack 3344. First rack 3342 and second rack 3344 may be longitudinally spaced apart but substantially parallel to one another, and may engage gear 3360 at different times. In some examples, first rack 3342 and second rack 3344 may be configured to engage gear 3360 only at different times. Second rack 3344 may cause gear 3360 to rotate in a first direction (e.g., counter-clockwise) when shuttle 3340 moves in direction 3380 along longitudinal axis 40, while first rack 3342 may cause gear 3360 to move in a second direction opposing the first direction (e.g., clockwise) when shuttle 3340 moves in direction 3380. The rotation of gear 3360 in the first direction may move driver 3320 downward via rack 3222 and urge a needle into the user, and the rotation of gear 3360 in the second direction may move driver 3320 upward to retract the needle out of the user. Expansion of spring 3370, which may be coupled to both carrier 3302 and an inner surface of shuttle 3340 may move shuttle 3340 in direction 3380 to initiate deployment and subsequent retraction of a needle. Additionally, it is contemplated that a stop, similar to stop 240, may be used to impede longitudinal movement of shuttle 3340 when driver 3320 (and an associated needle) are in a deployed configuration. The stop could then be moved out of the path of shuttle 3340 to enable retraction of driver 3320 and its associated needle.

Figure 21:
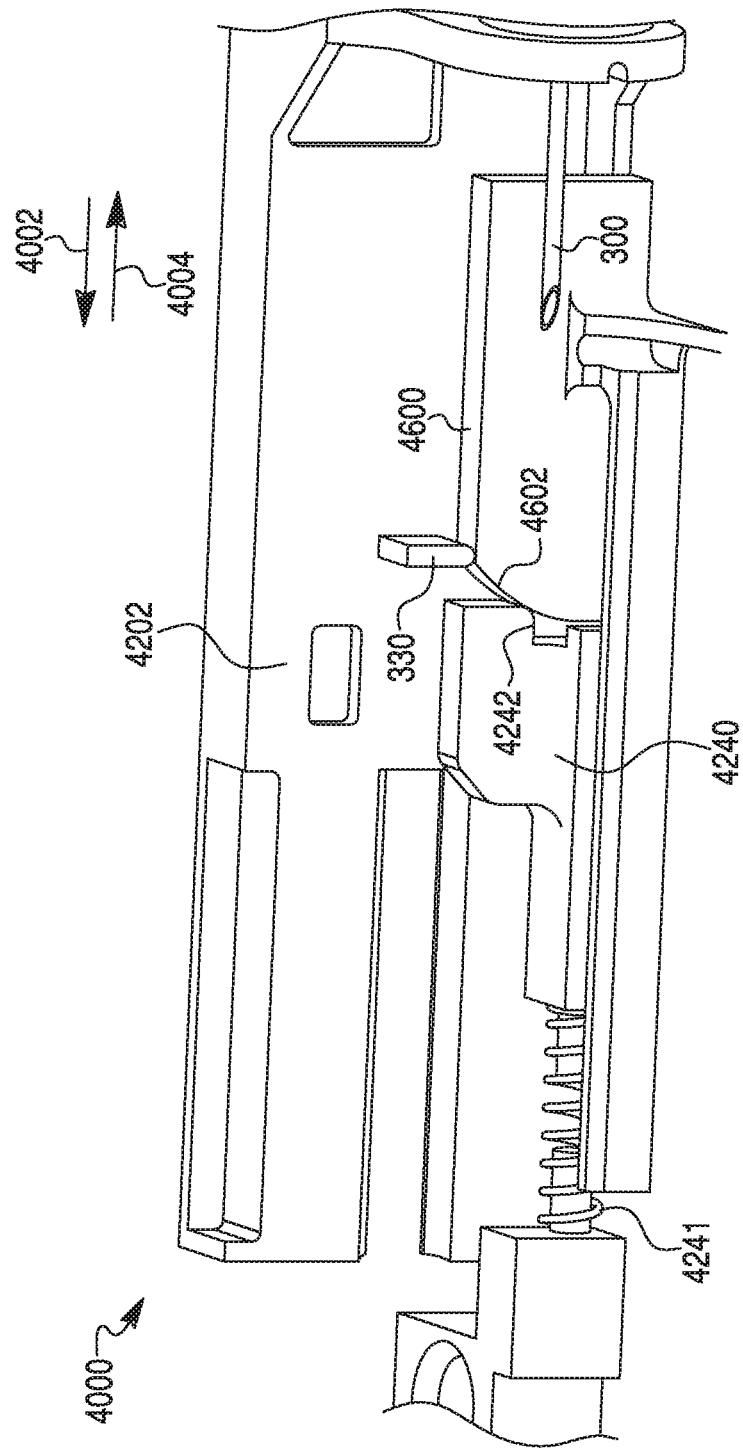

Yet another embodiment of a needle assembly is shown in FIG. 21. Needle assembly 4000 includes a carrier 4202 and a driver (shown only via protrusion 330). Needle assembly 4000 also may include the following components which are not shown, but which may be substantially similar to components described above by the same name, such as, e.g., a shuttle, deployment and retraction gears, and a spring. The driver of needle assembly 4000 may be coupled to a fluid conduit (such as fluid conduit 300) and may be configured to drive a needle at the end of that fluid conduit into the user. In an undeployed configuration (shown in FIG. 21), protrusion 330 of the driver may be blocked by an impediment 4600. Carrier 4202 may be urged in direction 4002 to enable protrusion 330 to slide down ramp 4602, moving the driver and associated needle from the retracted configuration to a deployed configuration. Carrier 4202 may be urged in direction 4002 by, e.g., translation mechanism 1366 and vial 1302, in a substantially similar manner as set forth above with respect to carrier 202.

Needle assembly 4000 may include a stop 4240 that is separate from carrier 4202. Stop 4240 may be urged in direction 4004 by a spring 4241. An end of stop 4240 may include an overhang 4242, which may help maintain the driver in the deployed configuration by blocking a retraction path of protrusion 330. Thus, when the driver is deployed, protrusion 330 may be positioned underneath overhang 4242 of stop 4240, preventing retraction of the driver until stop 4240 is moved. Retraction of the driver and needle may be accomplished by, e.g., reversing the motor of translation mechanism 1366, which may, via one or more mechanical linkages (not shown), apply a force against stop 4240 in the direction 4002 to compress spring 4241. The movement of stop 4240 in the direction 4002 may provide clearance for protrusion 330 to move back to the retracted configuration.

Figure 22:
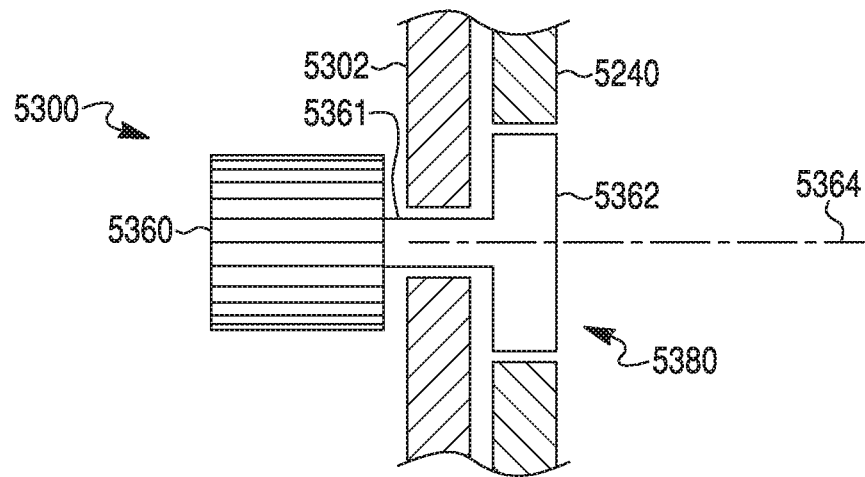
Figure 23:
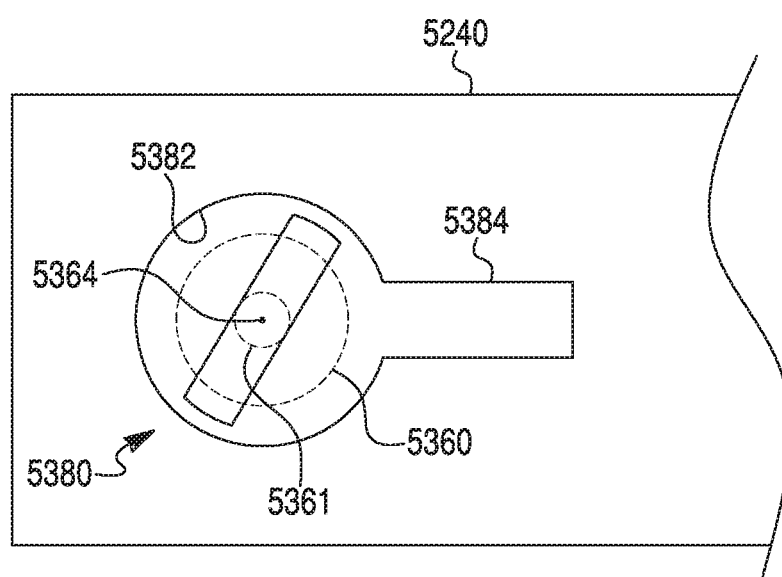

Yet another embodiment of a needle assembly is shown in FIGS. 22 and 23. Needle assembly 5300 includes a carrier 5302. In this embodiment, a stop 5240 may be configured to directly impede rotation of a deployment and/or retraction gear 5360 instead of directly impeding either a shuttle or driver of the needle assembly. In this embodiment, gear 5360 may be coupled to a toggle 5362 via a shaft 5361. Gear 5360 may rotate about axis 5364 to facilitate deployment and/or retraction of an associated driver and/or needle. Toggle 5362 may have a length that extends substantially perpendicular to axis 5364, and also may rotate about axis 5364.

Stop 5240 may include an opening 5380, through which toggle 5362 may be disposed. Opening 5380 may include a circular portion 5382, and a restricting portion 5384. Circular portion 5382 may have a diameter that is greater than a length of toggle 5362 to enable unimpeded rotation of toggle 5362 (and gear 5360) while toggle 5362 is disposed within circular portion 5382. Stop 5240 may be slidable relative to carrier 5302 by any suitable mechanism. When stop 5240 and carrier 5302 are slid relative to one another, toggle 5362 may slide within restricting portion 5384, which may be sized to restrict rotation of toggle 5362 (and gear 5360). For example, when toggle 5362 is generally rectangular as shown, restricting portion 5384 also may be rectangular.

Notably, reference herein to "one embodiment," or "an embodiment" means that a particular feature, structure, or characteristic described in connection with the embodiment may be included, employed and/or incorporated in one, some or all of the embodiments of the present disclosure. The usages or appearances of the phrase "in one embodiment" or "in another embodiment" in the specification are not referring to the same embodiment, nor are separate or alternative embodiments necessarily mutually exclusive of one or more other embodiments, nor limited to a single exclusive embodiment. The same applies to the terms "implementation," and "example." The present disclosure are neither limited to any single aspect nor embodiment thereof, nor to any combinations and/or permutations of such aspects and/or embodiments. Moreover, each of the aspects of the present disclosure, and/or embodiments thereof, may be employed alone or in combination with one or more of the other aspects of the present disclosure and/or embodiments thereof. For the sake of brevity, certain permutations and combinations are not discussed and/or illustrated separately herein.

Further, as indicated above, an embodiment or implementation described herein as "exemplary" is not to be construed as preferred or advantageous, for example, over other embodiments or implementations; rather, it is intended convey or indicate the embodiment or embodiments are example embodiment(s).

What is claimed is:
1. An injection device, comprising:
 a needle movable from a retracted configuration to a deployed configuration;
 a piston configured to move within a vial;
 a motor configured to apply force against the piston; and
 a controller coupled to the motor, wherein the controller is configured to:

receive an indication that the injection device is positioned in contact with a user;

after receiving the indication, sending a signal to the motor to apply force against the piston in a first direction, wherein applying force in the first direction causes the needle to move from the retracted configuration to the deployed configuration; and without requiring any intervention by a user after receiving the indication, and after sending the signal to the motor to apply force against the piston in the first direction, automatically sending a signal to the motor to apply force against the piston in a second direction, wherein applying force in the second direction causes the needle to retract.

2. The injection device of claim 1, further including a housing enclosing the vial, the piston, the motor, the controller, and the needle when the needle is in the retracted configuration, wherein the needle extends out of the housing in the deployed configuration.

3. The injection device of claim 1, further including a cover or a shield that contains a distalmost portion of the needle in the retracted configuration.

4. The injection device of claim 1, further including an audio module, a visual module, and a haptic module, each of the modules being coupled to the controller and configured to provide feedback to a user of the injection device.

5. The injection device of claim 1, wherein the vial is configured to be in fluid communication with the needle, further including a top that seals an opening of the vial, the top including a portion including a rubber material that is permeable to a sterilant, wherein the needle includes a proximalmost portion configured to be coupled with the vial, and, before the needle and vial are in fluid communication with one another, the proximalmost portion of the needle is disposed within the portion formed of the rubber material.

6. The injection device of claim 1, further including a cantilever coupled to the controller, and movable by the needle, wherein, when the needle is in the retracted configuration, the cantilever forms part of an open circuit that signals to the controller that the needle is in the retracted configuration, and when the needle is in the deployed configuration, the cantilever forms part of a closed circuit that signals to the controller that the needle is in the deployed configuration.

7. The injection device of claim 1, further including one or more spring contacts configured to form an electrical connection between the motor to the controller.

8. The injection device of claim 1, further including an activating switch movable between an extended position and a depressed position;
wherein the indication is based at least in part on the activating switch being in the depressed position.

9. The injection device of claim 1, further including a touch sensor configured to detect contact with skin,
wherein the indication is based at least in part on the touch sensor detecting contact with skin.

10. The injection device of claim 9, wherein the touch sensor includes a capacitive sensing electrode and is configured to detect contact with skin based on a change in a capacitance of the capacitive sensing electrode.

11. The injection device of claim 1, further including:
an emitter configured to transmit light through the vial; and
a detector configured to receive the light and to detect interruption of the light by the piston.

12. The injection device of claim 11, wherein the controller is further configured to send the signal to the motor to apply force against the piston in the second direction in response to interruption of the light by the piston.

13. The injection device of claim 11, wherein the controller is further configured, after a predetermined delay, to send the signal to the motor to apply force against the piston in the second direction in response to interruption of the light by the piston.

14. The injection device of claim 1, further including a wireless communication module configured to transmit to a remote device one or more of: diagnostic information of the injection device, information indicative of an error state of the injection device, and information indicative of completion of an injection.

15. The injection device of claim 1, further including a wireless communication module configured to receive an activation command from a remote device, wherein the indication is based at least in part on the activation command.

16. The injection device of claim 1, wherein the vial is configured to be in fluid communication with the needle.

17. The injection device of claim 1, wherein in response to the motor applying force against the piston in the first direction, the needle is put in fluid communication with the vial.

18. A controller for an injection device comprising:
one or more memories storing instructions; and
one or more processors operatively connected to the one or more memories, the one or more processors configured to execute the instructions to:
receive an indication that the injection device is positioned in contact with a user;
after receiving the indication, send a signal to a motor to apply force against a piston in a first direction within a vial, wherein applying force in the first direction causes a needle to move from a retracted configuration to a deployed configuration; and
without requiring any intervention by a user after receiving the indication, and after sending the signal to the motor to apply force against the piston in the first direction, automatically sending a signal to the motor to apply force against the piston in a second direction, wherein applying force in the second direction causes the needle to retract.

19. The controller of claim 18, wherein the controller is further configured to:
receive, from a detector, a light interruption signal indicative of an interruption of a light transmitted through the vial by an emitter; and
send the signal to the motor to apply force against the piston in the second direction in response to the light interruption signal.

20. The controller of claim 18, wherein the controller is further configured to:
receive, from a detector, a light interruption signal indicative of an interruption of a light transmitted through the vial by an emitter; and
send, after a predetermined delay, the signal to the motor to apply force against the piston in the second direction in response to the light interruption signal.

* * * * *